(12) United States Patent
Sieg et al.

(10) Patent No.: US 7,767,786 B2
(45) Date of Patent: Aug. 3, 2010

(54) NEURAL REGENERATION PEPTIDES AND METHODS FOR THEIR USE IN TREATMENT OF NEURAL INJURY OR DEGENERATION

(75) Inventors: Frank Sieg, Auckland (NZ); Paul Hughes, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 1155 days.

(21) Appl. No.: 10/225,838

(22) Filed: Aug. 22, 2002

(65) Prior Publication Data

US 2003/0211990 A1    Nov. 13, 2003

Related U.S. Application Data

(60) Provisional application No. 60/314,952, filed on Aug. 24, 2001.

(51) Int. Cl.
*C07K 2/00* (2006.01)
*C07K 4/00* (2006.01)
*C07K 7/00* (2006.01)
*C07K 14/00* (2006.01)
*C12P 21/00* (2006.01)

(52) U.S. Cl. ............ 530/300; 530/350; 435/69.1; 435/70.1; 435/70.3

(58) Field of Classification Search ........ None
See application file for complete search history.

(56) References Cited

U.S. PATENT DOCUMENTS

| 5,834,192 | A | 11/1998 | Akerblom et al. | |
|---|---|---|---|---|
| 6,262,024 | B1 | 7/2001 | Cunningham et al. | |
| 2003/0022349 | A1* | 1/2003 | Ausubel et al. | 435/219 |
| 2005/0131212 | A1* | 6/2005 | Sieg et al. | 530/350 |

FOREIGN PATENT DOCUMENTS

| WO | WO 97/38100 | 10/1997 |
|---|---|---|
| WO | WO 98/11136 | 3/1998 |
| WO | WO9927129 | * 6/1999 |

OTHER PUBLICATIONS

Burgess et al. J of Cell Biol. 1990. 111:2129-2138.*
Bowie et al. Science, 1990, 247:1306-1310.*
Pawson et al. 2003, Science 300:445-452.*
The results of calculation from the software of ProtParam on the ExPASy website, http://us.expasy.org/cgi-bin/protparam, retrieved Sep. 26, 2007.*
K.L. Eagleson, "Rescue of Both Rapidly and Slowly Degenerating Neurons in the Dorsal Lateral Geniculate Nucleus of Adult Rats by a Cortically Derived Neuron Survival Factor", Dept. of Anatomy and Neurobiology, Medical College of PA, 1992 by Academic Press, Inc., pp. 156-162.
Joe E. Springer, "Neurotrophic Factors as Therapeutic Agents", DN&P, Sep. 1991, pp. 394-399.
K.L. Eagleson, "Different Populations of Dorsal Lateral Geniculate Nucleus Neurons Have Concentration-Specific Requirements for a Cortically Derived Neuron Survival Factor", Dept. of Anatomy and Neurobiology, Medical College of PA, 1990 by Academic Press, Inc., pp. 284-290.
Yves-Alain Barde, et al., "Purification of a new neurotophic factor from mammalian brain", EMBO Journal, vol. 1, No. 5, pp. 549-553, 1987.
Cunningham, et al. "Identification of a Survival-Promoting Peptide in Medium Conditioned by Oxidatively Stressed Cell Lines of Nervous Origin," *The Journal of Neuroscience*, Sep. 15, 1998, vol. 18. No. 18, pp. 7047-7060.

* cited by examiner

*Primary Examiner*—Christine J Saoud
*Assistant Examiner*—Chang-Yu Wang
(74) *Attorney, Agent, or Firm*—D. Benjamin Borson

(57) ABSTRACT

The invention discloses a family of neuronal migration-inducing, proliferation-promoting and neurite outgrowth promoting factors, termed NRP compounds, and provides compositions and methods for the use of NRP compounds in the treatment of brain injury and neurodegenerative disease. NRP compounds induce neurons and neuroblasts to proliferate and migrate into areas of damage caused by acute brain injury or chronic neurodegenerative disease, such as stroke, trauma, nervous system infections, demyelinating diseases, dementias, and metabolic disorders. NRP compounds may be administered directly to a subject or to a subject's cells by a variety of means including orally, intraperitoneally, intravascularly, and directly into the nervous system of a patient.

4 Claims, 27 Drawing Sheets

(9 of 27 Drawing Sheet(s) Filed in Color)

SEQUENCE LISTING

```
<160> NUMBER OF SEQ ID NOS: 27

<210> SEQ ID NO 1
<211> LENGTH: 48
<212> TYPE: DNA
<213> ORGANISM: RAT
```

<400> SEQUENCE: 1
tatgatccag aggccgcctc tgccccagga tcggggaacc cttgccat            48

<210> SEQ ID NO 2
<211> LENGTH: 16
<212> TYPE: PRT
<213> ORGANISM: RAT

<400> SEQUENCE: 2

Tyr Asp Pro Glu Ala Ala Ser Ala Pro Gly Ser Gly Asn Pro Cys His
1               5                   10                  15

<210> SEQ ID NO 3
<211> LENGTH: 48
<212> TYPE: DNA
<213> ORGANISM: ARTIFICIAL
<220> FEATURE:
<223> OTHER INFORMATION: Synthetic
<220> FEATURE:
<221> NAME/KEY: misc_feature
<222> LOCATION: (3)..(6)
<223> OTHER INFORMATION: n=c, t/u
<220> FEATURE:
<221> NAME/KEY: misc_feature
<222> LOCATION: (9)..(9)
<223> OTHER INFORMATION: n=a, t, c, g
<220> FEATURE:
<221> NAME/KEY: misc_feature
<222> LOCATION: (12)..(12)
<223> OTHER INFORMATION: n=g,a
<220> FEATURE:
<221> NAME/KEY: misc_feature
<222> LOCATION: (15)..(36)
<223> OTHER INFORMATION: n=a,t,c,g
<220> FEATURE:
<221> NAME/KEY: misc_feature
<222> LOCATION: (39)..(39)
<223> OTHER INFORMATION: n=c, t/u
<220> FEATURE:
<221> NAME/KEY: misc_feature
<222> LOCATION: (42)..(42)
<223> OTHER INFORMATION: n=a,t,c,g
<220> FEATURE:
<221> NAME/KEY: misc_feature
<222> LOCATION: (45)..(48)
<223> OTHER INFORMATION: n=c, t/u

<400> SEQUENCE: 3
tanganccng angcngcntc ngcnccnggn tcnggnaanc cntgncan             48

<210> SEQ ID NO 4
<211> LENGTH: 333
<212> TYPE: DNA
<213> ORGANISM: HUMAN

<400> SEQUENCE: 4
atgagagtca gagtacaact caagtctaat gtccaagttg gagcaggaca ctcagcaaag    60
gatccagagg caaggagagc acctggaagc ctacatccct gtctagcagc atcatgctca   120
gctgctggcc tgcacacaag ctcgtggaag aacctgtttt tgatagaagg actagtaagt   180
atttgcctag ggcacatagt tgtacaagag acggacgttt ttaggtcctt gcggtttctt   240
gcatttccag aaaacttgct tcaaatattt ttccagatgc aaaattcctt ggatccttgt   300
tttagaatga atctattaaa aacttcacat taa                               333

<210> SEQ ID NO 5
<211> LENGTH: 110

```
<212> TYPE: PRT
<213> ORGANISM: HUMAN

<400> SEQUENCE: 5

Met Arg Val Arg Val Gln Leu Lys Ser Asn Val Gln Val Gly Ala Gly
1               5                   10                  15

His Ser Ala Lys Asp Pro Glu Ala Arg Arg Ala Pro Gly Ser Leu His
            20                  25                  30

Pro Cys Leu Ala Ala Ser Cys Ser Ala Ala Gly Leu His Thr Ser Ser
        35                  40                  45

Trp Lys Asn Leu Phe Trp Ile Glu Gly Leu Val Ser Ile Cys Leu Gly
50                  55                  60

His Ile Val Val Gln Glu Thr Asp Val Phe Arg Ser Leu Arg Phe Leu
65                  70                  75                  80

Ala Phe Pro Glu Asn Leu Leu Gln Ile Phe Phe Gln Met Gln Asn Ser
                85                  90                  95

Leu Asp Pro Cys Phe Arg Met Asn Leu Leu Lys Thr Ser His
            100                 105                 110

<210> SEQ ID NO 6
<211> LENGTH: 336
<212> TYPE: DNA
<213> ORGANISM: HUMAN

<400> SEQUENCE: 6
atgaaaataa atgtattaat taaattaatg accaagtcag attcttttaa aagccaagcc      60
aggggccaag ttcccccatt tctagggggg gtggggtgcc cctggttttt tcaaacaagg     120
ttttggggcc atagttttgc agttaaactg gcctccaacc tttcccaggc agagaaattg     180
gtccttcagc aaacccttc ccaaaaaggc ctagacggag caaaaaaagc tgtgggggga     240
ctcggaaaac taggaaaaga tgcagtcgaa gatctagaaa gcgtgggtaa aggagccgtc     300
catgacgtta aagacgtcct tgactcagta ctatag                              336

<210> SEQ ID NO 7
<211> LENGTH: 111
<212> TYPE: PRT
<213> ORGANISM: HUMAN

<400> SEQUENCE: 7

Met Lys Ile Asn Val Leu Ile Lys Leu Met Thr Lys Ser Asp Ser Phe
1               5                   10                  15

Lys Ser Gln Ala Arg Gly Gln Val Pro Pro Phe Leu Gly Gly Val Gly
            20                  25                  30

Cys Pro Trp Phe Phe Gln Thr Arg Phe Trp Gly His Ser Phe Ala Val
        35                  40                  45

Lys Leu Ala Ser Asn Leu Ser Gln Ala Glu Lys Leu Val Leu Gln Gln
50                  55                  60

Thr Leu Ser Gln Lys Gly Leu Asp Gly Ala Lys Lys Ala Val Gly Gly
65                  70                  75                  80

Leu Gly Lys Leu Gly Lys Asp Ala Val Glu Asp Leu Glu Ser Val Gly
                85                  90                  95

Lys Gly Ala Val His Asp Val Lys Asp Val Leu Asp Ser Val Leu
            100                 105                 110

<210> SEQ ID NO 8
<211> LENGTH: 438
<212> TYPE: DNA
```

```
<213> ORGANISM: HUMAN
<220> FEATURE:
<221> NAME/KEY: misc_feature
<222> LOCATION: (353)..(354)
<223> OTHER INFORMATION: n=modified form of a/t/c/g; n=a/t/c/g

<400> SEQUENCE: 8
atggctgttg tgttacttgc accatttggg gacatcagcc aggaaatcac aaaggttggg      60
acagggactc cagggagggc tgaggccggg ggccaggtgt ctccatgcct ggcggcgtcc     120
tgcagtcagg cctatggcgc catcttggct cactgcaacc tctgcctccc aggttcaatg     180
attaaaaaaa agaagaaatt tatagttgaa atagaaagtc aacctttaaa gtcttacagg     240
gaaaattcta cccatttttcc cagaccagtc ctaaatctta tgcgaaaaca ctgtggggaa     300
aagggggaag aagggccttg tttctctccc aagcaaatgg gggagaggcg agnntgtggc     360
ggagggctag ggttggctcg cgagatcact aatttaacat ccgctcatct gttggtcttg     420
aatatcagca accagtga                                                   438

<210> SEQ ID NO 9
<211> LENGTH: 145
<212> TYPE: PRT
<213> ORGANISM: HUMAN
<220> FEATURE:
<221> NAME/KEY: SITE
<222> LOCATION: (118)..(118)
<223> OTHER INFORMATION: X=UNCERTAIN. AMINO ACID COULD NOT BE
      DETERMINED.

<400> SEQUENCE: 9

Met Ala Val Val Leu Leu Ala Pro Phe Gly Asp Ile Ser Gln Glu Ile
1               5                   10                  15

Thr Lys Val Gly Thr Gly Thr Pro Gly Arg Ala Glu Ala Gly Gly Gln
            20                  25                  30

Val Ser Pro Cys Leu Ala Ala Ser Cys Ser Gln Ala Tyr Gly Ala Ile
        35                  40                  45

Leu Ala His Cys Asn Leu Cys Leu Pro Gly Ser Met Ile Lys Lys Lys
    50                  55                  60

Lys Lys Phe Ile Val Glu Ile Glu Ser Gln Pro Leu Lys Ser Tyr Arg
65                  70                  75                  80

Glu Asn Ser Thr His Phe Pro Arg Gly Val Leu Asn Leu Met Arg Lys
                85                  90                  95

His Cys Gly Glu Lys Gly Glu Gly Pro Cys Phe Ser Pro Lys Gln
            100                 105                 110

Met Gly Glu Arg Arg Xaa Cys Gly Gly Gly Leu Gly Leu Ala Arg Glu
        115                 120                 125

Ile Thr Asn Leu Thr Ser Ala His Leu Leu Val Leu Asn Ile Ser Asn
    130                 135                 140

Gln
145

<210> SEQ ID NO 10
<211> LENGTH: 801
<212> TYPE: DNA
<213> ORGANISM: HUMAN

<400> SEQUENCE: 10
atgctggacc cgtcttccag cgaagaggag tcggacgagg ggctggaaga ggaaagccgc      60
gatgtgctgg tggcagccgg cagctcgcag cgagctcctc cagccccgac tcgggaaggg     120
```

-continued

```
cggcgggacg cgccggggcg cgcggcggc ggcggcgcgg ccagatctgt gagcccgagc    180
ccctctgtgc tcagcgaggg gcgagacgag ccccagcggc agctggacca tgagcaggag    240
cggaggatcc gcctgcagct ctacgtcttc gtcgtgaggt gcatcgcgta cccttcaac     300 gccaagcagc ccaccgacat ggcccggagg cagcagaagc ttaacaaaca acagttgcag    360
ttactgaaag aacggttcca ggccttcctc aatggggaaa cccaaattgt agctgacgaa    420
gcattttgca acgcagttcg gagttattat gaggtttttc taaagagtga ccgagtggcc    480
agaatggtac agagtggagg gtgttctgct aaggacttca gagaagtatt taagaaaaac    540
atagaaaaac gtgtgcggag tttgccagaa gtggatggct tgagcaaaga gacagtgttg    600
agctcatgga tagccaaata tgatgccatt tacagaggtg aagaggactt gtgcaaacag    660
ccaaatagaa tggcccctaag tgcagtgtct gaacttattc tgagcaagga acaactctat    720
gaaatgtttc agcagattct gggtattaaa aaactggaac caccgctcct ttataatgca    780
tgtcaggtaa gtggtctctg a                                              801
```

<210> SEQ ID NO 11
<211> LENGTH: 266
<212> TYPE: PRT
<213> ORGANISM: HUMAN

<400> SEQUENCE: 11

```
Met Leu Asp Pro Ser Ser Glu Glu Glu Ser Asp Glu Gly Leu Glu
  1               5                  10                  15

Glu Glu Ser Arg Asp Val Leu Val Ala Ala Gly Ser Ser Gln Arg Ala
             20                  25                  30

Pro Pro Ala Pro Thr Arg Glu Gly Arg Arg Asp Ala Pro Gly Arg Ala
         35                  40                  45

Gly Gly Gly Gly Ala Ala Arg Ser Val Ser Pro Ser Pro Ser Val Leu
     50                  55                  60

Ser Glu Gly Arg Asp Glu Pro Gln Arg Gln Leu Asp Asp Glu Gln Glu
 65                  70                  75                  80

Arg Arg Ile Arg Leu Gln Leu Tyr Val Phe Val Val Arg Cys Ile Ala
                 85                  90                  95

Tyr Pro Phe Asn Ala Lys Gln Pro Thr Asp Met Ala Arg Arg Gln Gln
            100                 105                 110

Lys Leu Asn Lys Gln Gln Leu Gln Leu Leu Lys Glu Arg Phe Gln Ala
        115                 120                 125

Phe Leu Asn Gly Glu Thr Gln Ile Val Ala Asp Glu Ala Phe Cys Asn
    130                 135                 140

Ala Val Arg Ser Tyr Tyr Glu Val Phe Leu Lys Ser Asp Arg Val Ala
145                 150                 155                 160

Arg Met Val Gln Ser Gly Gly Cys Ser Ala Asn Asp Phe Arg Glu Val
                165                 170                 175

Phe Lys Lys Asn Ile Glu Lys Arg Val Arg Ser Leu Pro Glu Ile Asp
            180                 185                 190

Gly Leu Ser Lys Glu Thr Val Leu Ser Ser Trp Ile Ala Lys Tyr Asp
        195                 200                 205

Ala Ile Tyr Arg Gly Glu Glu Asp Leu Cys Lys Gln Pro Asn Arg Met
    210                 215                 220

Ala Leu Ser Ala Val Ser Glu Leu Ile Leu Ser Lys Glu Gln Leu Tyr
225                 230                 235                 240

Glu Met Phe Gln Gln Ile Leu Gly Ile Lys Lys Leu Glu His Gln Leu
                245                 250                 255
```

Leu Tyr Asn Ala Cys Gln Val Ser Gly Leu
            260                 265

<210> SEQ ID NO 12
<211> LENGTH: 237
<212> TYPE: DNA
<213> ORGANISM: HUMAN

<400> SEQUENCE: 12
atgagagaca aacaacatct aaatgcaaga cataaaaagg aaaggaagga gagatcatat      60
agtacaacac tacaaggtgt tctcaacaaa aagtctttgt tagacttcaa taatactatt    120
tggtacttct atcagcaaat aggaagcatt ccaatactta ttagatcctc taccatcaga    180
cacagaaatt acctagaaaa cagaaatgta ttgccaaatc tcaaacaaga gggctga       237

<210> SEQ ID NO 13
<211> LENGTH: 78
<212> TYPE: PRT
<213> ORGANISM: HUMAN

<400> SEQUENCE: 13

Met Arg Asp Lys Gln His Leu Asn Ala Arg His Lys Lys Glu Arg Lys
1               5                   10                  15

Glu Arg Ser Tyr Ser Thr Thr Leu Gln Gly Val Leu Asn Lys Lys Ser
            20                  25                  30

Leu Leu Asp Phe Asn Asn Thr Ile Trp Tyr Phe Tyr Gln Gln Ile Gly
        35                  40                  45

Ser Ile Pro Ile Leu Ile Arg Ser Ser Thr Ile Arg His Arg Asn Tyr
    50                  55                  60

Leu Glu Asn Arg Asn Val Leu Pro Asn Leu Lys Gln Glu Gly
65                  70                  75

<210> SEQ ID NO 14
<211> LENGTH: 449
<212> TYPE: DNA
<213> ORGANISM: MOUSE

<400> SEQUENCE: 14
ggcagcctcg agatggggaa gatggcggct gctgtggctt cattagccac gctggctgca      60
gagcccagag aggatgcttt ccggaagctt ttccgcttct accggcagag ccggccgggg    120
acagcggacc tggagccgt catcgacttc tcagaggcgc acttggctcg agccccgaag    180
cccggcgtgc cccaggtagg aaaggaggag tagtgtgtgc cagcctagcg gccgactggg    240
ccacccgaga ctgggccgcc tccgcggctt tggagggaag ccctgctgg gcctgtccag    300 tgagctgtaa tgtcgagcga tgagcgacca gctgcctcgc tgtcccaacg ctctggccac    360
ggcttgtgcc ttgccgccat ttcccccaac ccacgcgggc cacggcttgt gccctgccgc    420
catttccccc aacccacgcg accttgctc                                       449

<210> SEQ ID NO 15
<211> LENGTH: 66
<212> TYPE: PRT
<213> ORGANISM: MOUSE

<400> SEQUENCE: 15

Met Gly Lys Met Ala Ala Ala Val Ala Ser Leu Ala Thr Leu Ala Ala
1               5                   10                  15

Glu Pro Arg Glu Asp Ala Phe Arg Lys Leu Phe Arg Phe Tyr Arg Gln

Ser Arg Pro Gly Thr Ala Asp Leu Gly Ala Val Ile Asp Phe Ser Glu
        35                  40                  45

Ala His Leu Ala Arg Ser Pro Lys Pro Gly Val Pro Gln Val Gly Lys
    50                  55                  60

Glu Glu
65

<210> SEQ ID NO 16
<211> LENGTH: 342
<212> TYPE: DNA
<213> ORGANISM: MOUSE

<400> SEQUENCE: 16
atgaatcgaa accctggagt ccctcgagat ggggaagatg gcggctgctg tggcttcatt    60
agccacgctg gctgcagagc ccagagagga tgctttccgg aagcttttcc gcttctaccg   120
gcagagccgg ccggggacag cggacctggg agccgtcatc gacttctcag aggcgcactt   180
ggctcggagc ccgaagcccg gcgtgcccca ggtaggaaag gaggagtagt gtgtgccagc   240
ctagcggccg actgggccac ccgagactgg gccgcctccg ggccggcttt ggagggaagc   300
ccctgctggg cctgtccagt gagctgtaat gtcgagcgat ga                      342

<210> SEQ ID NO 17
<211> LENGTH: 113
<212> TYPE: PRT
<213> ORGANISM: MOUSE

<400> SEQUENCE: 17

Met Asn Arg Asn Pro Gly Val Pro Arg Asp Gly Glu Asp Gly Gly Cys
1               5                   10                  15

Cys Gly Phe Ile Ser His Ala Gly Cys Arg Ala Gln Arg Gly Cys Phe
            20                  25                  30

Pro Glu Ala Phe Pro Leu Leu Pro Ala Glu Pro Ala Gly Asp Ser Gly
        35                  40                  45

Pro Gly Ser Arg His Arg Leu Leu Arg Gly Ala Leu Ser Glu Pro
    50                  55                  60

Glu Ala Arg Arg Ala Pro Gly Arg Lys Gly Gly Val Val Cys Ala Ser
65                  70                  75                  80

Leu Ala Ala Asp Trp Ala Thr Arg Asp Trp Ala Ala Ser Gly Pro Ala
                85                  90                  95

Leu Glu Gly Ser Pro Cys Trp Ala Cys Pro Val Ser Cys Asn Val Glu
            100                 105                 110

Arg

<210> SEQ ID NO 18
<211> LENGTH: 24
<212> TYPE: PRT
<213> ORGANISM: HUMAN

<400> SEQUENCE: 18

Lys Asp Pro Glu Ala Arg Arg Ala Pro Gly Ser Leu His Pro Cys Leu
1               5                   10                  15

Ala Ala Ser Cys Ser Ala Ala Gly
            20

<210> SEQ ID NO 19
<211> LENGTH: 426

-continued

<212> TYPE: DNA
<213> ORGANISM: MOUSE

<400> SEQUENCE: 19

```
atgtgcactc tgcaggtatg gtcttcctcc ctcccttccc tcccccacct ctctgagggg     60
tcaggggtca gcatttggat gctgctccca ccaggcccag ctttagaaat gaattcctcc    120
ggcctccttt atactcttga gacctcctgg ggaaccagga ccctcttggc tcctctggtg    180
acatacatgg gatctgatgc atctgaggtg gatgcaagaa gagcaaaaaa gagtctccac    240
tgcatcctgt ctgacaccag ccatccccgg ggccatgccc ggaatgagag gaggcttggc    300
cttggggttt ggaagaccga gctttgggtc cagaccctgc tatcactgat ggtgacatcc    360
tgggaagttt atgaaactcg ttcgtgcctc agtttcccca tcaggccttt agctcactgg    420
ggataa                                                                426
```

<210> SEQ ID NO 20
<211> LENGTH: 141
<212> TYPE: PRT
<213> ORGANISM: MOUSE

<400> SEQUENCE: 20

```
Met Cys Thr Leu Gln Val Trp Ser Ser Ser Leu Pro Ser Leu Pro His
1               5                   10                  15

Leu Ser Glu Gly Ser Gly Val Ser Ile Trp Met Leu Leu Pro Pro Gly
            20                  25                  30

Pro Ala Leu Glu Met Asn Ser Ser Gly Leu Leu Tyr Thr Leu Glu Thr
        35                  40                  45

Ser Trp Gly Thr Arg Thr Leu Leu Ala Pro Leu Val Thr Tyr Met Gly
    50                  55                  60

Ser Asp Ala Ser Glu Val Asp Ala Arg Arg Ala Lys Lys Ser Leu His
65                  70                  75                  80

Cys Ile Leu Ser Asp Thr Ser His Pro Arg Gly His Ala Arg Asn Glu
                85                  90                  95

Arg Arg Leu Gly Leu Gly Val Trp Lys Thr Glu Leu Trp Val Gln Thr
            100                 105                 110

Leu Leu Ser Leu Met Val Thr Ser Trp Glu Val Tyr Glu Thr Arg Ser
        115                 120                 125

Cys Leu Ser Phe Pro Ile Arg Leu Leu Ala His Trp Gly
    130                 135                 140
```

<210> SEQ ID NO 21
<211> LENGTH: 498
<212> TYPE: PRT
<213> ORGANISM: Mycobacterium tuberculosis

<400> SEQUENCE: 21

```
Met Ser Phe Val Val Thr Ile Pro Glu Ala Leu Ala Ala Val Ala Thr
1               5                   10                  15

Asp Leu Ala Gly Ile Gly Ser Thr Ile Gly Thr Ala Asn Ala Ala Ala
            20                  25                  30

Ala Val Pro Thr Thr Thr Val Leu Ala Ala Ala Ala Asp Glu Val Ser
        35                  40                  45

Ala Ala Met Ala Ala Leu Phe Ser Gly His Ala Gln Ala Tyr Gln Ala
    50                  55                  60

Leu Ser Ala Gln Ala Ala Leu Phe His Glu Gln Phe Val Arg Ala Leu
65                  70                  75                  80
```

-continued

```
Thr Ala Gly Ala Gly Ser Tyr Ala Ala Ala Glu Ala Ala Ser Ala Ala
                85                  90                  95

Pro Leu Glu Gly Val Leu Asp Val Ile Asn Ala Pro Ala Leu Ala Leu
            100                 105                 110

Leu Gly Arg Pro Leu Ile Gly Asn Gly Ala Asn Gly Ala Pro Gly Thr
        115                 120                 125

Gly Ala Asn Gly Gly Asp Gly Gly Ile Leu Ile Gly Asn Gly Gly Ala
130                 135                 140

Gly Gly Ser Gly Ala Ala Gly Met Pro Gly Gly Asn Gly Gly Ala Ala
145                 150                 155                 160

Gly Leu Phe Gly Asn Gly Gly Ala Gly Ala Gly Asn Val Ala
                165                 170                 175

Ser Gly Thr Ala Gly Phe Gly Gly Ala Gly Ala Gly Gly Leu Leu
            180                 185                 190

Tyr Gly Ala Gly Gly Ala Gly Gly Ala Gly Gly Arg Ala Gly Gly Gly
        195                 200                 205

Val Gly Gly Ile Gly Gly Ala Gly Gly Ala Gly Gly Asn Gly Gly Leu
    210                 215                 220

Leu Phe Gly Ala Gly Gly Ala Gly Gly Val Gly Gly Leu Ala Ala Asp
225                 230                 235                 240

Ala Gly Asp Gly Gly Ala Gly Gly Asp Gly Gly Leu Phe Phe Gly Val
            245                 250                 255

Gly Gly Ala Gly Gly Ala Gly Gly Thr Gly Thr Asn Val Thr Gly Gly
        260                 265                 270

Ala Gly Gly Ala Gly Gly Asn Gly Gly Leu Leu Phe Gly Ala Gly Gly
    275                 280                 285

Val Gly Gly Val Gly Gly Asp Gly Val Ala Phe Leu Gly Thr Ala Pro
    290                 295                 300

Gly Gly Pro Gly Gly Ala Gly Gly Ala Gly Gly Leu Phe Gly Val Gly
305                 310                 315                 320

Gly Ala Gly Gly Ala Gly Gly Ile Gly Leu Val Gly Asn Gly Gly Ala
            325                 330                 335

Gly Gly Ser Gly Gly Ser Ala Leu Leu Trp Gly Asp Gly Gly Ala Gly
        340                 345                 350

Gly Ala Gly Gly Val Gly Ser Thr Thr Gly Gly Ala Gly Gly Ala Gly
    355                 360                 365

Gly Asn Ala Gly Leu Leu Val Gly Ala Gly Gly Ala Gly Gly Ala Gly
    370                 375                 380

Ala Leu Gly Gly Gly Ala Thr Gly Val Gly Gly Ala Gly Gly Asn Gly
385                 390                 395                 400

Gly Thr Ala Gly Leu Leu Phe Gly Ala Gly Gly Ala Gly Phe Gly
            405                 410                 415

Phe Gly Gly Ala Gly Gly Ala Gly Gly Leu Gly Gly Lys Ala Gly Leu
            420                 425                 430

Ile Gly Asp Gly Gly Asp Gly Gly Ala Gly Gly Asn Gly Thr Gly Ala
        435                 440                 445

Lys Gly Gly Asp Gly Gly Ala Gly Gly Gly Ala Ile Leu Val Gly Asn
        450                 455                 460

Gly Gly Asn Gly Gly Asn Ala Gly Ser Gly Thr Pro Asn Gly Ser Ala
465                 470                 475                 480

Gly Thr Gly Gly Ala Gly Gly Leu Leu Gly Lys Asn Gly Met Asn Gly
            485                 490                 495

Leu Pro
```

<210> SEQ ID NO 22
<211> LENGTH: 641
<212> TYPE: PRT
<213> ORGANISM: Epstein Barr Virus

<400> SEQUENCE: 22

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Gly Ala Gly Ala Gly Gly
        115                 120                 125

Gly Ala Gly Ala Gly Gly Ala Gly Gly Ala Gly Gly Ala Gly Gly Ala
    130                 135                 140

Gly Gly Gly Ala Gly Ala Gly Gly Ala Gly Ala Gly Ala Gly Ala Gly
145                 150                 155                 160

Gly Gly Ala Gly Gly Ala Gly Gly Ala Gly Ala Gly Gly Gly Ala Gly
                165                 170                 175

Ala Gly Gly Gly Ala Gly Gly Ala Gly Ala Gly Gly Ala Gly Ala Gly
            180                 185                 190

Ala Gly Gly Ala Gly Ala Gly Gly Ala Gly Ala Gly Gly Gly Ala Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Ala Gly Ala Gly Gly
            260                 265                 270

Gly Gly Ala Gly Gly Ala Gly Ala Gly Gly Ala Gly Gly Ala Gly Gly
        275                 280                 285

Ala Gly Gly Ala Gly Gly Ala Gly Ala Gly Gly Ala Gly Gly Ala Gly
    290                 295                 300

Ala Gly Gly Ala Gly Gly Ala Gly Ala Gly Gly Ala Gly Ala Gly Gly
305                 310                 315                 320

Gly Ala Gly Ala Gly Gly Gly Arg Gly Arg Gly Gly Ser Gly Gly Arg
                325                 330                 335

Gly Arg Gly Gly Ser Gly Gly Arg Gly Arg Gly Gly Ser Gly Gly Arg
            340                 345                 350

Arg Gly Arg Gly Arg Glu Arg Ala Arg Gly Gly Ser Arg Glu Arg Ala
        355                 360                 365

Arg Gly Arg Gly Arg Gly Arg Gly Glu Lys Arg Pro Arg Ser Pro
```

```
                370             375             380
Ser Ser Gln Ser Ser Ser Gly Ser Pro Pro Arg Arg Pro Pro
385                 390             395                 400

Gly Arg Arg Pro Phe Phe His Pro Val Gly Glu Ala Asp Tyr Phe Glu
            405             410                 415

Tyr His Gln Glu Gly Gly Pro Asp Gly Glu Pro Asp Val Pro Pro Gly
                420             425             430

Ala Ile Glu Gln Gly Pro Ala Asp Asp Pro Gly Glu Gly Pro Ser Thr
            435             440             445

Gly Pro Arg Gly Gln Gly Asp Gly Gly Arg Arg Lys Lys Gly Gly Trp
450             455             460

Phe Gly Lys His Arg Gly Gln Gly Gly Ser Asn Pro Lys Phe Glu Asn
465             470             475             480

Ile Ala Glu Gly Leu Arg Ala Leu Leu Ala Arg Ser His Val Glu Arg
                485             490             495

Thr Thr Asp Glu Gly Thr Trp Val Ala Gly Val Phe Val Tyr Gly Gly
                500             505             510

Ser Lys Thr Ser Leu Tyr Asn Leu Arg Arg Gly Thr Ala Leu Ala Ile
            515             520             525

Pro Gln Cys Arg Leu Thr Pro Leu Ser Arg Leu Pro Phe Gly Met Ala
530             535             540

Pro Gly Pro Gly Pro Gln Pro Gly Pro Leu Arg Glu Ser Ile Val Cys
545             550             555             560

Tyr Phe Met Val Phe Leu Gln Thr His Ile Phe Ala Glu Val Leu Lys
                565             570             575

Asp Ala Ile Lys Asp Leu Val Met Thr Lys Pro Ala Pro Thr Cys Asn
            580             585             590

Ile Arg Val Thr Val Cys Ser Phe Asp Asp Gly Val Asp Leu Pro Pro
            595             600             605

Trp Phe Pro Pro Met Val Glu Gly Ala Ala Ala Glu Gly Asp Asp Gly
            610             615             620

Asp Asp Gly Asp Glu Gly Gly Asp Gly Asp Glu Gly Glu Glu Gly Gln
625             630             635             640

Glu

<210> SEQ ID NO 23
<211> LENGTH: 18
<212> TYPE: PRT
<213> ORGANISM: HUMAN

<400> SEQUENCE: 23

Asp Pro Glu Ala Arg Arg Ala Pro Gly Ser Leu His Pro Cys Leu Ala
1               5                   10                  15

Ala Ser

<210> SEQ ID NO 24
<211> LENGTH: 24
<212> TYPE: PRT
<213> ORGANISM: MOUSE

<400> SEQUENCE: 24

Ser Glu Pro Glu Ala Arg Arg Ala Pro Gly Arg Lys Gly Gly Val Val
1               5                   10                  15

Cys Ala Ser Leu Ala Ala Asp Trp
            20
```

```
<210> SEQ ID NO 25
<211> LENGTH: 19
<212> TYPE: PRT
<213> ORGANISM: HUMAN

<400> SEQUENCE: 25

Lys Asp Pro Glu Ala Arg Arg Ala Pro Gly Ser Leu His Pro Cys Leu
1               5                   10                  15

Ala Ala Ser

<210> SEQ ID NO 26
<211> LENGTH: 11
<212> TYPE: PRT
<213> ORGANISM: HUMAN

<400> SEQUENCE: 26

Ser Asp Ser Phe Lys Ser Gln Ala Arg Gly Gln
1               5                   10

<210> SEQ ID NO 27
<211> LENGTH: 11
<212> TYPE: PRT
<213> ORGANISM: HUMAN

<400> SEQUENCE: 27

Gly Thr Pro Gly Arg Ala Glu Ala Gly Gly Gln
1               5                   10
```

1

NEURAL REGENERATION PEPTIDES AND METHODS FOR THEIR USE IN TREATMENT OF NEURAL INJURY OR DEGENERATION

CROSS-REFERENCE TO RELATED APPLICATIONS

This application claims the priority under 35 USC 119(e) to U.S. Provisional Application Ser. No. 60/314,952, filed Aug. 24, 2001, which is incorporated into this application fully by reference.

BACKGROUND

1. Field of the Invention

This invention is directed to compositions and methods for the use of peptides that promote neuronal migration, proliferation, survival and/or neurite outgrowth. More specifically, this invention is directed to the use of such peptides in the treatment of brain injury and neurodegenerative disease.

2. Related Art

Moderate to severe traumatic brain injury (TBI), and focal or global ischemia can result in significant neuronal cell loss and loss of brain function within a short time period after the insult. There are no treatments currently available to prevent cell death that occurs in the brain as a consequence of head injury or damage caused by disease. To date, there is also no treatment available to restore neuronal function. Treatments available at present for chronic neurodegenerative diseases such as Alzheimer's disease, Parkinson's disease, Hunington's disease and Multiple Sclerosis only target symptoms. No drugs are currently available to intervene in the disease process or prevent cell death.

It is well known that cortical-subcortical non-thalamic lesions lead to apoptosis within thalamic areas 3-7 days after an insult. Retrograde thalamic degeneration is accompanied by activation of astroglia and microglia in the thalamus (Hermann et al., 2000). Non-invasive techniques like MRI reveal smaller thalamic volumes and increased ventricle-to brain ratio values within TBI patients suffering from non-thalamic structural lesions (Anderson et al., 1996). These findings indicate the high vulnerability of thalamocortical excitatory projection neurons for retrograde-triggered neuronal cell death and therefore indicate the need for a rescue strategy of injured or insulted thalamic neurons.

Functioning of the inhibitory neuronal circuits within the thalamus is crucial for intrathalamic down regulation of neuronal activity within the thalamus as well as within the striatal system. It has been shown that animals with striatal lesions similar to those that occur in Huntington's disease show an improvement in behavioural outcome when GABA-releasing polymer matrices are implanted into the thalamus (Rozas et al., 1996). On a cellular level within the striatum it has been shown that calbindin immunoreactive ("calbindin-ir") inhibitory neurons can be rescued by administering activin A (Hughes et al., 1999).

Until now, only transplantation involving fetal striatal implants lead to an improvement or restoration of motor functions in Huntington's disease animal models (Nakao and Itakura, 2000). By restoring thalamic and striatal GABAergic systems that are impaired during Huntington's disease, improved behavioural outcome can be predicted (Beal et al., 1986).

A feature of the developing nervous system is the wide-ranging migration of precursor cells to their correct three-dimensional spatial position. These migrations promote differentiation of an array of phenotypes and the arrangement of immature neurons into the vertebrate brain. To achieve the correct wiring of approximately 100 billion neurons, construction of a cellular organisation like the formation of laminar structures in higher cortical regions is necessary (see Hatten and Heintz, 1999 for a review).

A cellular correlate for the direction of movement of a migrating neuron may be the frequency and amplitude of transient $Ca^{2+}$ changes within a single migrating cell (Gomez and Spitzer, 1999) although the triggering of initiation and/or commitment of neuronal cell migration by membrane-bound or diffusible molecules remains elusive.

Many of the cues that are involved in neurite outgrowth and neuronal migration, however, have been identified. Plasma membrane molecules belonging to the integrin receptor family interact with extracellular matrix ligands, like laminin, to initiate neuronal adhesion to the substratum (Liang and Crutcher, 1992; De Curtis and Reichardt, 1993). The control of integrin expression affects a wide range of developmental and cellular processes, including the regulation of gene expression, cell adhesion, neurite outgrowth and cell migration. Other ligands which promote cell migration are cell adhesion molecules (i.e. N-CAM; cadherins; TAG-1), the laminin-like molecule netrin-1, the neuron-glial adhesion ligand astrotactin and growth or neurotrophic factors such as EGF, TGF-α, platelet activating factor and BDNF (Dodd et al., 1988; Yamamoto et al, 1990; Ishii et al., 1992; Ferri and Levitt, 1995; Ganzler and Redies, 1995).

Recently, collapsin-1 (semaphorin3A) was discovered. Collapsin-1 has chemorepulsive activities in axonal guidance and migration patterns for primary sensory neurones (Pasterkamp etal., 2000). In contrast, collapsin-1 acts as a chemoattractant for guiding cortical apical dendrites in neocortical areas (Polleux et al., 2000). Similar chemorepulsive as well as chemoattractive effects on axonal guidance are displayed by slit-1, a diffusible protein (Brose et al., 2000).

Currently, the cascade leading to the initiation of neuronal movement, namely adhesion of the neurone followed by initiation of migration, the process of migration over long distances, including turns and the migration stop signal remains to be elucidated.

Midbrain lesions with simultaneously administered TGF-α lead to a massive proliferation of multipotential stem cells originating in the subventricular zone ("SVZ") and subsequent migration of these progenitor cells into the striatum (Fallon et al., 2000). It may be desirable, however, to activate neuronal proliferation and migration of neurons that are in close vicinity to the site of a lesion in order to prevent long-distance migration of neuronal precursors originating from the SVZ.

There is only one report featuring the chemokine stromal-derived factor (SDF-1) as a neuronal migration chemoattractant. The embryonic expression pattern of SDF-1 attracts cerebellar granule cells to migrate from the external germinal layer to the internal granular layer (Zhu et al., 2002). Nevertheless, this chemokine has no influence on postnatal tissue. There are no known migration-inducing factors that have direct chemoattractive effects on the migration behaviour of neuroblasts or neurons in adults after brain trauma or neurodegenerative disease.

SUMMARY OF THE INVENTION

It is therefore an object of embodiments of the present invention to provide new approaches to the treatment of brain injuries and diseases. Such embodiments include administering one or more migration-, survival-outgrowth-and/or pro-liferation-inducing factors to promote neuronal or neuroblast migration and/or proliferation into regions of tissue damage following brain injury or during chronic neurodegenerative disease. Such therapeutic improvement can be achieved by administering one or more peptides, herein termed neural regeneration peptides ("NRPs"). NRPs include homologs, paralogs and/or analogs (together, termed "NRP compounds"). An NRP compound can either be administered alone or in conjunction with one or more other NRP compounds or with other types of agents to promote neural outgrowth, neural migration, neural survival and/or neural proliferation.

NRPs and related peptides generally have certain amino acid sequences present, which confer desirable biological properties on the molecule.

Some embodiments of NRP peptides are shown in Table 1 below.

domain. Still other NRPs can have a [A]PG[R,S] domain, an [A,G]RR domain and a PE domain.

NRP family members contain at least a CAAT-Box or a TATA-Box, or both in promoter regions.

In another aspect, embodiments of this invention provide methods of treatment for damaged areas of the brain as a consequence of head injury or chronic neurodegenerative disease by administering one or more NRPs, NRP analogs (including peptides with structural similarities) and/or NRP prodrugs (including pro-NRP peptides) to promote neuronal or neuroblast migration, proliferation, survival and/or neurite outgrowth. This method of treatment may be particularly useful but in no way limited to, patients suffering from moderate to severe traumatic brain injury (TBI) that involves neocortical damage as well as injuries to subcortical areas.

TABLE 1

Neural Regeneration Peptides*

```
NRP-1:  Y D P E A A S - A P G S G N P - - - - - - C H
NRP-2:  K D P E A R R - A P G S L H P - - - - - - C - - L A A - S C S A A G
NRP-3:  S D S F K S Q - A R G Q V P P F L G G V G C P W F
NRP-4:  G T P G R A E - A G G Q V S P - - - - - - C - - L A A - S C S Q A Y G
NRP-5:  R E - - G R R D A P G R A - - G G G G - - - - - - A A R S S P S P
NRP-7:  S E P E A R R - A P G R K - - - - G G V V C A S L A A D W
NRP-8:  S E V D A R R - A K K S L H - - - - - - - C - I L S - D T S H P R G
```

*NRP-2: NRP human chromosome 13
 NRP-3: NRP human chromosome  3
 NRP-4: NRP human chromosome 15
 NRP-5: NRP human chromosome  7
 NRP-7: NRP mouse frameshift
 NRP-8: NRP mouse ortholog    2

In some embodiments, NRPs generally comprise a chain length of between about 8 to about 25 amino acids and having molecular weights between about 0.8 and about 2.7 kDa. Additionally, in other embodiments, an NRP can have an isoelectric point between about 6.5 and about 10.0, and having at least one biological property promoting an outcome selected from neuronal survival, neurite outgrowth, neuronal proliferative and neuronal migration. Additionally, an NRP may have one or more domains, as indicated in bold in Table 1 above. In some embodiments, an NRP may have a [A]PG [R,S] domain in combination with a PE-domain (e.g., NRP-1 and NRP-2), or alternatively, without a PE-domain (e.g., NRP-5, NRP-7). The presence of a [A]PG[R,S] domain is desirable for NRP biological activity. Thus, in alternative embodiments, NRPs can have a first domain selected from the group consisting of a [A]PG[R,S] domain, an [A,G]RR domain and an ARG domain have desirable biological activity. In other embodiments, desirably, an NRP can have, in addition to a first domain as described above, a second domain different from the first domain. A second domain can be a PE domain or an [A,G]RR domain. In certain further embodiments, NRP s can have a third domain of those described above.

Thus, in certain embodiments, NRPs have a [A]PG[R,S] domain alone, other NRP can have an ARG domain alone, still other NRPs can have an [G,A]RR domain alone. Still other NRPs have a [A]PG[R,S] domain and a PE domain, and still other NRP have a [A]PG[R,S] domain and a [G,A]RR In one embodiment, NRP-2 is encoded by a nucleic acid sequence localised on human chromosome 13 within the genomic clone bA87G1 (Sanger Sequencing Centre) on the reverse strand between base pairs 77232-76768. This peptide has functions similar to those of rat NRP-1 concerning the regulation of neuronal proliferation and migration-induction as well as neurite outgrowth and neuronal survival-promoting activities.

In another embodiment, NRP-3 is encoded by a nucleic acid sequence localized on the reverse strand of chromosome 3 in the human genome, between base pairs 34764-33003 according to DoubleTwist annotation. This NRP also exhibits neuronal survival-promoting and proliferative activities, as well as migration inducing and neurite outgrowth activity.

Still another embodiment, NRP-4 is encoded by a nucleic acid sequence located between base pairs 21970003-21972239 on the forward strand of human chromosome 15, according to the NCBI human genome annotation project. Peptides translated from that nucleic acid sequence also belong to the human gene family of NRPs. Peptides encoded by this sequence exhibits neurite outgrowth and survival-promoting functions as well as neuronal migration and proliferation-inducing properties.

A still further embodiment includes NRP-5, which is encoded by a nucleic acid sequence localized on the reverse strand of human chromosome 7, in the region between base pairs 15047153-14824042, as denoted by the NCBI annotation. Peptides encoded by this sequence demonstrate neuronal survival-promoting functions, as well as proliferation-inducing activity, neurite outgrowth stimulation and migration inducing properties.

Another embodiment of an NRP has been annotated, with a DNA sequence from the human genome located in the region 116668725-116667697 on the reverse strand of chromosome 6 (region according to NCBI human genome annotation project). The resulting peptide induces neuronal proliferation and migration, —as well as neurite outgrowth and survival.

Yet further embodiments of NRPs are found in rodents. One mouse NRP is encoded by a nucleic acid sequence located within the arachne contig__191157 of NCBI consisting of 339 nucleic acids using reading frame 1. Within an overlapping region, there is a second ORF of 198 nucleic acids starting at position 29 of an annotated NRP using frame 3. This ORF codes for a protein with high identity to a truncated human DNA repair protein. The resulting peptide NRP-7 induces neuronal proliferation and migration, neurite outgrowth and neuronal survival.

A still further embodiment includes NRP-8, which is also a mouse peptide, and is encoded by a nucleic acid sequence located within the genomic clone bM344E9 of the mouse Sanger database on the reverse strand. The protein coding sequence has been annotated and is located between base pairs 5609-4052. This peptide can increase neuronal proliferation and migration as well as neurite outgrowth and neuronal survival.

In another aspect, the invention includes embodiments for in vitro bioassays for evaluating proliferative and migration-inducing activity. Until recently, there were few in vitro neuronal migration assays available that could detect migrating untagged neurons over a prolonged time-period. One of these bioassays monitors olfactory peripheric placode cells organized as OTCs during a 5 day time course (Fueshko and Wray, 1994). In certain embodiments of this invention, by using in vitro bioassay using adult thalamocortical organotypic tissue cultures "OTCs," putative NRPs can be evaluated for their ability to induce migration, proliferation, survival and/or neurite outgrowth. These embodiments can be particularly useful because 1) under control conditions, formation of a cell-bridge between both cultivated organs (e.g., thalamus and cortex) can be avoided by physically separating the two organs sufficiently far from each other (about 3 to about 5mm) on a tissue culture substrate and 2) because after birth, intrathalamic neuronal migration has been substantially completed due to the time course of thalamic ontogenesis. These bioassays can therefore be well suited for broad screening and identification of neuronal migration-inducing factors.

In certain embodiments of an in vitro assay, the thalamo-cortical OTC assay, includes the advantages of revealing both kind of neuronal migration, namely radial migration within the cortex and the induced tangential migration within the thalamus. Under in vitro control conditions only intrinsic cortical radial migration can be observed that due to the time course of the ontogenetic development of the neocortex.

In other embodiments, in vitro bioassays are provided that involve cerebellar microexplants adhered to substrates. These embodiments can be used to provide data regarding patterns of neuronal migration, including quantifying the numbers of migrating neurons and the distance of migration in respect of the microexplant.

A developing migration-chain consisting of small neurons (such as inhibitory granule cells) as well as an overall enhancement of cell migration can be observed after as little as 2-3 days of cultivation. This assay result resembles the cell chain induction within thalamocortical OTCs.

Embodiments of another aspect of the invention include the use of NRPs to treat neurodegenerative diseases and brain injuries. In particular, NRPs are particularly suitable for use in brain regions lacking quiescent neuronal stem cells near the area of injury or disease.

NRP compounds are capable of initiating neuronal proliferation, migration, survival and neurite outgrowth within postnatally differentiated neural tissue. These properties can be exploited in treatment strategies aimed at improving or repairing neuronal circuits within impaired areas of patients with moderate to severe TBI, including diffuse axonal injury, hypoxic-ischemic encephalopathy and other forms of craniocerebral trauma. NRP compounds can be used to treat infections of the nervous system, such as common bacterial meningitis, and to treat common causes of strokes including, ischemic infarction, embolism, and haemorrhage such as hypotensive haemorrhage. Moreover, NRP compounds can be useful for the treatment of neurodegenerative diseases including Alzheimer's Disease, Lewy Body Dementia, Parkinson's disease (PD), Huntington's disease (HD), metabolic disorders of the nervous system including glycogen storage diseases, and other conditions where neurons are damaged or destroyed.

BRIEF DESCRIPTION OF THE FIGURES

The patent or application file contains at least one drawing executed in color. Copies of this patent or patent application with color drawings will be provided by the Office upon request and payment of the necessary fee. This invention will be described by way of description of particular embodiments thereof. Other objects, features and advantages of embodiments of this invention will become apparent from the specification and the figures, in which:

FIG. 3A shows an overview of two migrating cell chains. The upper neuronal cell chain had completed its way to the cortex while the lower one had reached half way to the cortical tissue. The neuronal origin of the cell chain was verified by the MAP-2 expression pattern of the migrating cells, as shown in FIGS. 3B to 3D. Double arrows in A/B point to the same location. In FIGS. 3C and 3D, the micrograph of the migrating cell chain was taken near the cortical tissue. Bars: 500 μm (FIG. 3A); 100 μm (FIGS. 3B to 3D).

In FIG. 4D the onset of migration of thalamic cells can be observed. The black arrows indicate nuclei while the white arrows point to the leading process of the migrating cells. Bars: 500 μm (FIGS. 4A and 4B); 100 μm (FIG. 4C); 80 μm (FIG. 4D).

FIG. 7A shows that two thalamocortical connections (arrows) have been established revealing MAP2-positive cells. The square indicates the greater magnification shown in FIG. 7B. FIG. 7B shows the cell stream having bipolar-shaped parvalbumin-positive neurons migrating in a track-like arrangement. FIG. 7C shows MAP-2-positive neurons close to the origin of the thalamic cell stream. The cell stream is characterized by highly ordered positioning of the neuronal soma. The primary neurites project to the axonal layer in the middle of the cell-bridge (small arrows). FIG. 7D shows BrdU-positive proliferating cells (arrows) located in the habenula, the generated thalamocortical cell bridge, and within cortical layers. The circles indicate regions of high proliferation. FIG. 7E shows BrdU-positive cells within the cell-bridge. A subpopulation (arrows) is co-localised with parvalbumin (arrows in FIG. 7F). Bars: 500 μm (FIGS. 7A and 7D); 100 μm (FIGS. 7B, 7E and 7F); 50 μm (FIG. 7C).

FIG. 9A shows a confocal image revealing that the migrating cell stream contains proliferating neuronal cells positive for parvalbumin and BrdU (indicated by thick white arrows). Some neurons are only positive for parvalbumin (thin arrows). The long white arrow points to the location of the thalamic tissue. FIGS. 9B and 9C show that most of parvalbumin-ir cells (FIG. 9B) within the migrating stream are of proliferating character (FIG. 9C; arrows). Note the immunoreactivity of the fibres once again confirming that the Neurons "travel" along neuronal fibres. Bars: 100 μm (FIG. 9A); 50 μm (FIGS. 9B and 9C).

In FIG. 11D there was a migrated calretinin/BrdU-positive cell near the cortical layer VI indicated. Bar: 50 μm.

FIG. 12A depicts non-proliferative GFAP-positive astrocytes (white arrows) accompanying the neuronal migration stream with only a subpopulation of astrocytes of proliferative character (FIG. 12B; white arrow heads). Approximately 30% of the astrocytes in close vicinity to the neuronal migration stream were of proliferative character. Bar: 50 μm.

FIG. 14A shows that there was massive migration of mostly small cells (10-15 μm in diameter) and neurite outgrowth originating from the microexplant. Migrating cells over 15 μm in diameter are indicated by arrowheads. Small inhibitory neurons migrate as a migrating cell stream (FIGS. 14A, 14B and 14C) or more or less loosely arranged on a neuritic network (FIG. 14D) interconnecting microexplants. Within FIGS. 14E and 14F MAP-2 expression is shown. Arrows in FIG. 14F indicate migrating neurons.

DETAILED DESCRIPTION

Definitions

Figure 1:
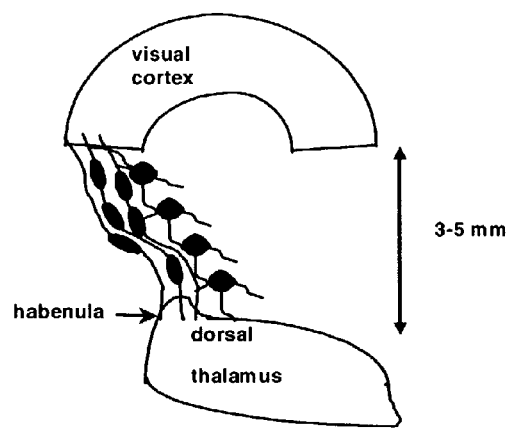
FIG. 1 is a depiction of an arrangement of an in vitro bioassay of this invention, comprising thalamocortical co-cultures on a substrate and the subsequent generation of a thalamic cell bridge after 3-4 days of exposure to purified NRP-1. There was a preference for migration induction within the habenula nucleus a part of the limbic system within the dorsal thalamus.

The term "homolog" includes one or more genes whose gene sequences are significantly related because of an evolutionary relationship, either between species (ortholog) or within a species (paralog). Homolog also includes genes related by descent from a common ancestral DNA sequence. Homolog also includes a relationship between genes separated by a speciation event, or to a relationship between genes by the event of genetic duplication (see paralog). As used herein, the term "homolog" also includes gene products related to each other by way of an evolutionary relationship. NRPs having conserved amino acid sequence domains are examples of homologs.

The term "paralog" includes one of a set of homologous genes that have diverged from each other as a consequence of genetic duplication. For example, the mouse alpha globin and beta globin genes are paralogs. As used herein, the term "paralog" also includes gene products related to each other by way of an evolutionary relationship. Human NRPs having conserved amino acid sequence domains are examples of paralogs.

The term "ortholog" includes one of a set of homologous genes that have diverged from each other as a consequence of speciation. For example, the alpha globin genes of mouse and chick are orthologs. As used herein, the term "ortholog" also includes gene products related to each other by way of an evolutionary relationship. Human and mouse NRPs having conserved amino acid sequence domains are examples of homologs.

The term "paralog peptide" includes a peptide encoded by a paralog nucleotide sequence.

The term "peptide" and "protein" include polymers made of amino acids.

The term "prodrug" includes molecules, including pro-peptides which, following enzymatic, metabolic or other processing, result in an active NRP, an active NRP analog or a NRP paralog.

The term "NRP compound" includes NRPs, NRP homologs, NRP paralogs, NRP orthologs, NRP analogs, and prodrugs of NRP.

The term "NRP" includes neuronal regeneration peptides having functions including neural or neuroblast migration, proliferation, survival and/or neurite outgrowth, regardless of evolutionary relationship.

Amino acids are represented by the standard symbols where alanine is represented by "A" or "Ala", arginine by "R" or "Arg", asparagine by "N" or "Asn", aspartic acid by "D" or "Asp", cysteine by "C" or "Cys", glutamic acid by "E" or "Glu", glutamine by "Q" or "Gln", glycine by "G" or "Gly", Due to the degeneracy of the genetic code, however, multiple codons may encode the same amino acid. Thus, various nucleic acid sequences may encode for the same amino acid sequence. Each of these variations can be translated into SEQ ID NO: 2, and thus, all of these variations are included within the scope of this invention. For example, multiple nucleic acid sequences, including the nucleic acid sequence listed in SEQ ID NO: 1, encode for the rat NRP-1 amino acid sequence. The invention further comprises variants of the nucleotide sequence of SEQ ID NO: 1, including variants which preserve the amino acid sequence encoded by the nucleic acid sequences, as well as nucleic acid sequences which encode for rat NRP-1 analogs and NRP-1 orthologs and/or paralogs. By way of example only, variants of SEQ ID NO: 1 according to the genetic code for DNA are listed below, with each codon separated by a space from neighbouring codons, and where a nucleic acid following a "/" is a variant for the nucleic acid preceding the "/":

```
5' tat/c gat/c cca/t/c/g gag/a gcc/g/a/t gcc/g/a/t tct/a/c/g gcc/g/a/t cca/t/c/g gga/t/c/g tcg/a/t/c
ggg/a/t/c aac/t cct/a/c/g tgc/t cat/c 3'
``` histidine by "H" or "His", isoleucine by "I" or "Ile", leucine by "L" or "Leu", lysine by "K" or "Lys", methionine by "M" or "Met", phenylalanine by "F" or "Phe", proline by "P" or The above sequence, including the indicated variants, may be written using the letters r, y and n as defined above to provide the following sequence:

```
5' tay gay ccn gar gcn gcn tcn gcn ccn ggn tcn ggn aay ccn tgy cay 3'    SEQ ID NO: 3
```

"Pro", serine by "S" or "Ser", threonine by "T" or "Thr", tryptophan by "W" or "Trp", tyrosine by "Y" or "Tyr", and valine by "V" or "Val".

Nucleic acids comprise nucleotides including adenine, which is represented by "a";

thymine, which is represented by "t"; cytosine, which is represented by "c" and guanine, which is represented by "g." A nucleotide which can be either guanine or adenine is represented by "r", a nucleotide which can be either thymine or cytosine is represented by "y" and a nucleotide which can be either guanine, adenine, cytosine, or thymine is represented by "n". Polynucleotides may be DNA or RNA, and may be either single stranded or double stranded. Where the polynucleotide is a RNA polynucleotide, uracil "u" may be substituted for thymine.

Description of Specific Embodiments

Embodiments of this invention include compositions and methods for the treatment of brain damage, encompassing a neuronal migration-inducing, neurite outgrowth and proliferation-promoting factor (NRPs, NRP analogs and/or NRP prodrugs, and peptides encoded by NRP paralogs, including human and mouse paralogs, homologs and orthologs).

The nucleotide sequence (SEQ ID NO: 1) and amino acid sequence (SEQ ID NO: 2) of rat NRP-1 are:

It will be understood that other nucleotide sequences encoding other NRPs can vary according to the redundancy of the genetic code. Moreover, RNA as well as DNA may encode the peptides of the invention, and that where a nucleic acid is a RNA nucleic acid, uracil may be substituted for thymine.

A human gene was annotated using the human cachexia cDNA (U.S. Pat. No. 5,834,192) as a template. A survival-promoting peptide has more than 96% identity to a survival-promoting peptide (Cunningham et al., 1998) and rat NRP-1 has 100% identity to the cachexia proetin and is the only NRP-1 homologue with known respective cDNA. Human cachexia protein is localised on chromosome 12 within the region of base pairs 621841-625428 and consists of 5 exons. We have compared the cachexia mRNA splice sites with the identified NRP human paralog on chromosome 13 (genomic clone from the Sanger Sequencing Centre—bA87G1: base pairs 77232-76768) and have annotated the coding region of a NRP-1 human ortholog (this ortholog is herein termed NRP-2). The nucleotide and amino acid sequences relating to NRP-2 are:

```
           9         18        27        36        45
5' tat gat cca gag gcc gcc tct gcc cca gga tcg ggg aac cct tgc cat 3'    SEQ ID NO: 1

Tyr Asp Pro Glu Ala Ala Ser Ala Pro Gly Ser Gly Asn Pro Cys His        SEQ ID NO: 2
```

| SEQ ID NOs: 4 and 5 | | | | | | | | | | | |
|---|---|---|---|---|---|---|---|---|---|---|---|
| | | 9 | | | 18 | | | 27 | | | 36 |
| 5' atg | aga | gtc | aga | gta | caa | ctc | aag | tct | aat | gtc | caa gtt gga SEQ ID NO: 4 |
| Met | Arg | Val | Arg | Val | Gln | Leu | Lys | Ser | Asn | Val | Gln Val Gly SEQ ID NO: 5 |
| 45 | | | 54 | | | 63 | | | 72 | | 81 |
| gca | gga | cac | tca | gca | aag | gat | cca | gag | gca | agg | aga gca cct |
| Ala | Gly | His | Ser | Ala | Lys | Asp | Pro | Glu | Ala | Arg | Arg Ala Pro |
| | | 90 | | | 99 | | | 108 | | | 117 | 126 |
| gga | agc | cta | cat | ccc | tgt | cta | gca | gca | tca | tgc | tca gct gct |
| Gly | Ser | Leu | His | Pro | Cys | Leu | Ala | Ala | Ser | Cys | Ser Ala Ala |
| | | | 135 | | | 144 | | | 153 | | 162 |
| ggc | ctg | cac | aca | agc | tcg | tgg | aag | aac | ctg | ttt | ttg ata gaa |
| Gly | Leu | His | Thr | Ser | Ser | Trp | Lys | Asn | Leu | Phe | Trp Ile Glu |
| 171 | | | 180 | | | 189 | | | 198 | | 207 |
| gga | cta | gta | agt | att | tgc | cta | ggg | cac | ata | gtt | gta caa gag |
| Gly | Leu | Val | Ser | Ile | Cys | Leu | Gly | His | Ile | Val | Val Gln Glu |
| | | 216 | | | 225 | | | 234 | | | 243 | 252 |
| acg | gac | gtt | ttt | agg | tcc | ttg | cgg | ttt | ctt | gca | ttt cca gaa |
| Thr | Asp | Val | Phe | Arg | Ser | Leu | Arg | Phe | Leu | Ala | Phe Pro Glu |
| | | 261 | | | 270 | | | 279 | | | 288 |
| aac | ttg | ctt | caa | ata | ttt | ttc | cag | atg | caa | aat | tcc ttg gat |
| Asn | Leu | Leu | Gln | Ile | Phe | Phe | Gln | Met | Gln | Asn | Ser Leu Asp |
| 297 | | | 306 | | | 315 | | | 324 | | 330 |
| cct | tgt | ttt | aga | atg | aat | cta | tta | aaa | act | tca | cat taa 3' |
| Pro | Cys | Phe | Arg | Met | Asn | Leu | Leu | Lys | Thr | Ser | His *stop |

The underlined nucleotide sequence denotes the signal peptide.

Figure 16:
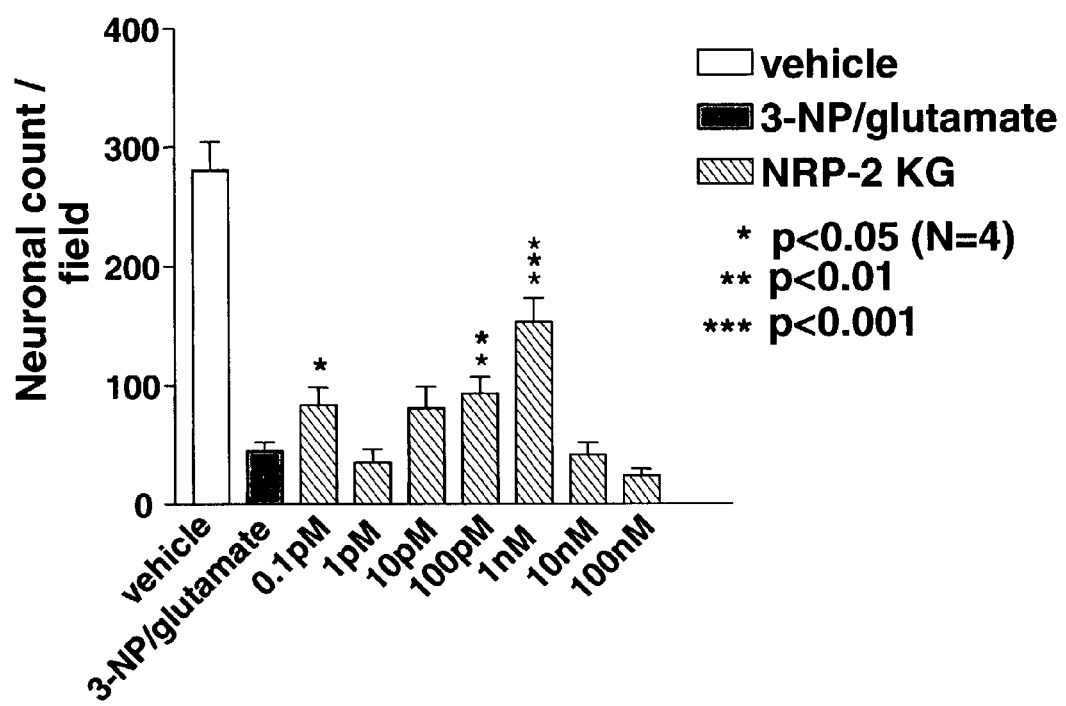
FIG. 16 depicts results of a survival assay with NRP-2 segment KG. Cerebellar microexplants were injured by 3-NP/glutamate and simultaneously rescued by NRP-2 segment KG. After 48 hrs neuronal survival was evaluated by counting cells displaying neurite outgrowth. The maximal biological activity for survival of NRP-2 segment KG within simultaneously applied injury lies between 100 pM and 1 nM.
Figure 17:
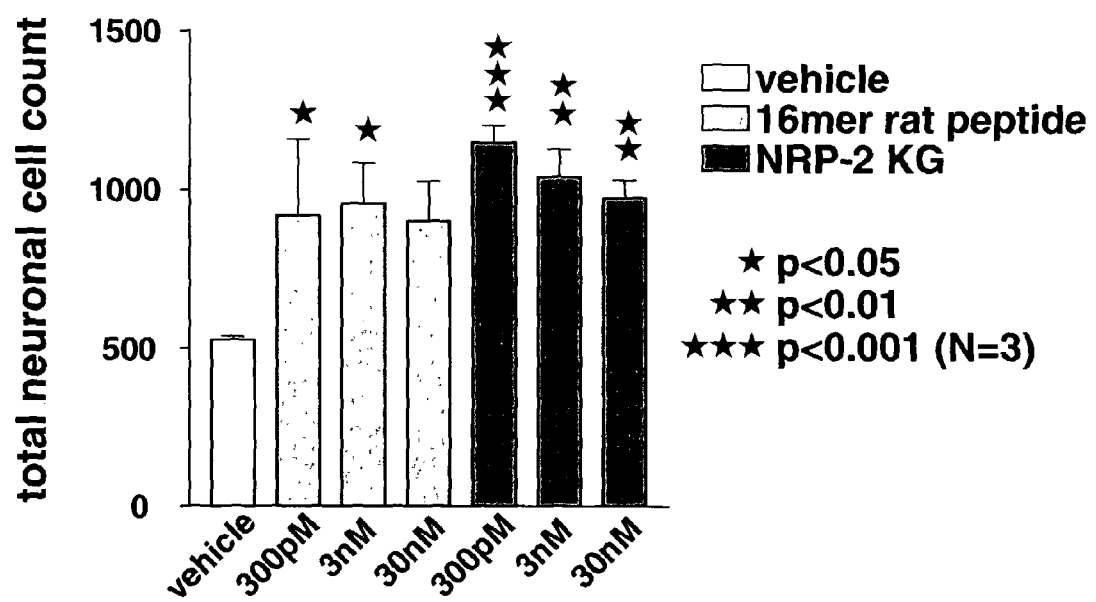
FIG. 17 depicts results of proliferation induction without injury using NRP-2 segment KG and rat NRP-1. Peptides were administered 24 hrs after start of cultivation to decrease interference in the assay due to initial neuronal survival or adherence effects. The cultures were fixed after 3 days in vitro. There was massive neuronal proliferation seen at 300 pM of NRP-2 segment KG.
Figure 18:
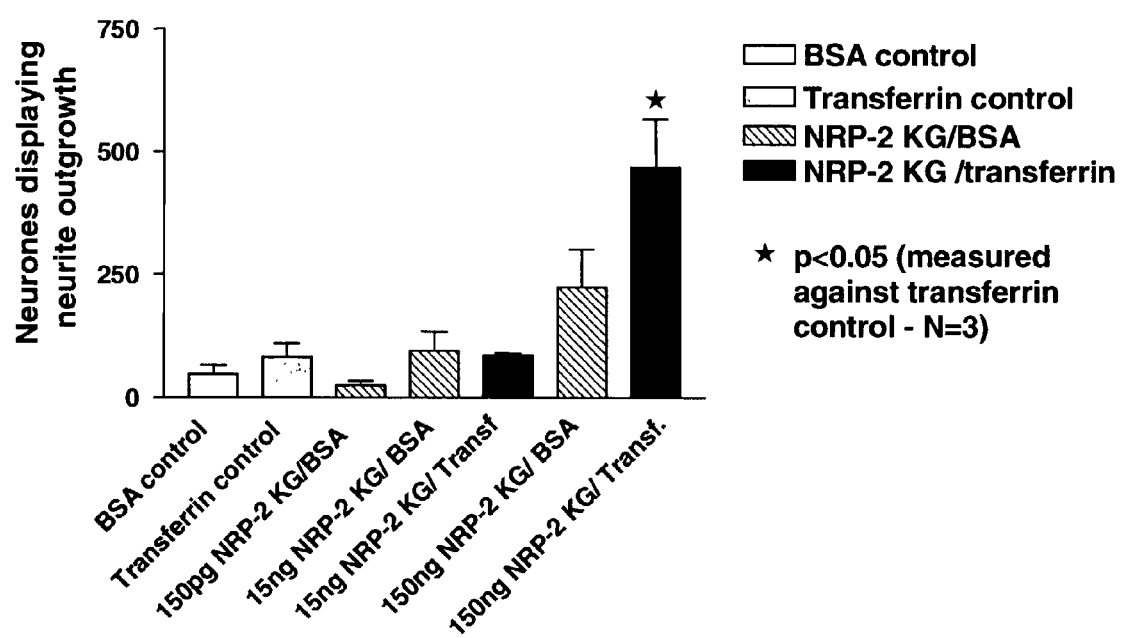
FIG. 18 depicts results of a haptotactic migration assay using NRP-2 segment KS. The NRP-2 segment KS (0.0 μg/ml and 0.1 μg/ml) was diluted in 1.0 μg/ml BSA or 10 μg/ml human transferrin, respectively. The coated NRP-2 segment KS was subsequently followed by 100 μg/ml PDL coating. Striatal cells were seeded into PDL-coated inserts and migration behaviour was measured after 48 hrs. There was massive migration induction of striatal neurons when culture dishes were coated with 150 ng of NRP 2 segment KS.

The protein coding DNA sequence consists of 4 exons as predicted by splice site analysis taking the sequence of the paralog form of the human cachexia gene (cDNA from U.S. Pat. No. 5,834,192) on chromosome 12 as a template. The chromosome map of the genomic clone bA87G1 is considered as the basis for the exact exon localisation. Exon 1 is located between bp 77232-77170. Exon 2 is located between bp 77088-77046. Exon 3 is located between bp 77036-76824. Exon 4 is located between base pairs 76778-76768 followed by the translation stop codon TAA. The translated protein consists of 110 amino acids, is identical in length to the human cachexia protein, and has 24.5% overall identity to human cachexia protein. Sequence comparison of the signal peptides for extracellular localisation (amino acids 1-19) of both proteins reveals 31.6% identity. Significantly, comparison of the first 30 amino acids of the mature (cleaved) peptide reveals 46.7% amino acid identity. Furthermore this peptide has similar neuronal migration, proliferation, survival and neurite outgrowth activities as NRP-1 (see FIGS. 16, 17 and 18).

A second ortholog of NRP-1 has been annotated, and is encoded by a DNA sequence from the human genome located between the base pairs 34764-33003 on the reverse complement strand of chromosome 3 (region according the Double Twist human genome annotation project). The protein coding sequence consists of 5 exons with the following locations: exon 1: 34764-34743; exon 2: 34729-34700; exon 3: 33745-33596; exon 4: 33498-33459; exon 5: 33043-33003. The nucleotide sequence (SEQ ID NO: 6) has 333 nucleotides and the amino acid sequence (SEQ ID NO: 7; herein termed NRP-3) has 111 amino acids, as denoted below.

| SEQ ID NOs: 6 and 7 | | | | | | | | | | | |
|---|---|---|---|---|---|---|---|---|---|---|---|
| | | 9 | | | 18 | | | 27 | | | 36 |
| 5' atg | aaa | ata | aat | gta | tta | att | aaa | tta | atg | acc | aag tca gat SEQ ID NO: 6 |
| Met | Lys | Ile | Asn | Val | Leu | Ile | Lys | Leu | Met | Thr | Lys Ser Asp SEQ ID NO: 7 |
| 45 | | | 54 | | | 63 | | | 72 | | 81 |
| tct | ttt | aaa | agc | caa | gcc | agg | ggc | caa | gtt | ccc | cca ttt cta |
| Ser | Phe | Lys | Ser | Gln | Ala | Arg | Gly | Gln | Val | Pro | Pro Phe Leu |
| | | 90 | | | 99 | | | 108 | | | 117 | 126 |
| ggg | ggg | gtg | ggg | tgc | ccc | tgg | ttt | ttt | caa | aca | agg ttt tgg |
| Gly | Gly | Val | Gly | Cys | Pro | Trp | Phe | Phe | Gln | Thr | Arg Phe Trp |
| | | | 135 | | | 144 | | | 153 | | 162 |
| ggc | cat | agt | ttt | gca | gtt | aaa | ctg | gcc | tcc | aac | ctt tcc cag |
| Gly | His | Ser | Phe | Ala | Val | Lys | Leu | Ala | Ser | Asn | Leu Ser Gln |

-continued

SEQ ID NOs: 6 and 7

```
       171         180         189         198         207
       gca gag aaa ttg gtc ctt cag caa acc ctt tcc caa aaa ggc
       Ala Glu Lys Leu Val Leu Gln Gln Thr Leu Ser Gln Lys Gly 216         225         234         243         252
       cta gac gga gca aaa aaa gct gtg ggg gga ctc gga aaa cta
       Leu Asp Gly Ala Lys Lys Ala Val Gly Gly Leu Gly Lys Leu 261         270         279         288
       gga aaa gat gca gtc gaa gat cta gaa agc gtg ggt aaa gga
       Gly Lys Asp Ala Val Glu Asp Leu Glu Ser Val Gly Lys Gly 297         306         315         324         333
       gcc gtc cat gac gtt aaa gac gtc ctt gac tca gta cta tag 3'
       Ala Val His Asp Val Lys Asp Val Leu Asp Ser Val Leu *stop
```

This sequence belongs to the human gene family of NRP's, and it is herein termed NRP-3. The sequence has 50% identity and 62.7% similarity to the human cachexia-associated protein. Furthermore, the peptide encoded by this nucleotide sequence has similar properties to NRP-1.

A third NRP-1 ortholog has been annotated is contained in the DNA sequence from the human genome located between the region 21970003-21972239 on the forward strand of human chromosome 15 (region according NCBI human genome annotation project). The protein coding sequence consists of 6 exons with the following locations: exon 1: 21970003-21970031; exon 2: 21970515-21970545; exon 3: 21970571-21970644; exon 4: 21970818-21970861; exon 5: 21971526-21971731; exon 6: 21972189-21972239. The sequence consists of 435 nucleic acids that encode 145 amino acids. The nucleotide sequence (SEQ ID NO: 8) and amino acid sequence (SEQ ID NO: 9; herein termed NRP-4) are:

SEQ ID NO: 8 and 9

```
                 9          18          27          36
    5' atg gct gtt gtg tta ctt gca cca ttt ggg gac atc agc cag  SEQ ID NO: 8
       Met Ala Val Val Leu Leu Ala Pro Phe Gly Asp Ile Ser Gln  SEQ ID NO: 9

45          54          63          72          81
       gaa atc aca aag gtt ggg aca ggg act cca ggg agg gct gag
       Glu Ile Thr Lys Val Gly Thr Gly Thr Pro Gly Arg Ala Glu 90          99         108         117         126
       gcc ggg ggc cag gtg tct cca tgc ctg gcg gcg tcc tgc agt
       Ala Gly Gly Gln Val Ser Pro Cys Leu Ala Ala Ser Cys Ser 135         144         153         162
       cag gcc tat ggc gcc atc ttg gct cac tgc aac ctc tgc ctc
       Gln Ala Tyr Gly Ala Ile Leu Ala His Cys Asn Leu Cys Leu 171         180         189         198         207
       cca ggt tca atg att aaa aaa aag aag aaa ttt ata gtt gaa
       Pro Gly Ser Met Ile Lys Lys Lys Lys Lys Phe Ile Val Glu 216         225         234         243         252
       ata gaa agt caa cct tta aag tct tac agg gaa aat tct acc
       Ile Glu Ser Gln Pro Leu Lys Ser Tyr Arg Glu Asn Ser Thr 261         270         279         288
       cat ttt ccc aga cca gtc cta aat ctt atg cga aaa cac tgt
       His Phe Pro Arg Gly Val Leu Asn Leu Met Arg Lys His Cys 297         306         315         324         333
       ggg gaa aag ggg gaa gaa ggg cct tgt ttc tct ccc aag caa
       Gly Glu Lys Gly Glu Glu Gly Pro Cys Phe Ser Pro Lys Gln 342         351         360         369         378
       atg ggg gag agg cga gnn tgt ggc gga ggg cta ggg ttg gct
       Met Gly Glu Arg Arg XXX Cys Gly Gly Gly Leu Gly Leu Ala 387         396         405         414
       cgc gag atc act aat tta aca tcc gct cat ctg ttg gtc ttg
       Arg Glu Ile Thr Asn Leu Thr Ser Ala His Leu Leu Val Leu
```

SEQ ID NO: 8 and 9

```
423              432 435
aat atc agc aac cag tga 3'
Asn Ile Ser Asn Gln *stop
```

This sequence belongs to the human gene family NRP's. This sequence has 45% amino acid similarity to the NRP encoded by a nucleic acid sequence located on human chromosome 13. Triplet 244-246 (amino acid position 82); triplet 391-393 (amino acid position 131) and triplet 421-423 (amino acid position 141) encode potential N-glycosylation sites. Amino acid position 118 has an x because of uncertainty within the nucleic acid sequence. The peptide, NRP-4, exhibits neural proliferation promoting activity, neurite outgrowth and neuronal survival promoting activities.

Another human ortholog ("NRP-5") of rat NRP-1 is encoded by the DNA sequence located within the *Homo sapiens* chromosome 7 working draft (NCBI: ref/NT_007933.9/Hs7_8090) of the NCBI database on the reverse strand. The protein coding sequence has been annotated and consists of 3 exons with 798 nucleic acids in total length coding for 266 amino acids. The exact locations for the protein coding exons are the following: exon 1: 15047153-15046815; exon 2: 14897885-14897772; exon 3: 14824386-14824042. There exists evidence from a human EST (GenBank AW138864) that the mRNA is expressed. The nucleotide sequence (SEQ ID NO: 10) and the amino acid sequence (SEQ ID NO: 11; NRP-5) are as follows:

SEQ ID NOs: 10 and 11

```
                9              18             27             36
5' atg ctg gac ccg tat tcc agc gaa gag gag tcg gac gag ggg        SEQ ID NO: 10
   Met Leu Asp Pro Ser Ser Ser Glu Glu Glu Ser Asp Glu Gly        SEQ ID NO: 11

45             54             63             72             81
   ctg gaa gag gaa agc cgc gat gtg ctg gtg gca gcc ggc agc
   Leu Glu Glu Glu Ser Arg Asp Val Leu Val Ala Ala Gly Ser 90             99            108            117            126
   tcg cag cga gct cct cca gcc ccg act cgg gaa ggg cgg cgg
   Ser Gln Arg Ala Pro Pro Ala Pro Thr Arg Glu Gly Arg Arg 135            144            153            162
   gac gcg ccg ggg cgc gcg ggc ggc ggc gcg gcc aga tct
   Asp Ala Pro Gly Arg Ala Gly Gly Gly Ala Ala Arg Ser 171            180            189            198            207
   gtg agc ccg agc ccc tct gtg ctc agc gag ggg cga gac gag
   Val Ser Pro Ser Pro Ser Val Leu Ser Glu Gly Arg Asp Glu 216            225            234            243            252
   ccc cag cgg cag ctg gac cat gag cag gag cgg agg ata cgc
   Pro Gln Arg Gln Leu Asp Asp Glu Gln Glu Arg Arg Ile Arg 261            270            279            288
   ctg cag ctc tac gtc ttc gtc gtg agg tgc atc gcg tac ccc
   Leu Gln Leu Tyr Val Phe Val Val Arg Cys Ile Ala Tyr Pro 297            306            315            324            333
   ttc aac gcc aag cag ccc acc gac atg gcc cgg agg cag cag
   Phe Asn Ala Lys Gln Pro Thr Asp Met Ala Arg Arg Gln Gln 342            351            360            369            378
   aag ctt aac aaa caa cag ttg cag tta ctg aaa gaa cgg ttc
   Lys Leu Asn Lys Gln Gln Leu Gln Leu Leu Lys Glu Arg Phe 387            396            405            414
   cag gcc ttc ctc aat ggg gaa acc caa att gta gct gac gaa
   Gln Ala Phe Leu Asn Gly Glu Thr Gln Ile Val Ala Asp Glu 423            432            441            450            459
   gca ttt tgc aac gca gtt cgg agt tat tat gag gtt ttt cta
   Ala Phe Cys Asn Ala Val Arg Ser Tyr Tyr Glu Val Phe Leu 468            477            486            495
   aag agt gac cga gtg gcc aga atg gta cag agt gga ggg tgt
   Lys Ser Asp Arg Val Ala Arg Met Val Gln Ser Gly Gly Cys 504            513            522            531            540
   tct gct aag gac ttc aga gaa gta ttt aag aaa aac ata gaa
```

| SEQ ID NOs: 10 and 11 |
|---|
| Ser Ala Asn Asp Phe Arg Glu Val Phe Lys Lys Asn Ile Glu |
|        549          558         567         576        585<br>aaa cgt gtg cgg agt ttg cca gaa gtg gat ggc ttg agc aaa<br>Lys Arg Val Arg Ser Leu Pro Glu Ile Asp Gly Leu Ser Lys |
|           594         603         612         621<br>gag aca gtg ttg age tca tgg ata gcc aaa tat gat gcc att<br>Glu Thr Val Leu Ser Ser Trp Ile Ala Lys Tyr Asp Ala Ile |
| 630         639         648         657         666<br>tac aga ggt gaa gag gac ttg tgc aaa cag cca aat aga atg<br>Tyr Arg Gly Glu Glu Asp Leu Cys Lys Gln Pro Asn Arg Met |
|        675         684         693         702        711<br>gcc cta agt gca gtg tct gaa ctt att ctg agc aag gaa caa<br>Ala Leu Ser Ala Val Ser Glu Leu Ile Leu Ser Lys Glu Gln |
|          720         729         738         747<br>ctc tat gaa atg ttt cag cag att ctg ggt att aaa aaa ctg<br>Leu Tyr Glu Met Phe Gln Gln Ile Leu Gly Ile Lys Lys Leu |
| 756         765         774         783         792<br>gaa cac cag ctc ctt tat aat gca tgt cag gta agt ggt ctc<br>Glu His Gln Leu Leu Tyr Asn Ala Cys Gln Val Ser Gly Leu |
| 798<br>tga 3'<br>*stop |

The entire protein NRP-5 consists of 266 amino acids.

The annotated translated NRP amino acid sequence NRP-5 has 76% similarity to a human calcium dependent activator protein of secretion (GenBankXP_036915) located on chromosome 3. Furthermore, exon 1 (339 nucleic acids) of the translated human chromosome 7 NRP-5 has 95.5% homology to a translated mouse 5' EST (RIKENBB632392). This protein shares domains present in NRP-1 and other NRPs that exhibit biological properties of neurite outgrownth, neuronal survival, neuronal proliferation and neuronal migration.

We have annotated a DNA sequence from the human genome located between the region 116668725-116667697 on the reverse complement strand of chromosome 6 (region according NCBI human genome annotation project). The protein coding sequence consists of 3 exons with the following locations: exon 1: 116668725-116668697; exon 2: 116668333-116668305; exon 3: 116667872-116667697. The sequence, herein termed NRP-6 consists of 234 nucleic acids that encode 78 amino acids. This sequence belongs to the human gene family of NRPs. The highest homology found to human ESTs presents identity from nucleic acids 59-234 compared to the human cDNA clone GenBankCS0DK001Y119 isolated from human placental tissue. This clone was sequenced from the 3'-prime end and consists of 924 nucleic acids. Because our homologue form ends with the stop codon TGA after 234 nucleic acids we are not dealing with the same gene product. The nucleotide sequence (SEQ ID NO: 12) encoding for an NRP, and the amino acid sequence (SEQ ID NO: 13; NRP-6) for the peptide is:

| SEQ ID NOs: 12 and 13 |
|---|
|          9         18         27         36<br>5' atg aga gac aaa caa cat cta aat gca aga cat aaa aag gaa  SEQ ID NO: 12<br>    Met Arg Asp Lys Gln His Leu Asn Ala Arg His Lys Lys Glu  SEQ ID NO: 13 |
|    45         54         63         72         81<br>agg aag gag aga tca tat agt aca aca cta caa ggt gtt ctc<br>Arg Lys Glu Arg Ser Tyr Ser Thr Thr Leu Gln Gly Val Leu |
|        90         99         108         117        126<br>aac aaa aag tct ttg tta gac ttc aat aat act att tgg tac<br>Asn Lys Lys Ser Leu Leu Asp Phe Asn Asn Thr Ile Trp Tyr |
|          135         144         153         162<br>ttc tat cag caa ata gga agc att cca ata ctt att aga tcc<br>Phe Tyr Gln Gln Ile Gly Ser Ile Pro Ile Leu Ile Arg Ser |
| 171         180         189         198         207<br>tct acc atc aga cac aga aat tac cta gaa aac aga aat gta<br>Ser Thr Ile Arg His Arg Asn Tyr Leu Glu Asn Arg Asn Val |

-continued

SEQ ID NOs: 12 and 13

```
      216           225           234
ttg cca aat ctc aaa caa gag ggc tga 3'
Leu Pro Asn Leu Lys Gln Glu Gly *stop
```

The amino acid sequence of NRP-6 has 14.1% identity and 44.9% similarity to the annotated NRP paralog on human chromosome 13, NRP-2. This protein shares domains present in NRP-1 and other NRPs (e.g., NRPs 2-5) that have biological properties of neurite outgrowth, neuronal survival, neuronal proliferation and neuronal migration.

Furthermore, another NRP-1 ortholog has been identified, a mouse NRP family member. The mouse NRP family member (here indicated as protein 2, SEQ ID NO: 17; herein termed NRP-7) is located within the arachne contig$_{13}$91157 of NCBI consisting of 339 nucleic acids using reading frame 1. Within an overlapping region there is a second ORF of 198 nucleic acids starting at position 29 of the annotated NRP paralog using frame 3. This ORF codes for a protein (here indicated as protein 1) with high identity to a truncated human DNA repair protein. By using the search paradigm tBLASTN using the biological active NRP peptide sequence: KDPEAR-RAPGSLHPCLAASCSAAG (SEQ ID NO: 18) we got a blast hit in the mouse EST RIKEN database. This 5'-generated mouse EST has the accession Number GenBank AK012518 and the following sequence (SEQ ID NO: 14):

```
5' ggcagcctcgagatggggaagatggcggctgctgtggcttcattagc cacgctggctgcagagcccagagaggatgctttccggaagcttttccgct tctaccggcagagccggccggggacagcggacctgggagccgtcatcgac ttctcagaggcgcacttggctcggagcccgaagcccggcgtgccccaggt aggaaaggaggagtagtgtgtgccagcctagcggccgactgggccacccg agactgggccgcctccgcggctttggagggaagcccctgctgggcctgtc cagtgagctgtaatgtcgagcgatgagcgaccagctgcctcgctgtccca
``` acgctctggccacggcttgtgccttgccgccatttccccaacccacgcg ggccacggcttgtgccctgccgccatttccccaacccacgcgacctgct c 3'

Protein 1 Reading Frame 3

Translation of open reading frame 3 (ORF of 198 nucleic acids starting at position 13 of the EST) reveals the following protein sequence (SEQ ID NO: 15):

SEQ ID NO: 15
MGKMAAAVASLATLAAEPREDAFRKLFRFYRQSRPGTADLGAVIDFSEAH
LARSPKPGVPQVGKEE

This sequence has 82% homology (identity and chemical similarity) of amino acid sequence to the human alkylated DNA repair protein with the GenBank accession number Q13686. The mouse form is C-terminal truncated and has only 66 of the 389 amino acids of the human DNA repair protein.

Protein 2 Reading Frame 1

An even longer ORF of 323 nucleic acids can be found within frame 1 of the EST sequence. We then annotated the 5' end of the 323 nucleic acid ORF in the mouse genome and found a new gene located in the mouse arachne contig_ 191157 sequence of the NCBI database between 23970 and 24374. The protein coding sequence consists of two exons with an overall length of 339 nucleic acids coding for 113 amino acids. The location of exon I is: 23970-23990, and for exon 2 it is: 24057-24374. The nucleotide sequence (SEQ ID NO: 16) and the amino acid sequence (SEQ ID NO: 17; NRP-7) of this mouse NRP ortholog of rat NRP-1 are:

SEQ ID NOs: 16 and 17

```
              9             18            27            36
5' atg aat cga aac cct gga gtc cct cga gat ggg gaa gat ggc    SEQ ID NO: 16
   Met Asn Arg Asn Pro Gly Val Pro Arg Asp Gly Glu Asp Gly    SEQ ID NO: 17

45            54            63            72            81
   ggc tgc tgt ggc ttc att agc cac gct ggc tgc aga gcc cag
   Gly Cys Cys Gly Phe Ile Ser His Ala Gly Cys Arg Ala Gln 90            99           108           117           126
       aga gga tgc ttt ccg gaa gct ttt ccg ctt cta ccg gca gag
       Arg Gly Cys Phe Pro Glu Ala Phe Pro Leu Leu Pro Ala Glu 135           144           153           162
           ccg gcc ggg gac agc gga cct ggg agc cgt cat cga ctt ctc
           Pro Ala Gly Asp Ser Gly Pro Gly Ser Arg His Arg Leu Leu 171           180           189           198           207
       aga ggc gca ctt ggc tcg gag ccc gaa gcc cgg cgt gcc cca
       Arg Gly Ala Leu Gly Ser Glu Pro Glu Ala Arg Arg Ala Pro
```

SEQ ID NOs: 16 and 17

```
          216            225            234            243            252
     ggt agg aaa gga gga gta gtg tgt gcc agc cta gcg gcc gac
     Gly Arg Lys Gly Gly Val Val Cys Ala Ser Leu Ala Ala Asp 261            270            279            288
     tgg gcc acc cga gac tgg gcc gcc tcc ggg ccg gct ttg gag
     Trp Ala Thr Arg Asp Trp Ala Ala Ser Gly Pro Ala Leu Glu 297            306            315            324            333
     gga agc ccc tgc tgg gcc tgt cca gtg agc tgt aat gtc gag
     Gly Ser Pro Cys Trp Ala Cys Pro Val Ser Cys Asn Val Glu 339
     cga tga   3'
     Arg *stop
```

The entire expressed amino acid sequence of NRP-7 contains 113 amino acids.

The protein function program tool SMART predicts a signal peptide sequence consisting of 28 amino acids. The protein has 13.6% identity and 23.6% similarity towards the NRP ortholog on human chromosome 13, and has neuronal survival, migration, proliferation and outgrowth activity similar to NRP-1.

A second mouse NRP family member is located within the genomic clone bM344E9 of the mouse Sanger database on the reverse strand. By using the search program tBLASTN using the biologically active NRP peptide sequence: KDPE-ARRAPGSLHPCLAASCSAAG (SEQ ID NO: 18) we obtained an area of similarity in the genomic mouse Sanger database within the genomic clone bM344E9. The protein coding sequence has been annotated and consists of 5 exons and is 423 nucleic acids in total length coding for 141 amino acids. The locations for the coding exons are the following: exon 1: 5609-5596; exon 2: 5502-5489; exon 3: 5398-5283; exon 4: 5243-5229; exon 5: 5215-4952. The coding nucleotide sequence (SEQ ID NO: 19) and the amino acid sequence (SEQ ID NO: 20) of the mouse ortholog of rat NRP-1 (herein termed NRP-8) is:

SEQ ID NOs: 19 and 20

```
                  9            18            27            36
   5' atg tgc act ctg cag gta tgg tct tcc tcc ctc cct tcc ctc  SEQ ID NO: 19
      Met Cys Thr Leu Gln Val Trp Ser Ser Ser Leu Pro Ser Leu  SEQ ID NO: 20

45            54            63            72            81
      ccc cac ctc tct gag ggg tca ggg gtc agc att tgg atg ctg
      Pro His Leu Ser Glu Gly Ser Gly Val Ser Ile Trp Met Leu 90            99           108           117           126
      ctc cca cca ggc cca gct tta gaa atg aat tcc tcc ggc ctc
      Leu Pro Pro Gly Pro Ala Leu Glu Met Asn Ser Ser Gly Leu 135           144           153           162
      ctt tat act ctt gag acc tcc tgg gga acc agg acc ctc ttg
      Leu Tyr Thr Leu Glu Thr Ser Trp Gly Thr Arg Thr Leu Leu 171           180           189           198           207
      gct cct ctg gtg aca tac atg gga tct gat gca tct gag gtg
      Ala Pro Leu Val Thr Tyr Met Gly Ser Asp Ala Ser Glu Val 216           225           234           243           252
      gat gca aga aga gca aaa aag agt ctc cac tgc atc ctg tct
      Asp Ala Arg Arg Ala Lys Lys Ser Leu His Cys Ile Leu Ser 261           270           279           288
      gac acc agc cat ccc cgg ggc cat gcc cgg aat gag agg agg
      Asp Thr Ser His Pro Arg Gly His Ala Arg Asn Glu Arg Arg 297           306           315           324           333
      ctt ggc ctt ggg gtt tgg aag acc gag ctt tgg gtc cag acc
      Leu Gly Leu Gly Val Trp Lys Thr Glu Leu Trp Val Gln Thr 342           351           360           369           378
      ctg cta tca ctg atg gtg aca tcc tgg gaa gtt tat gaa act
      Leu Leu Ser Leu Met Val Thr Ser Trp Glu Val Tyr Glu Thr 387           396           405           414
```

-continued

SEQ ID NOs: 19 and 20

```
cgt tcg tgc ctc agt ttc ccc atc agg cct tta gct cac tgg
Arg Ser Cys Leu Ser Phe Pro Ile Arg Leu Leu Ala His Trp 423
gga taa   3'   END
Gly *stop
```

The expressed amino acid sequence of NRP-8 contains 141 amino acid residues.

The asparagine residue at position 112-114 is putatively N-glycosylated according to the occurrence of an N-glycosylation consensus sequence. The new mouse NRP-1 ortholog NRP-8 has 35.5% homology to the human NRP ortholog located on chromosome 13 (NRP-2) and 28.9% homology to the mouse NRP-1 ortholog located on the arachne contig from NCBI. Furthermore this peptide comprises amino acid sequence domains similar to those present in NRP-1 or other NRP peptides and this peptide has biological properties including neuronal migration, proliferation, survival and/or neurite outgrowth.

In addition to the NRP compounds described above, we have identified other genes having NRP-like peptide domains, that also can be useful for expressing NRPs. These include genes from mycobacteria and tumor cells. A recently published paper has disclosed a PE multigene family of Mycobacterium tuberculosis containing a consensus sequence (PE_PGRS) which is similar to our proposed sequence (PGR/S). They also mention that these proteins are released in the host, by the bacterium, to promote bacterial survival. Here are the examples they provided in the paper, where the PE_PGRS consensus sequence was found.

Amino acid sequence of the Rv1S18c gene product of *M. tuberculosis*
(SEQ ID NO: 21):

```
msfvvtipea laavatdlag igstigtana aaavptttvl aaaadevsaa maalfsghaq  SEQ ID NO: 21 ayqalsaqaa lfheqfvral tagagsyaaa eaasaapleg vldvinapal allgrplign gangapgtga nggdggilig nggaggsgaa gmpggnggaa glfgnggagg aggnvasgta gfggaggagg llygaggagg aggragggvg giggaggagg nggllfgagg aggvgglaad agdggaggdg glffgvggag gaggtgtnvt ggaggaggng gllfgaggvg gvggdgvafl gtapggpgga ggagglfgvg gaggaggigl vgnggaggsg gsallwgdgg aggaggvgst tggaggaggn agllvgagga ggagalggga tgvggaggng gtagllfgag gaggfgfgga ggagglggka gligdggdgg aggngtgakg gdggagggai lvgnggnggn adsgtpngsa gtggaggllg kngmnglp
```

Amino acid sequence of Epstein-Barr Virus Nuclear Antigen 1
(SEQ ID NO: 22):

```
msdegpgtgp gnglgekgdt sgpegsggsg pqrrggdnhg rgrgrgrgrg ggrpgapggs  SEQ ID NO: 22 gsgprhrdgv rrpqkrpsci gckgthggtg agagaggaga ggagagggag agggaggagg aggagaggga gagggaggag gagagggaga gggaggagag ggaggaggag agggagaggg aggagaggga ggaggagagg gagaggagga ggagaggaga gggaggagga gaggagagga gaggagagga ggagaggagg agaggaggag agggaggaga gggaggagag gaggagagga ggagaggagg agagggagag gagagggrg rggsggrgrg gsggrgrggs ggrrgrgrer arggsrerar grgrgrgekr prspssqsss sgspprrppp grrpffhpvg eadyfeyhqe ggpdgepdvp pgaieqgpad dpgegpstgp rgqgdggrrk kggwfgkhrg qggsnpkfen iaeglralla rshverttde gtwvagvfvy ggsktslynl rrgtalaipq crltplsrlp fgmapgpgpq pgplresivc yfmvflqthi faevlkdaik dlvmtkpapt cnirvtvcsf ddgvdlppwf ppmvegaaae gddgddgdeg gdgdegeegq e
```

From Brennan, M. J. and Delogu, G., (2002). The PE multigene family: a 'molecular mantra' for mycobacteria. Trends in Microbiology 5: 246-249.

It can be appreciated that the entire sequence of NRP-1-NRP 8 need not be used. Rather, peptide fragments of about 8 amino acids can be used according to embodiments of this invention. Given the consensus sequence domains herein identified, one can fashion synthetic peptides or can truncate naturally occurring NRPs to obtain portions of peptides that are biologically active. Methods of truncation (e.g., using synthetic DNA) or enzymatic modification of expressed peptides are known in the art.

Uses of NRP Compounds

Thus, the invention includes embodiments which relate to NRPs, peptides encoded by NRP-1, homologs, orthologs or paralogs of NRP-1, analogs of NRP-1, and prodrugs of NRP-1, where a prodrug of NRP-1 is a molecule that may be enzymatically, metabolically or otherwise modified to become NRP-1, a NRP homolog, NRP paralog, an NRP ortholog or an NRP analog. Such molecules are collectively termed as "NRP compounds." NRP compounds may be encoded for by nucleotide sequences, which may be DNA or RNA and which may be single stranded or double stranded. It will be understood that the invention includes sequences complementary to the sequences described in this application as well as the sequences themselves.

As indicated above, embodiments of the present invention are based upon the inventors' surprising finding that NRP-1 and related NRPs can induce neurons and neuroblasts to proliferate and migrate. Proliferation and migration of neural cells into areas of damage caused by acute brain injury or chronic neurodegenerative disease can result in improvement in neural functioning. Thus, NRP compounds may be used to treat a variety of disorders and conditions where brain tissue degenerates or has died.

Disorders and Conditions Treatable with NRPs

Disorders and conditions in which NRP compounds can be of benefit include:

Infections of the central nervous system including bacterial, fungal, spirochetal, parasitic and sarcoid including pyrogenic infections, acute bacterial meningitis, leptomeningitis;

Cerebrovascular diseases including stroke, ischemic-stroke, atherosclerotic thrombosis, lacunes, embolism, hypertensive haemorrhage, ruptured aneurysms, vascular malformations, transient ischemic attacks, intracranial haemorrhage, spontaneous subarachnoid haemorrhage, hypertensive encephalopathy, inflammatory diseases of the brain arteries, decreased perfusion caused by, for example, cardiac insufficiency (possibly resulting from coronary bypass surgery) and other forms of cerebrovascular disease;

Craniocerebral trauma including basal skull fractures and cranial nerve injuries, carotid-cavernous fistula, pneumocephalus, aerocele andrhinorrhea, cerebral contusion, traumatic intracerebral haemorrhage, acute brain swelling in children;

Demyelinating diseases including neuromyelitis optica, acute disseminated encephalomyelitis, acute and subacute necrotizing haemorrhagic encephalitis, diffuse cerebral sclerosis of Schilder and multiple sclerosis in conjunction with peripheral neuropathy;

Degenerative diseases of the nervous system including syndrome of one or more of progressive dementia, diffuse cerebral atrophy, diffuse cortical atrophy of the non-Alzheimer type, Lewy body dementia, Pick's disease, frontotemporal dementia, thalamic degeneration, non-Huntingtonian types of Chorea and dementia, cortico-spinal degeneration (Jakob), the dementia-Parkinson-amyotrophic lateral sclerosis complex (Guamanina and others);

Acquired metabolic disorders of the nervous system including metabolic diseases presenting as a syndrome comprising one or more of confusion, stupor or coma-ischemia-hypoxia, hypoglycaemia, hyperglycemia, hypercapnia, hepatic failure and Reye syndrome, metabolic diseases presenting as a progressive extrapyramidal syndrome, metabolic diseases presenting as cerebellar ataxia, hyperthermia, celiac-sprue disease, metabolic diseases causing psychosis or dementia including Cushing disease and steroid encephalopathy, thyroid psychosis and hypothyroidism, pancreatic encephalopathy;

Diseases of the nervous system due to nutritional deficiency;

Alcohol and alcoholism;

Disorders of the nervous system due to drugs and other chemical agents including opiates and synthetic analgesics, sedative hypnotic drugs, stimulants, psychoactive drugs, bacterial toxins, plant poisons, venomous bites and stings, heavy metals, industrial toxins, anti-neoplastic and immunosuppressive agents, thalidomide, aminoglycoside antibiotics (ototoxicity) and penicillin derivatives (seizures), cardioprotective agents (beta-blockers, digitalis derivatives and amiodarone).

As illustrated by the preceding list, compositions and methods of the invention can find use in the treatment of human neural injury and disease. Still more generally, the compositions and methods of the invention find use in the treatment of human patients suffering from neural damage as the result of acute brain injury, including but not limited to diffuse axonal injury, perinatal hypoxic-ischemic injury, traumatic brain injury, stroke, ischemic infarction, embolism, and hypertensive haemorrhage; exposure to CNS toxins, infections of the central nervous system, such as, bacterial meningitis; metabolic diseases such as those involving hypoxic-ischemic encephalopathy, peripheral neuropathy, and glycogen storage diseases; or from chronic neural injury or neurodegenerative disease, including but not limited to Multiple Sclerosis, Lewy Body Dementia, Alzheimer's disease, Parkinson's disease and Huntington's disease. Patient's suffering from such diseases or injuries may benefit greatly by a treatment protocol able to initiate neuronal proliferation and migration, as well as neurite outgrowth.

Still more generally, the invention has application in the induction of neuronal and neuroblast migration into areas of damage following insult in the form of trauma, toxin exposure, asphyxia or hypoxia-ischemia.

NRP compounds, including NRP-1, its orthologs, analogs, paralogs and prodrugs containing the identified NRP peptide domains, can be used to promote neuronal and neuroblast migration. Most conveniently, this can be effected through direct administration of NRP compounds to the patient.

However, while NRPs can be advantageously used, there is no intention to exclude administration of other forms of NRP compounds. For example, human paralog forms or peptide fragments of NRP can be administered in place of NRP. By way of example, the effective amount of NRP in the CNS can be increased by administration of a pro-drug form of NRP that comprises NRP and a carrier, NRP and the carrier being joined by a linkage that is susceptible to cleavage or digestion within the patient. Any suitable linkage can be employed which will be cleaved or digested to release NRP following administration.

Another suitable treatment method is for NRP levels to be increased through an implant that is or includes a cell line that is capable of expressing NRP or analogs, paralogs or pro-peptides of an NRP in an active form within the central nervous system of the patient.

An NRP can be administered as part of a medicament or pharmaceutical preparation.

This can involve combining NRP compounds with any pharmaceutically appropriate carrier, adjuvant or excipient. Additionally an NRP compound can be used with other non-NRP neuroprotective, proliferative, or other agent. The selection of the carrier, adjuvant or excipient will of course usually be dependent upon the route of administration to be employed.

The administration route can vary widely. An NRP may be administered in different ways: intraperitoneal, intravenous or intracerebroventricular. The peripheral application may be the way of choice because then there is no direct interference with the central nervous system.

Any peripheral route of administration known in the art can be employed. These can include parenteral routes for example injection into the peripheral circulation, subcutaneous, intraorbital, ophthalmic, intraspinal, intracisternal, topical, infusion (using eg. slow release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (eg. amounts which eliminate or reduce the patient's pathological condition) to provide therapy for the neurological diseases described above.

One route of administration includes subcutaneous injection (e.g., dissolved in 0.9% sodium chloride) and oral administration (e.g., in a capsule).

It will also be appreciated that it may on occasion be desirable to directly administer NRP compounds to the CNS of the patient. This can be achieved by any appropriate direct administration route. Examples include administration by lateral cerebroventricular injection or through a surgically inserted shunt into the lateral cerebroventricle of the brain of the patient.

Determining Doses of NRP

The determination of an effective amount of an NRP to be administered is within the skill of one of ordinary skill in the art, and will be routine to those persons skilled in the art. In certain embodiments, the amount of an NRP to be used can be estimated by in vitro studies using an assay system as described herein. The final amount of an NRP to be administered will be dependent upon the route of administration, upon the NRP used and the nature of the neurological disorder or condition that is to be treated. A suitable dose range may for example, be between about 0.01 mg to about 1 mg per 100 g of body weight, alternatively about 0.06 µg to about 0.6 mg of NRP-1 per 100 g of body weight where the dose is administered centrally.

For inclusion in a medicament, NRP can be directly synthesized by conventional methods such as the stepwise solid phase synthesis method of Merryfield et al., 1963 (J. Am. Chem. Soc. 15:2149-2154). Such methods of peptide synthesis are known in the art, and are described, for example, in Fields and Colowick, 1997, *Solid Phase Peptide Synthesis* (Methods in Enzymology, vol. 289), Academic Press, San Diego, Calif. Alternatively synthesis can involve the use of commercially available peptide synthesizers such as the Applied Biosystems model 430A.

As a general proposition, the total pharmaceutically effective amount of NRP-1 administered parenterally per dose will be in a range that can be measured by a dose response curve. One range is between about 0.06 mg and about 0.6 mg per 100 g body weight. For example, NRP-1 in the blood can be measured in body fluids of the mammal to be treated to determine dosing. Alternatively, one can administer increasing amounts of the NRP-1 compound to the patient and check the serum levels of the patient for NRP-1. The amount of NRP-1 to be employed can be calculated on a molar basis based on these serum levels of NRP-1.

Specifically, one method for determining appropriate dosing of the compound entails measuring NRP levels in a biological fluid such as a body or blood fluid. Measuring such levels can be done by any means, including RIA and ELISA. After measuring NRP levels, the fluid is contacted with the compound using single or multiple doses. After this contacting step, the NRP levels are re-measured in the fluid. If the fluid NRP levels have fallen by an amount sufficient to produce the desired efficacy for which the molecule is to be administered, then the dose of the molecule can be adjusted to produce maximal efficacy. This method can be carried out in vitro or in vivo. This method can be carried out in vivo, for example, after the fluid is extracted from a mammal and the NRP levels measured, the compound herein is administered to the mammal using single or multiple doses (that is, the contacting step is achieved by administration to a mammal) and then the NRP levels are remeasured from fluid extracted from the mammal.

NRP compounds are suitably administered by a sustained-release system. Suitable examples of sustained-release compositions include semi-permeable polymer matrices in the form of shaped articles, for example, films, or microcapsules. Sustained-release matrices include polylactides (U.S. Pat. No. 3,773,919; EP 58,481), poly(2-hydroxyethyl methacrylate) (Langer et al., 1981), ethylene vinyl acetate (Langer et al., supra), or poly-D-(-)-3-hydroxybutyric acid (EP 133, 988). Sustained-release compositions also include a liposomally associated compound. Liposomes containing the compound are prepared by methods known to those of skill in the art, as exemplified by DE 3,218,121; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102,324. In some embodiments, liposomes are of the small (from or about 200 to 800 Angstroms) unilamellar type in which the lipid content is greater than about 30 mol. percent cholesterol, the selected proportion being adjusted for the most efficacious therapy. All U.S. parents referred to herein, both supra and infra, are hereby incorporated by reference in their entirety. PEGylated peptides having a longer life than non-PEGylated peptides can also be employed, based on, for example, the conjugate technology described in WO 95/32003 published Nov. 30, 1995.

For parenteral administration, doses may be between about 0.01 to about 1 mg per 100 g of body weight, alternatively about 0.06 µg to 0.6 mg of NRP compound per 100 g body weight. In some embodiments, the compound can be formulated generally by mixing each at a desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. It can be appreciated that the above doses are not intended to be limiting. Other doses outside the above ranges can be determined by those with skill in the art.

In some embodiments, formulations can be prepared by contacting a compound uniformly and intimately with liquid carriers or finely divided solid carriers or both. Then, if desired, the product can be shaped into the desired formulation. In some embodiments, the carrier is a parenteral carrier, alternatively, a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are desirably non-toxic to recipients at the dosages and concentrations employed, and include, by way of example only, buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

An NRP compound can be desirably formulated in such vehicles at a pH of from about 4.5 to about 8. It will be understood that use of certain of the foregoing excipients, carriers, or stabilizers will result in the formation of salts of the compound. The final preparation may be a stable liquid or lyophilized solid.

In other embodiments, adjuvants can be used. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Desirably, an NRP compound to be used for therapeutic administration may be sterile. Sterility can be readily accomplished by filtration through sterile filtration membranes (e.g., membranes having pore size of about 0.2 micron). Therapeutic compositions generally can be placed into a container having a sterile access port, for example an intravenous solution bag or vial having a stopper pierceable by a hypodermic injection needle.

In other embodiments, an NRP compound can be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 0.01% (w/v) aqueous solution of compound, and the resulting mixture is lyophilized. The infusion solution can be prepared by reconstituting lyophilized compounds using bacteriostatic water or other suitable solvent.

Gene Therapy

In other embodiments of this invention, therapeutic methods include gene therapy for treating an organism, using a nucleic acid encoding an NRP compound. Generally, gene therapy can be used to increase (or overexpress) NRP levels in the organism. Examples of nucleotide sequences include SEQ ID NOs: 1, 3, 4, 6, 8, 10, 12, 14, 16 or 19, or portions thereof that encode peptides having the consensus domains and biological properties of NRP. It can be appreciated that other sequences can be used to encode a pro-NRP, which, upon cleavage, can result in a biologically active NRP.

Any suitable approach for transfecting an organism with a sequence encoding an NRP can be used. For example, in vivo and ex vivo methods can be used. For in vivo delivery, a nucleic acid, either alone or in conjunction with a vector, liposome, precipitate etc. is injected directly into the organism, for example, a human patient, and in some embodiments, at the site where the expression of an NRP compound is desired. For ex vivo treatment, an organism's cells are removed, the nucleic acid is introduced into these cells, and the modified cells are administered to the organism either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

In certain embodiments, in vivo nucleic acid transfer techniques include transfection with viral vectors (such as adenovirus, Herpes simplex I virus, or adeno-associated virus) and lipid-based systems (useful lipids for lipid-mediated transfer of the gene are N-[-1-(2,3-dioleyloxy)propyl]-N,N,N-trimethylammonium (DOTMA), dioleoylphatidylethanolamine (DOPE) and 3-β[N-(N',N'-dimethylamionethane)carbomoyl]cholesterol (DC-Chol), for example. In some situations it may be desirable to provide the nucleic acid source with an agent that directs the nucleuc acid-containing vector to target cells. Such "targeting" molecules include antibodies specific for a cell-surface membrane protein or the target cell, a ligand for a receptor on the target cell, etc. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein.

Kits are also contemplated within the scope of this invention. A typical kit can comprise a container, in some embodiments a vial, for the NRP formulation comprising one or more NRP compounds in a pharmaceutically acceptable buffer and

EXAMPLES

The following examples are provided to illustrate certain embodiments of this invention. It can be readily appreciated that other embodiments can be devised and still remain within the scope of this invention. All of these other embodiments are considered to be part of this invention.

Example 1

Identification of Human and Mouse NRPs

Using bioinformatic tools, we identified NRPs within the human, rat and mouse genomes. These new NRP genes were annotated using the following methods.

We performed a BLASTP search using the 16 amino acid rat NRP-1 as a template. We found a sequence having 100% identity to the rat NRP-1 sequence: a human cachexia-related protein. The cDNA of the human cachexia-related protein is encoded by 5 exons located on human chromosome 12. Because of the identity of the rat NRP-1 and a portion of the human cachexia protein, a new annotation of NRP orthologs was orientated alongside these 5 exons. tBlastN searches within the human NCBI-database revealed a previously unknown open reading frame (ORF) of 321 nucleic acids on chromosome 13. This sequence encodes a peptide having striking homology to the cachexia-related protein fragment having amino acids 1-30 (cachexia protein without signal sequence). These methods were also used to identify other human NRP orthologs, as well as mouse NRP orthologs.

A program for multiple or pairwise alignment of protein or nucleic acid sequences, ClustalW, was used to perform alignment analysis. In order to identify the protein-coding exons of the newly annotated NRP gene on human chromosome 13, NRP-2 (SEQ ID NO: 4) the protein encoding nucleotide sequences of the cachexia protein were compared with the region around the ORF of chromosome 13. The non-coding 5' region of cachexia DNA was used to determine exon 1 of the NRP ortholog. For annotating other human and mouse NRP's, alignments of amino acid sequences were performed. By the term annotation, we mean to include processes for identifying DNA sequences containing protein encoding information, splice sites to create new exons, and for predicting the existence and structures, including specific amino acid, peptide or protein domains suitable for identification of NRPs having desirable biological or other properties.

To identify 5' and 3' splice sites in unprocessed RNA, (pre-mRNA), hexamer human consensus sequences for splice sites of the splicosomes were aligned to the respective chromosome 13 NRP sequence (SEQ ID NO: 4) to identify exon-intron boundaries in order to determine the number of exons present in the protein-coding sequence of a newly annotated NRP gene sequence. For identification of mouse splice sites, publications from Baldwin et al. and Wagener et al. were used as templates. For human splice site identification, publications from van der Flier et al. and Guth et al. were used.

Thus, we conclude that multiple NRPs exist in a newly recognized gene family of neural regeneration peptides, having related amino acid domains and having similar biological properties. Members of the NRP gene family include peptides derived from human, rat, mouse and bacterial origin. NRPs of this family can be used to treat a variety of neurological conditions or injury to neural tissue in which neural repair is needed.

Example 2

In Vitro Assay for Evaluating Migration-Inducing Activity I

We developed a new assay system for identifying NRP having migration-inducing acgtivity. The assay system was used following guidelines approved by the Gesundheitsamt Magdeburg animal ethics committee. Newborn Long Evans rats (P0) were killed by decapitation, and neural tissues were used for preparation of organotypic cultures (OTCs). Neocortical tissue (areas 17-18 according to the Paxinos rat atlas of the developing rat brain) and thalamic tissue from the dorsal thalamus (visual areas) were extracted. These areas represent the visual axis. The dorsal thalamus was accessed by an intersection cut to remove the hypothalamus. Subsequently, the thalamus was sliced frontally using a McIllwain tissue chopper into 350 μm thick slices. Using a dissecting microscope, the habenula nucleus served as a landmark to select only dorsal thalamic areas. Cortical tissues were cut using two sagittal and two frontal intersections in order to obtain areas 17-18 of the occipital cortex. Before the last frontal cut was made, the hippocampal formation was removed. The cortical tissues were sliced by a McIllwain tissue chopper into 350 μm thick frontal slices and was incubated in Gey's balanced salt solution (GBSS) plus 0.65% D(+)glucose, and tissues were kept at 4° C. for at least 30-40 minutes for recovery.

For each assay, two slices of tissue, one cortical and one thalamic, were arranged at a distance at least about 3 mm from each other on a glass substrate (e.g., a cover slip; FIG. 1) and were adhered to the substrate using a plasma clot and the tissues were subsequently cultured (cultivated) at 36° C. in a roller tube incubator as organotypic cultures using BME/HBSS (Invitrogen) medium supplemented with 25% heat-inactivated horse serum (Gaehwiler, 1981). A 712.5 μl sample of prepared medium was supplemented with 37.5 μl purified rat NRP-1 (in concentrated or diluted form) in 0.01 M sodium phosphate (pH 7.3) or phosphate alone (control). For the experiments using 600 ng/ml NRP-1, the peptide was concentrated 4 times by speed vacuum centrifugation. The medium was changed every three days. After each study was completed, the tissues were fixed using conventional fixatives, and migrating neurons were analysed by immunocytochemistry.

Using prior art conditions, in which thalamic and cortical tissues were close together (less than 1.5 mm from each other), the tissues spontaneously produce reciprocal neurite outgrowths and interconnecting cell bridges within 7-10 days after co-culturing commencement (Bolz et al., 1992). The presence of spontaneous regeneration and formation of interconnecting cell bridges confounds attempts to identify exogenously added neuroregeneration molecules, such as NRPs.

However, we quite unexpectedly found that if the thalamic and cortical tissues were separated by more than 2 mm, no spontaneous regeneration features appeared. Thus, any observations of neurite outgrowths or interconnecting cell bridges are due to the influence of factors added to the culture medium. We found that NRPs, including rat NRP-1 and human and mouse orthologous NRPs induced one or more thalamocortical cell bridge(s) over a long distance, for example, about 3-5 mm within a time of only 3 to 4 days of cultivation (see FIG. 1). Thus, in certain embodiments of this invention, NRPs can be identified and/or quantified. In other embodiments, NRPs amounts can be standardized, forming a basis for therapeutic application of NRPs to treat neurological diseases or conditions.

Statistical Analysis

Figure 4:
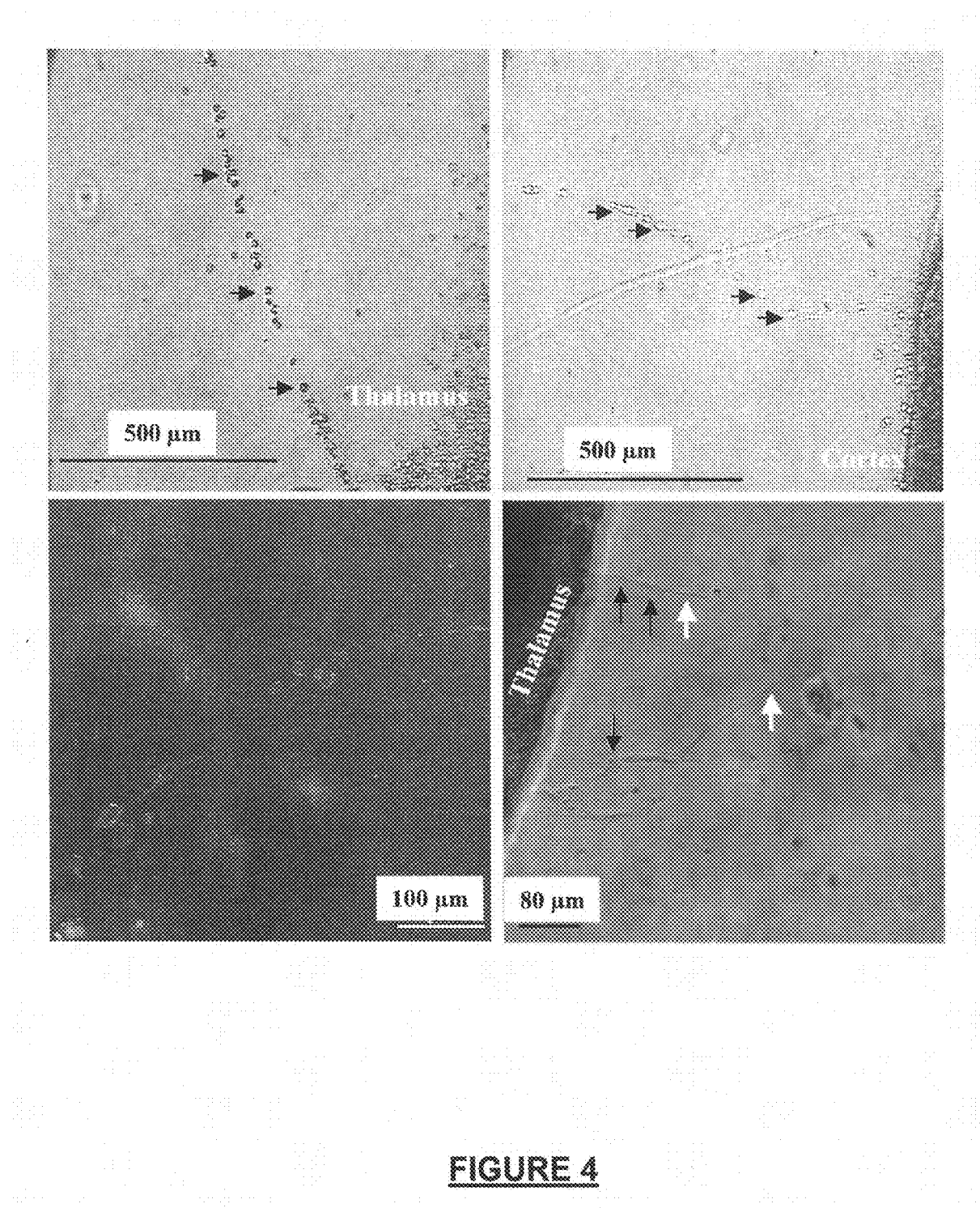
FIG. 4 shows a photomicrograph demonstrating tissue specificity of the originating cell chain within the thalamo-cortical system. The migrating cell chain/cell stream originates from the thalamic tissue (FIG. 4A). At the concentration producing the greatest effect was 3 nM NRP-1. Cortical migration chains occurred and are shown in FIG. 4B. Greater magnification reveals that the migrating MAP-2-positive neurons are interconnected by neurite structures (arrow in FIG. 4C).

Migration of the thalamic neurones was determined after 3 days of co-culture in the presence of NRP. The migration distances were measured by a micrometer scaled-microscopic ocular, beginning from the tissue margin of the migrating cell stream. See FIG. 4. As a threshold value for the formation of a migrating cell chain, a number of at least 5 interconnected neurons was considered. For the determination of the dose-response curve, the longest distance of a migrated neuron from the thalamic tissue margin was measured. Results are given as mean values +/− standard deviation.

Figure 3:
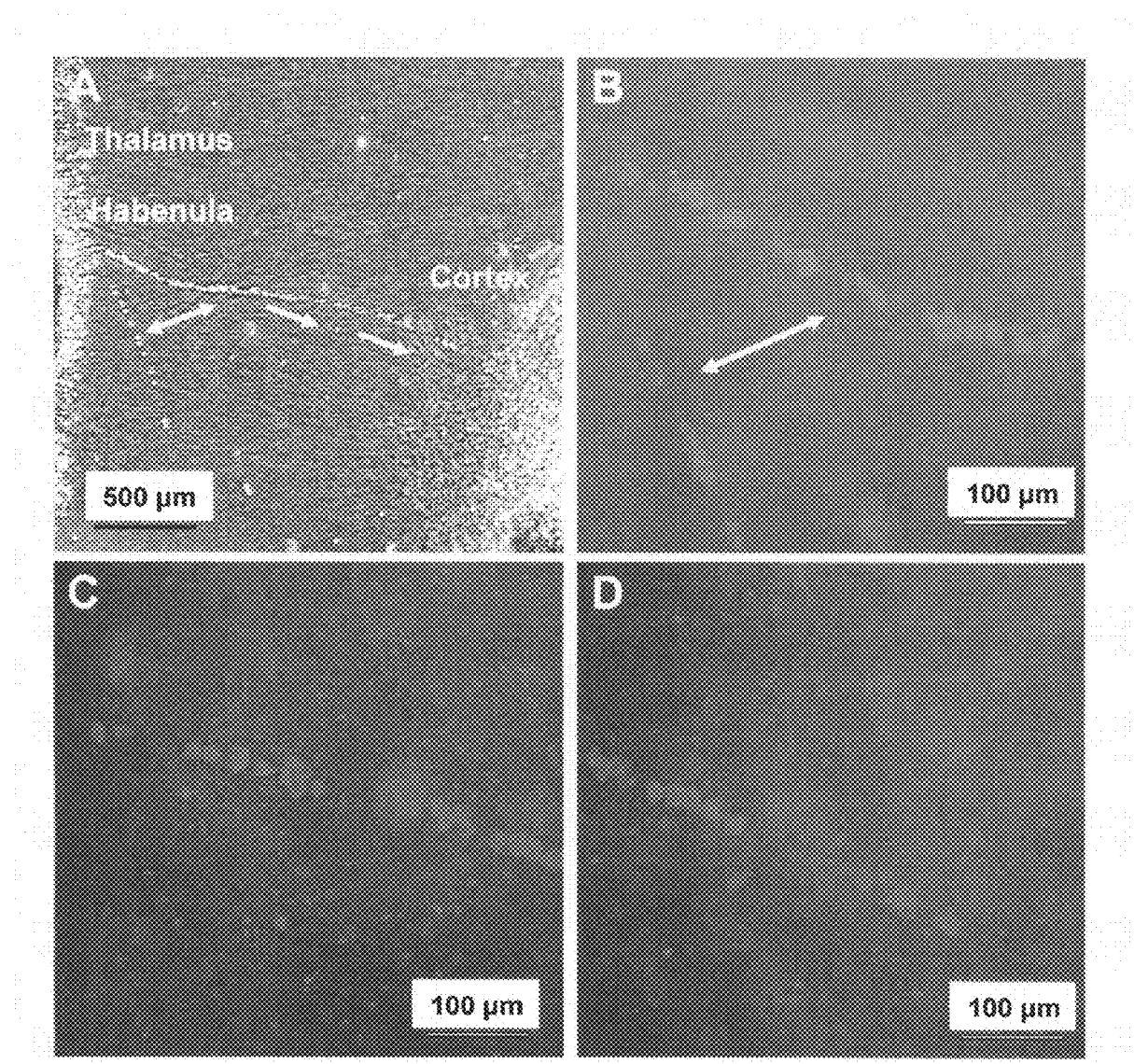
FIG. 3 depicts photomicrographs of formation of neuronal cell bridges between thalamic and cortical tissues within thalamocortical OTCs after 4 days of incubation in vitro. At the commencement of incubation, cultures were supplemented with 300 ng/ml NRP extract (as total protein of the hydroxy apatite chromatography).
Figure 5:
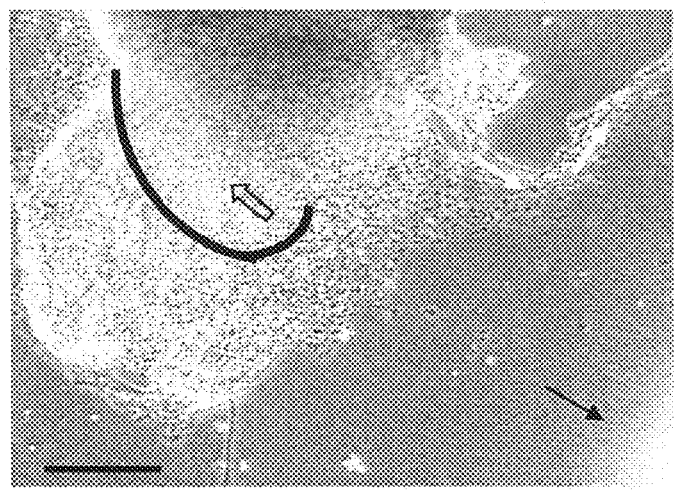
FIG. 5 shows a phase contrast micrograph of the thalamic region of a NRP-1 supplemented OTC (3 nM highly purified cation exchange eluate) 24 hours after the start of incubation. The black line indicates the original margin of the habenula nucleus (open arrow). There was massive "tissue spreading" of the habenula nucleus. The white arrows indicate a cell chain that is in the migration process. A number of neurites originated from the migrating cell chain and project to the cortical tissue (black arrow). Bar: 1000 μm.

Results: Induction of Neuronal Cell Chain Migration and/or Neuronal Cell Stream Migration FIG. 3 depicts formation of cell bridges induced by rat NRP-1 harvested from hippocampal OTC supernatant. The NRP-1 was administered to the thalamocortical OTCs at cultivation start (see FIG. 3). Under these conditions, the formation of cell bridges comprising both proliferating and differentiated neurons takes place. At most NPP concentrations, cell bridges originated from the thalamic tissue (see FIGS. 3 and FIGS. 4A and 4D), and only at a single dose of NRP, a cell bridge originated from cortical tissue as well (FIG. 4B). One possible reason for this observation could be the different anatomy of thalamic and cortical tissue, respectively. Neocortical tissue possesses a basal lamina that can hinder migrating thalamic cells from penetrating into the cortical tissuse, whereas the thalamus lacks such a basal lamina. Before neuronal migration occurred, an interconnecting neurite network between the respective tissues was formed within the first 36 hours after cultivation had started in NRP-1 supplemented thalamocortical co-cultures (see FIG. 5). The first migrating cells were observed between 30 and 48 hours after cultivation began (see FIG. 4D).

Figure 6:
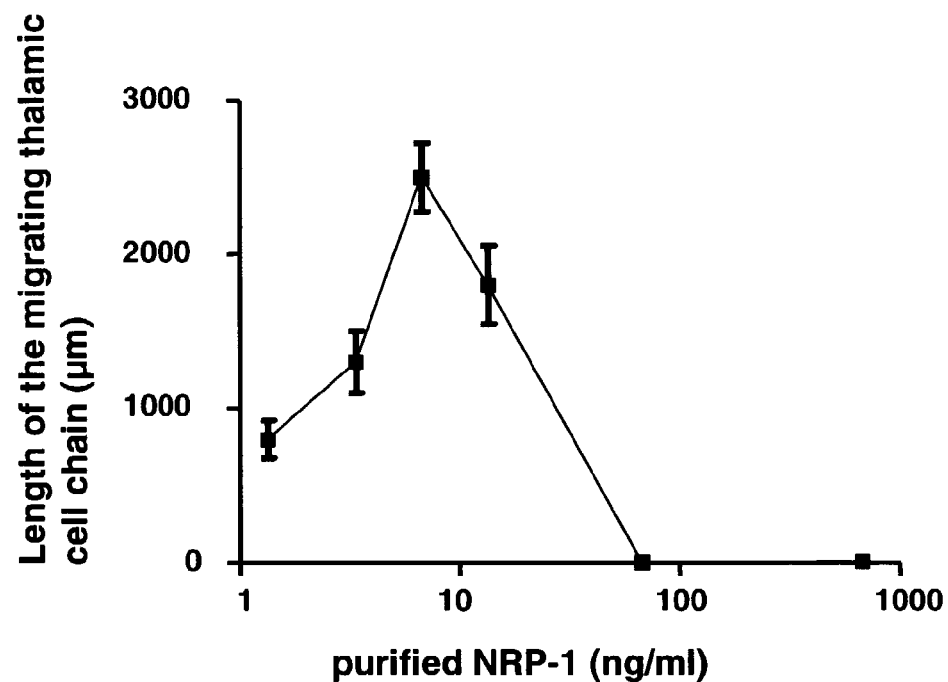
FIG. 6 depicts a graph of a dose-response relationship for NRP-1 in thalamocortical OTCs. In order to assay the biological activity range of NRP-1, homogenously purified (cation exchanger) protein was administered to the thalamocortical OTCs at the start of incubation. For the dose-response curve, concentrations of 2, 4, 6, 20, 60 and 600 ng/ml of NRP-1 were tested. At 2 ng/ml (1 nM), the biological activity (induction of neuronal migration) was clearly detected. The concentration producing the largest migration-promotion was 6 ng/ml (3 nM). At concentrations between about 20-60 ng/ml (10-30 nM), NRP-1 did not increase neuronal migration. All concentrations were tested 6 times in the assay.

A dose-response curve (see FIG. 6) revealed that an applied concentration of 6 ng/ml (3 nM-1/500 diluted 3 µg/ml homogenously purified NRP-1) established a cell bridge of 2500±240 µm length between the thalamic and cortical tissues. The concentration range for biological activity range within the in vitro system was between about 1 and 10 nM. The concentration of 3 µg/ml NRP-1 was estimated from the absorbance value of 0.003 measured at the UV wavelength of 280 nm.

We conclude that NRP-1 induces neuronal migration in postnatal explant thalamocortical brain slices. The migrating cell chains overbridge gap regions between thalamic and cortical tissue. We further conclude that NRPs can be used to promote neuronal cell migration. The ability of NRPs to induce neuronal migration indicates an application for NRP-1 in restoring neuronal networks, which degenerate in neurodegenerative diseases and injuries.

Example 3

Migrating Cells are of Neuronal Origin and Adopt a Differentiated Phenotype

To determine the cellular nature of cell bridges, we used neural-specific immunohistochemitsry. Immunohistochemistry was carried out according to methods of (Obst and Wahle, 1995). OTCs as described above were rinsed twice in 0.1 M phosphate buffer for 3 h. After a study was carried out, tissues were fixed using conventional fixatives suitable for immunohistochemistry. To improve antibody penetration into the tissues and cells, OTCs were incubated for 10 min in a freezing solution consisting of 25% sucrose; 10% glycerol; 100 mM NaCl in 0.01 M phosphate buffer (pH 7.4) at −80° C. (Gúlyas et al., 1996). OTCs were then incubated for 5 min in 1% $H_2O_2$ followed by a treatment of 0.4% Triton 100 and 10% normal goat serum (blocking solution) for 3 h (Sigma chemicals). Primary antibodies (anti-parvalbumin IgG; anti-calretinin IgG; anti-MAP-2 IgG) were incubated with 0.4% Triton; 2% BSA; 2% normal goat serum in PBS over night at 4° C. Biotinylated secondary antibody diluted in 0.2% Triton; 2% BSA; 2% normal goat serum in PBS (1/200) was incubated for 2 h, followed by avidin-biotin-horseradish peroxidase complex (Dakopatts, Hamburg, Germany) or alternatively by streptavidin-Cy3 complex (Sigma). For double staining experiments, biotyinylated secondary antibody followed by streptavidin-Cy2 and a goat anti-mouse IgG coupled to Cy2 (1/150) were used. OTCs were rinsed for 3×15 min between incubation steps. Peroxidase reactivity was developed with 0.05% diaminobenzidine (DAB) and 0.009% $H_2O_2$ in 50 mM Tris buffer (pH 7.4) for 10 min. Subsequent treatments included dehydration, clearance, and coversliping of co-cultures with DePeX® (Serva, Heidelberg, Germany) for DAB-treated OTCs, or Fluoromount® (BDH Lab, Poole, England).

Results: Thalamocortical Cell Bridge is of Neuronal Origin

Figure 7:
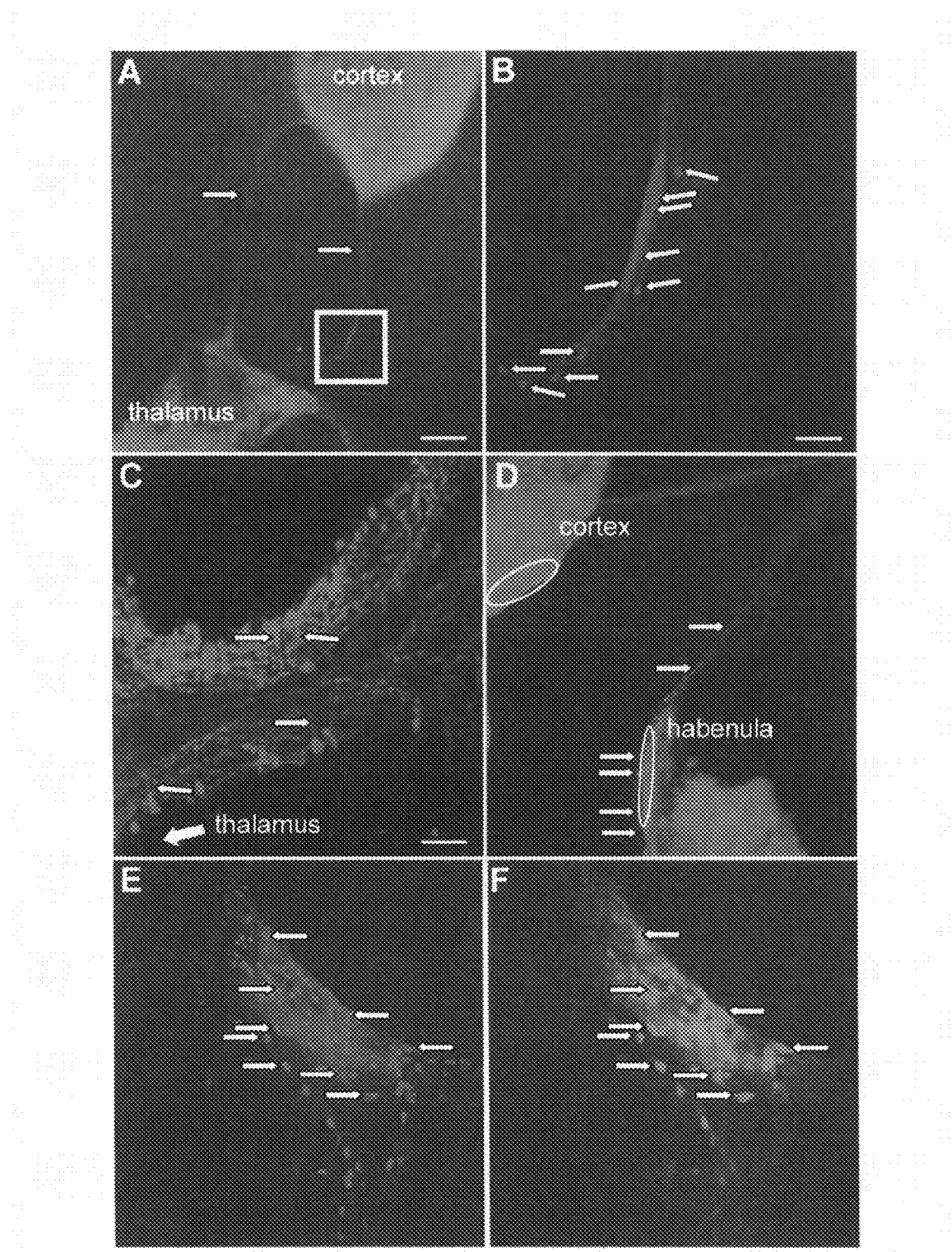
FIG. 7 shows production of a thalamocortical cell bridge after 4 days in vitro. Co-cultures were supplemented with 3 nM highly purified NRP-1.
Figure 8:
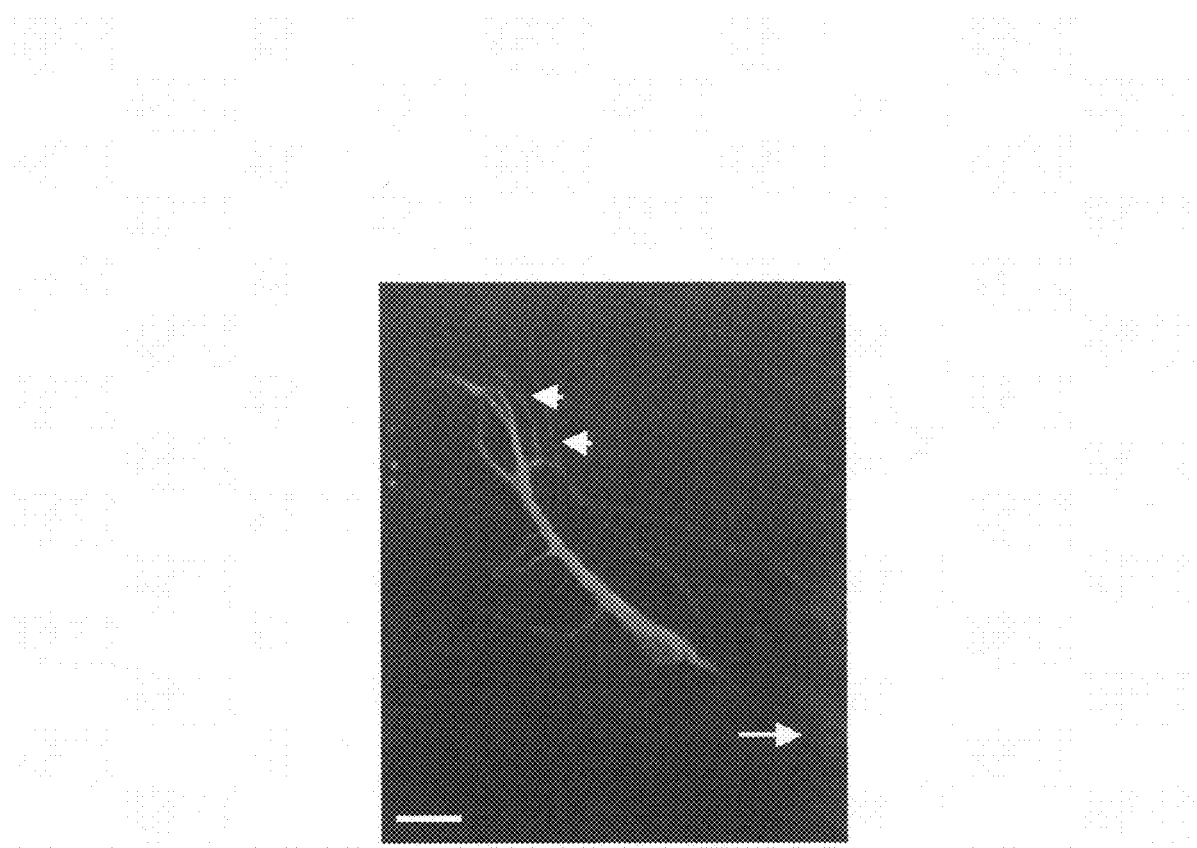
FIG. 8 is a photomicrograph showing enhancement of cellular expression of MAP-2 and correlation to the migration process. Strong MAP-2 expression can be observed within the apical neurite of the migrated cortical neuron, which was the leading process at the initiation of migration. The white arrow indicates the location of cortical layer I is about 500 μm. Note the existence of secondary and tertiary dendrites (arrowheads). Bar: 40 μm.

Migrating cells within the thalamocortical cell bridge were found to be of neuronal origin. FIG. 7C shows that MAP-2-ir cells formed a highly ordered structure at the thalamic origin. A row of MAP-2-ir neurons formed the margin of the cell stream that was different from the single cell chain migration observed in FIG. 7. The neurons at the margin, projected with their apical dendrite towards the middle of the migrating cell stream accompanied by neurite structures (FIG. 7C. The neurons of the regenerated cell bridge possess high levels of MAP-2 protein. MAP-2 was strongly expressed within the leading apical neurite (FIG. 8) of a migrating neocortical neuron. Within the thalamic migrating cell stream, a subpopulation of MAP-2-ir neurons were co-localized with the calcium binding protein parvalbumin (see FIGS. 7A, B and FIG. 9). Parvalbumin is a late postnatal marker of neuronal differentiation in the thalamus and can detect inhibitory cells of the thalamic reticular formation as well as excitatory thalamic projection neurons (Sieg et al., 1998). FIGS. 7E and 7F revealed that proliferative cells within the cell bridge are partially co-localized with parvalbumin. This finding indicates that NRP-1 stimulates early differentiation of parvalbumin-positive neurons in the thalamic cell bridge. Thus, the proliferating cells were of neuronal origin and the NRP stimulated neuronal proliferation and differentiation.

We conclude that the ability of NRP-1 to induce neuronal proliferation, migration and early differentiation indicates many therapeutic applications of NRP compounds in restoring neuronal networks which degenerate in neurodegenerative diseases and injuries. This example also supports the conclusion that the novel assay systems of embodiments of this invention provide sensitive, rapid and selective methods for detecting and quantifying activity of NRP compounds.

Example 4

In Vitro Assay for Evaluating Migration-Inducing Activity II

Figure 2:
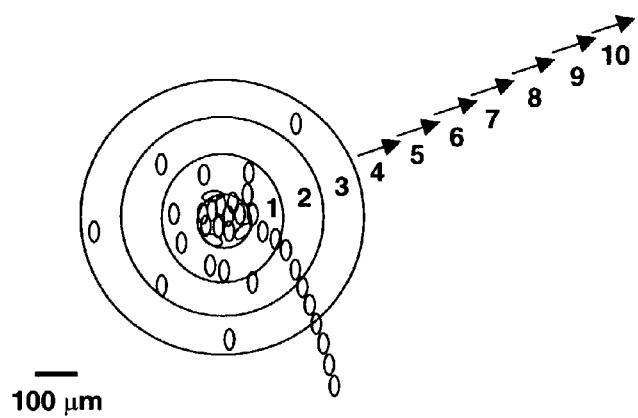
FIG. 2 depicts a schematic diagram of methods used to quantify neuronal migration within cerebellar microexplants. A transparent overaly comprising ten consecutive rings of 100 μm diameter was laid around a microexplant. To calculate the percentage of migrating cells, all cells within a respective consecutive ring were counted and divided by the total number of cells distributed in rings 1 to 10.

Another assay of this invention includes embodiments comprising cerebellar microexplants. Laminated cerebellar cortices of the two hemispheres were explanted from a P4 Long Evans rat, cut into small pieces in GBSS with 0.65% D(+)glucose solution, and triturated by a 0.4 mm gauge needle and subsequently pressed through a 125 µm pore size sieve. The obtained microexplants were centrifuged (200×g) 2 times for a medium exchange into serum-free BSA-supplemented START V-medium (Biochrom). Finally, the microexplants were reconstituted in 500 µl STARTV-medium. For culturing, 38 µl of the cell suspension and 2 82 l of migration-inducing factor (NRP-1) in 0.01 M sodium phosphate (pH 7.3) or phosphate alone (control) was incubated for 3 hours on a poly-D-lysine-coated cover slip in a 35 mm petri dish under an atmosphere comprising 5% $CO_2$ in air and 100% humidity at 34° C. Subsequently, 1 ml of STARTV-medium was added, and the cultures were evaluated after 2-3 days of culture (see FIG. 2).

For immunohistochemistry and neuronal migration experiments, cerebellar microexplants were fixed after 2-3 days in culture after the following regime: microexplants were fixed by 2-minute, serial treatment with 0.4%; 1.2%; 3% paraformaldehyde/0.25% glutaraldehyde, respectively, followed by a 5 min incubation in 4% paraformaldehyde/0.25% glutaraldehyde in 0.1 M sodium phosphate (pH 7.4). MAP-2 was detected using the biotin-streptavidin/Cy3 detection system as described under the immunohistochemistry section of the thalamocortical OTCs.

Statistical Analysis

Microexplants having a diameter between 100-120 µm were chosen for statistical analysis. For quantitative analysis of neuronal migration, an optical device having 10 consecutive rings of 100 µm diameter was applied over the microexplants. All neurons that had migrated after 48 h of culture were counted. Neurons located between circles 1 to 10 (0.1-1 mm) around the margin of the respective microexplant (see FIG. 2) were counted, and each circle was expressed as a percentage of total migrating cells. The unpaired Student's t-test was used for significance analysis. Results were given as mean values +/− standard deviation.

Results: Induction of Cerebellar Cell Migration Within a Microexplant System

Figure 13:
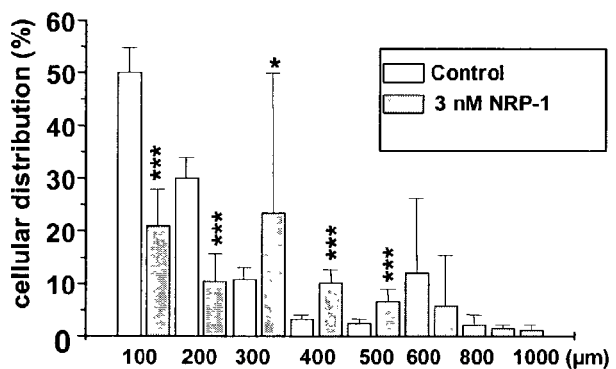
FIG. 13 depicts quantification of induction of cerebellar migration. Two days after NRP-1 administration there was a massive induction in cerebellar cell migration. Most of the cells were distributed between 200-300 μm from the cerebellar margin. A significant population of cells was distributed about 500-600 μm away from the margin. Cells from vehicle-treated cultures revealed a maximal distribution of 300 μm. The experimental data was derived from nine evaluated microexplants originating from three different cultures.
Figure 14:
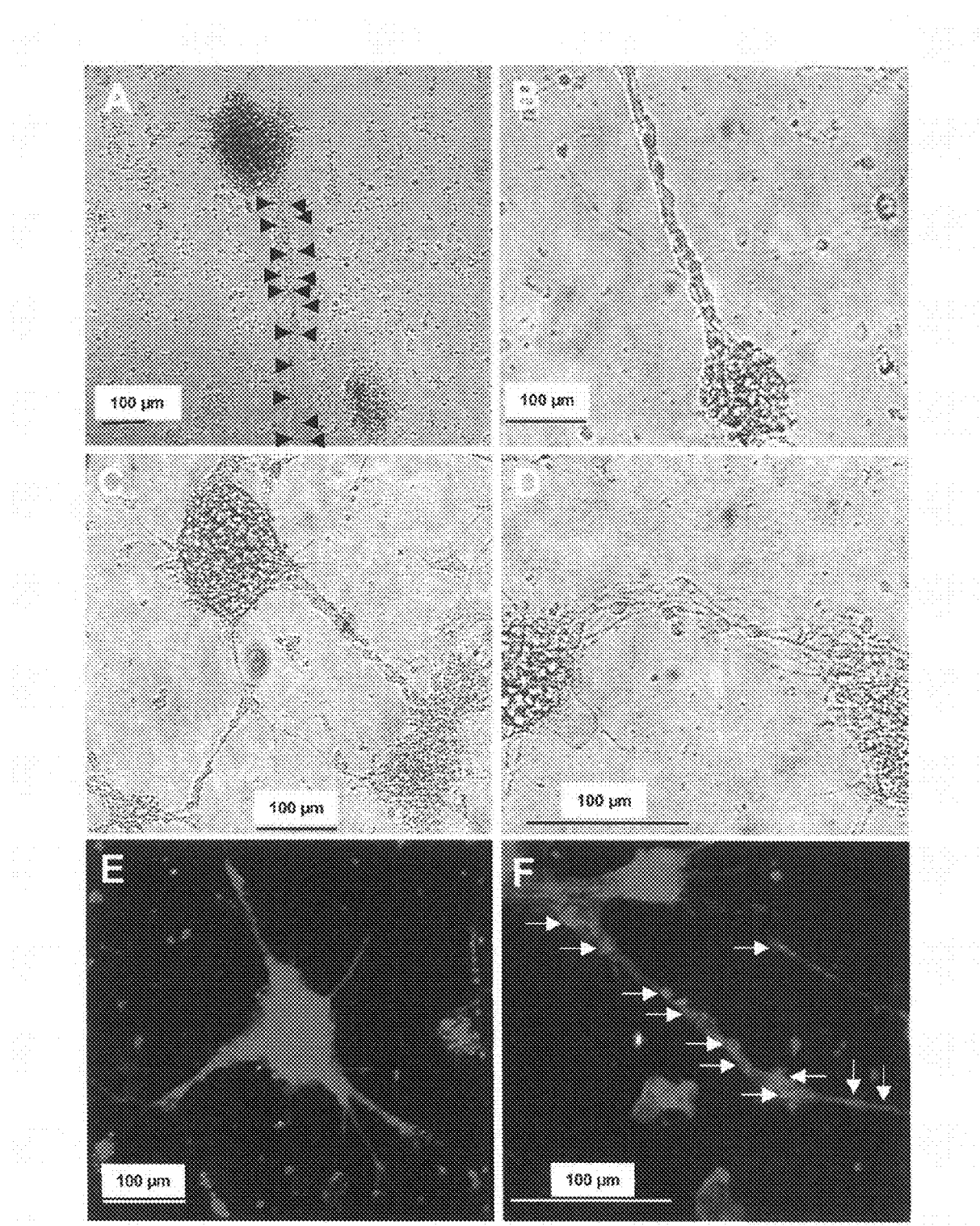
FIG. 14 depicts neuronal migration within cerebellar microexplants. The microexplants were supplemented with 75 nM purified NRP-1 after 3 h settling time on cover slips. At start of co-culturing (addition of cell medium) NRP-1 was added at a final concentration of 3 nM.

A concentration of 3 nM of purified NRP-1 was sufficient to induce a significantly enhanced migration of neurons within the cerebellar microexplant system. The number of migrating cells was in the range of 30 and 140 cells measured up to a distance of 1000 µm away from the margins of explants having diameters of from 100-120 µm. A highly significant (p<0.001) population of 7.3±2.8% of migrating cerebellar cells were distributed between 400-500 µm, and 13.2±13.9% of migrating cerebellar cells were distributed between 500-600 µm away from the microexplant margin after 2 days of culture with NRP-1 (see FIGS. 13 and 14). The vehicle-treated (0.01 M sodium phosphate) controls revealed neuronal migration to a certain extent (not significantly better than factor-treated samples over 200 µm migration distance). This relatively minor migration may be because in early postnatal cerebellar tissue, the final migration process to form the cerebellar granule cell layer had not been completed. Therefore the granule cells of P4 animals revealed some intrinsic neuronal migration activity when cultured. Nevertheless, we found that purified NRP-1 caused a substantial increase in both the number of migrating cells as well as the distance travelled.

Similar cerebellar granule cell migration has been induced by activation of $AT_2$ receptor of angiotensin II that is highly expressed in early postnatal cerebellar neurons (Cote et al., 1999). After $AT_2$ receptor activation using the highly effective agonist CGP42112 the longest migration distances were around 550 µm measured 96 hours after start of cultivation. The migration-inducing factor confers similar migration distances to the cerebellar microexplants although there exist two major differences to the angiotensin II-induced migration pattern. First, angiotensin does not induce neuronal chain migration like NRP-1 does and secondly the whole process of neuronal migration is considerably slower when induced by angiotensin II.

Thus, we conclude that NRP-1 -induces neuronal migration a separate, novel mechanism, and not by way of angiotensin II receptors. The ability of NRP-1 to induce neuronal migration indicates an application for NRPs in restoring neuronal networks damaged by neurodegenerative diseases and injuries.

Example 5

Induction of Neuronal Proliferation Within the Thalamocortical OTCs

Thalamocortical OTCs from rats, as described above in Examples 3 and 4 were incubated at the start of cultivation with 2 µM of BrdU that was removed after 24 hours of cultivation time. OTCs were fixed in 4% paraformaldehyde in 0.1 M phosphate buffer (pH 7.4). Blocking was done in 0.4% Triton and 10% normal goat serum in PBS for 30 minutes. Subsequently the cultures were treated for 30 minutes in 2N HCl at 37° C. and neutralized by 0.1 M $Na_2B_4O_7$ for 2×5 minutes. Internal peroxidase activity was prevented by 5 minute treatment of the OTCs in 1% $H_2O_2$ (only in case of the PAP reaction). Primary antibody (mouse anti-BrdU 1/50-Sigma) reaction was done overnight in 0.4% Triton, 2% BSA in PBS.

Biotinylated goat anti-mouse IgG was applied (1/200 for 2 h) with the subsequent application of the avidin biotin horseradish peroxidase system and the final DAB-detection (0.05%); 0.009% $H_2O_2$ enhanced by 0.025% cobalt chloride and 0.02% nickel ammonium sulphate. BrdU-positive nuclei become black stained. After three PBS washes, the rabbit anti-parvalbumin IgG (1/1000) was applied overnight at room temperature in 0.4% Triton; 2% BSA in PBS followed by the goat anti-rabbit (1/100) in the same buffer. Subsequently, follows the PAP reaction in PBS (rabbit PAP 1/200) developed by the DAB-reaction. The parvalbumin-ircytoplasm becomes brown stained. OTCs were coverslipped with DePeXe. For double fluorescence detection, mouse anti-BrdU IgG and rabbit anti-parvalbumin IgG (or rabbit anti-calretinin 1/1000) were given simultaneously after the neutralisation step and anti-parvalbumin antibody binding was detected by the biotin-streptavidin/Cy2 detection system while the occurrence of BrdU was monitored by an anti-mouse/Cy3 IgG. These fluorescent OTCs were coverslipped with Fluoromount®.

Statistical Analysis

Figure 9:
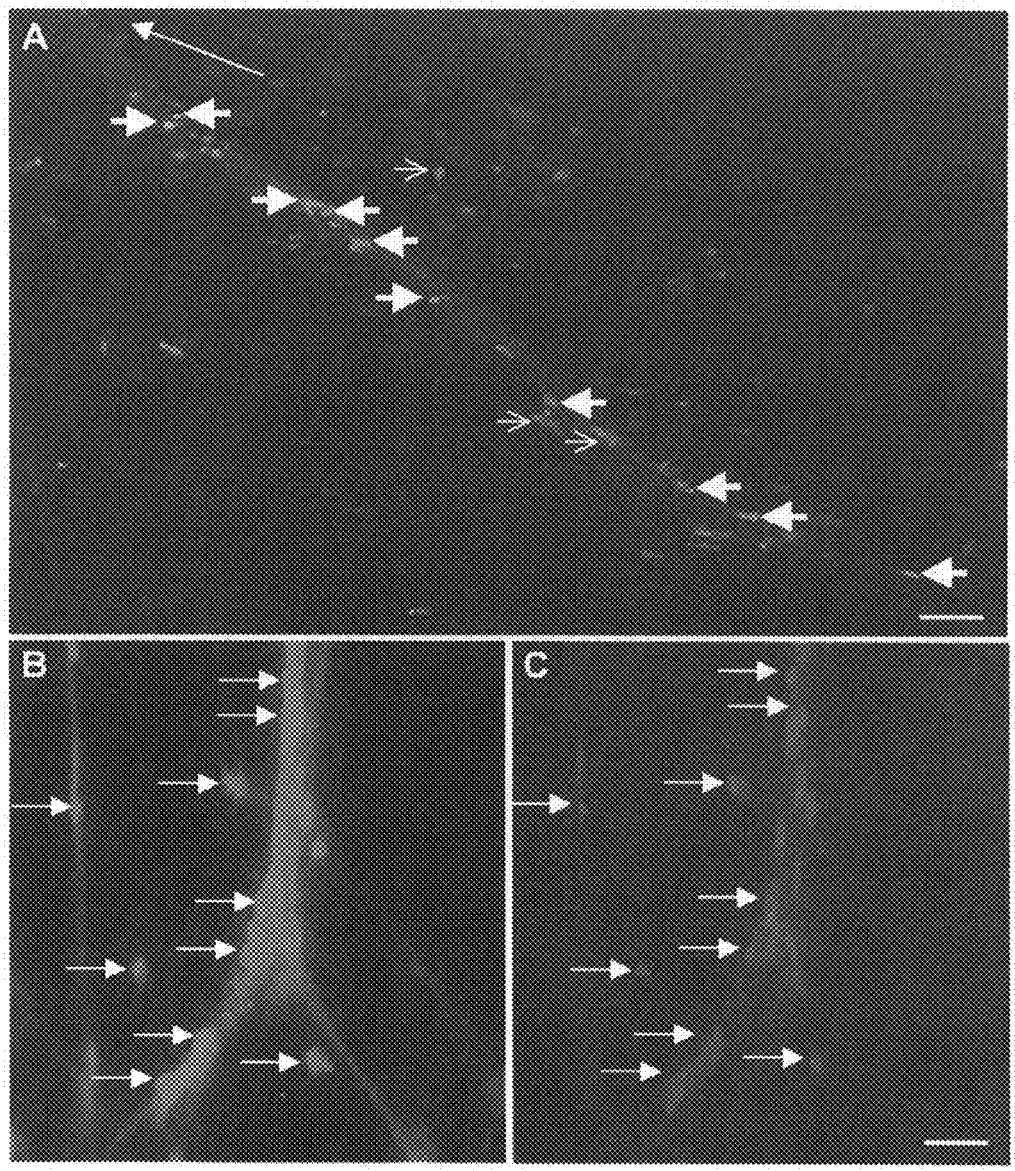
FIG. 9 is a series of photomicrographs showing proliferation and migration of parvalbumin-ir thalamic neurons inbetween the thalamic and cortical tissue of the thalamocortical co-cultures. Thalamocortical OTCs were supplemented with 3 nM of highly purified NRP-1 and BrdU for 24 hours and fixed following 4DIV.

For quantitative analysis of the parvalbumin/BrdU co-localization within thalamic tissue, a DAB/PAP reaction system was used, because double-fluorescence techniques can be characterized by quenching effects in dense tissues and thus are well suited for cellular monolayers (see FIG. 9). We counted all parvalbumin-ir cells within 5 factor-treated and 5 control cultures. Subsequently, the double-positive cells (parvalbumin-ir cells that contain a BrdU-positive nucleus) were counted, and results were expressed as a percentage of the total thalamic parvalbumin-ir neuronal cell population. The unpaired Student's t-test was used for significance analysis. Results are given as mean values ± standard deviation.

Results

Figure 10:
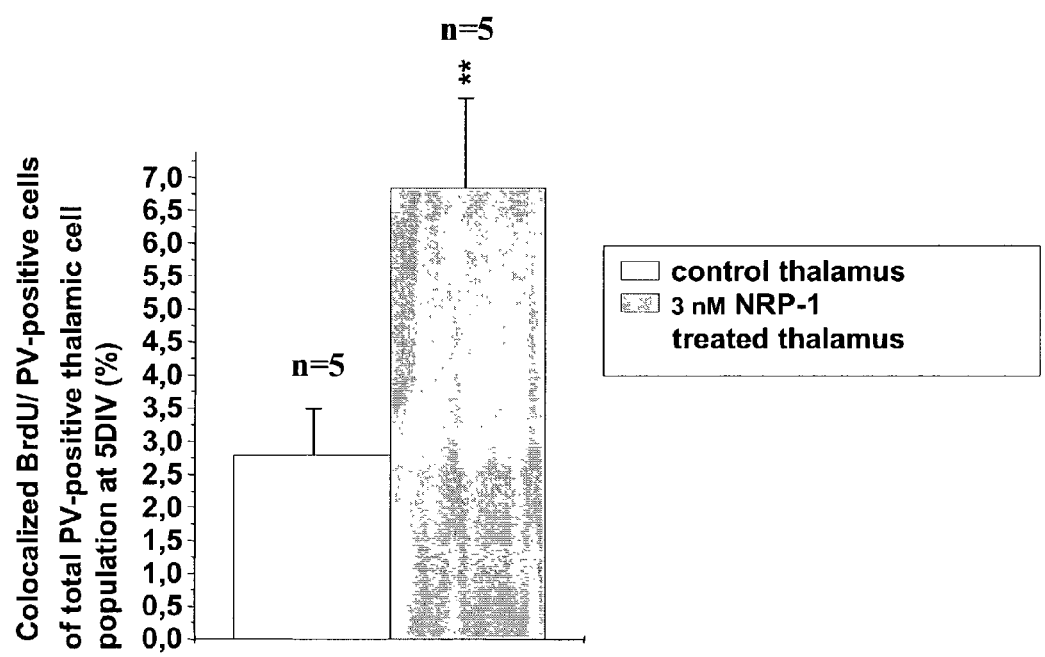
FIG. 10 depicts a graph showing quantitative analysis of proliferation initiation within thalamic parvalbumin-ir neurons. BrdU and 3 nM NRP-1 were administered at the start of co-culturing. The medium was changed after 24 hours. Co-localisation of parvalbumin and BrdU was estimated after 5 days in vitro within the thalamic tissue, which included the habenula nucleus, the lateral geniculate nucleus, the nucleus reticularis thalami and thalamic midline nuclei. 6.8% of the total parvalbumin-ir thalamic population was of proliferative character. NRP-1 induced strong proliferation induction compared to the vehicle. N represents the number of assessed thalamic tissues.
Figure 11:
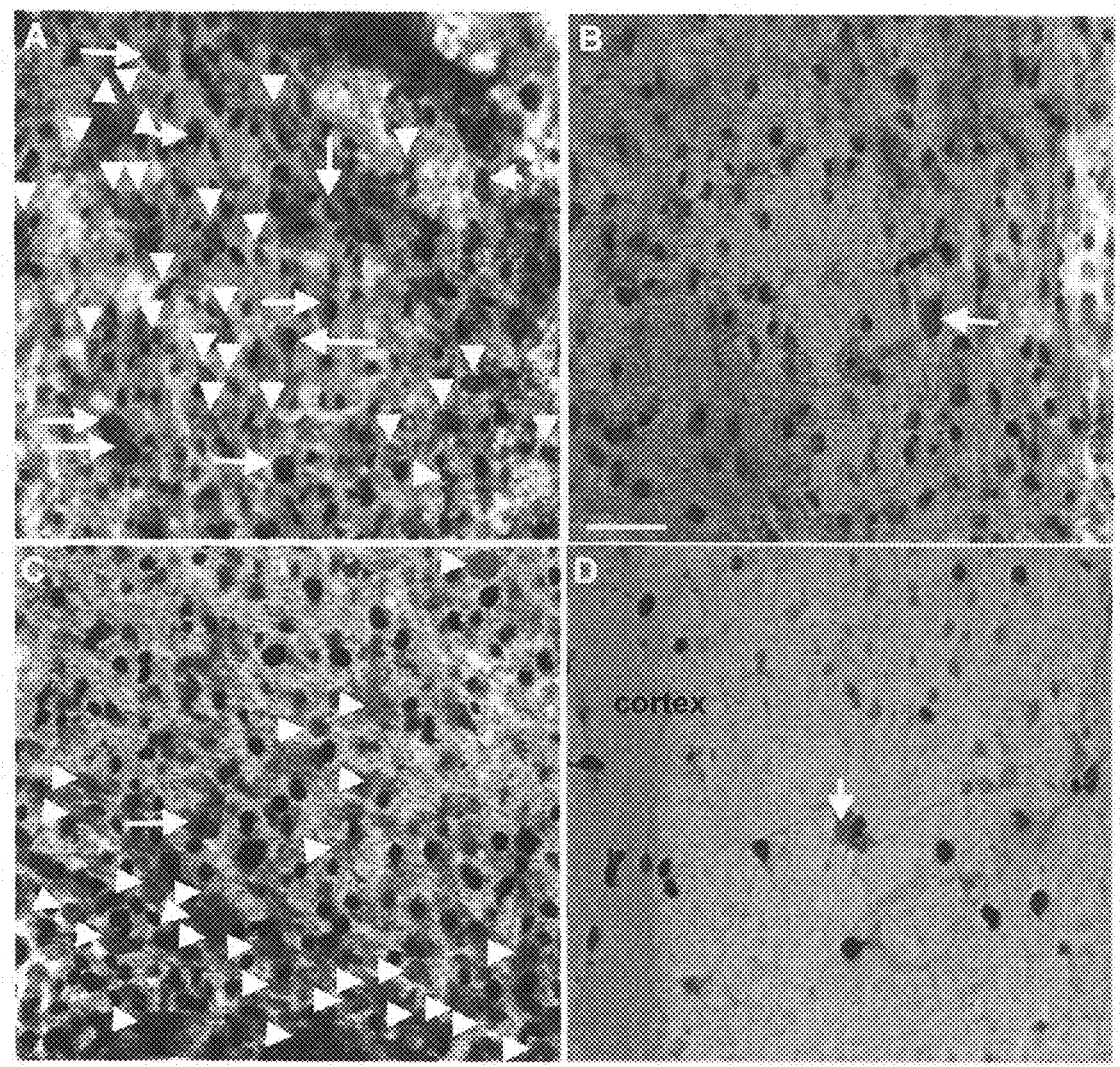
FIG. 11 depicts quantification of proliferative parvalbumin-ir cells within thalamic tissue. 5 days after NRP-1 administration there was a distinct induction of proliferation (white arrows) within parvalbumin-ir cells within central areas of the thalamus. The majority of parvalbumin expressing cells remained non-proliferative (arrow heads in FIG. 11A). Inside the habenula nucleus, only a minority of parvalbumin expressing cells are double labelled with BrdU (FIG. 11B). In vehicle treated cultures double-labelled BrdU parvalbumin expressing cells were found very rarely (arrow in FIG. 11C).

Neuronal expression patterns of newly formed cell bridges were detected using parvalbumin, calretinin, or MAP-2 positive immunological reactions. These showed that neuronal cells partly co-localized with BrdU, indicating that these neurons were in the S-phase of the cell cycle. Another subpopulation of cells within the cell bridge exhibited a strong MAP-2, calretinin or parvalbumin expression and were not positive for BrdU (FIG. 9A). Although the mechanism is not known with certainty, one theory is that these cells have completed migration and went off the S-phase to differentiate into their distinct neuronal cell types. We studied the cell cycle status in cultures having BrdU added at the beginning of culturing 4 days after administration of the migration-promoting factor. The number of parvalbumin expressing neurons in the thalamus was between 500 and 700 cells within control and factor treated tissue. Double-staining experiments using anti-parvalbumin antiserum and anti-BrdU antibody revealed that NRP-treated thalamic areas have 6.8±1.3% ($p<0.01$) of their parvalbumin-ir neurons co-localised with BrdU, whereas controls (medium only) revealed only 2.7±0.7% of parvalbumin-ir neurons in a proliferative state after 5 days in culture (see FIGS. 10 and 11). The control value of 2.7% proliferating parvalbumin expressing neurons represented the basal level of these neurons after the traumatic event of the initial cultivation. Administration of NRP-1 (3 nM) to the thalamocortical OTCs enhanced proliferation of parvalbumin expressing neurons within the thalamic tissue up to 150% compared to controls treated with defined medium alone. A more pronounced proliferation rate was observed within the newly formed (migrated) cell bridge where the majority of parvalbumin expressing neurons were of a proliferative state (FIGS. 7E and F and FIG. 9).

Figure 12:
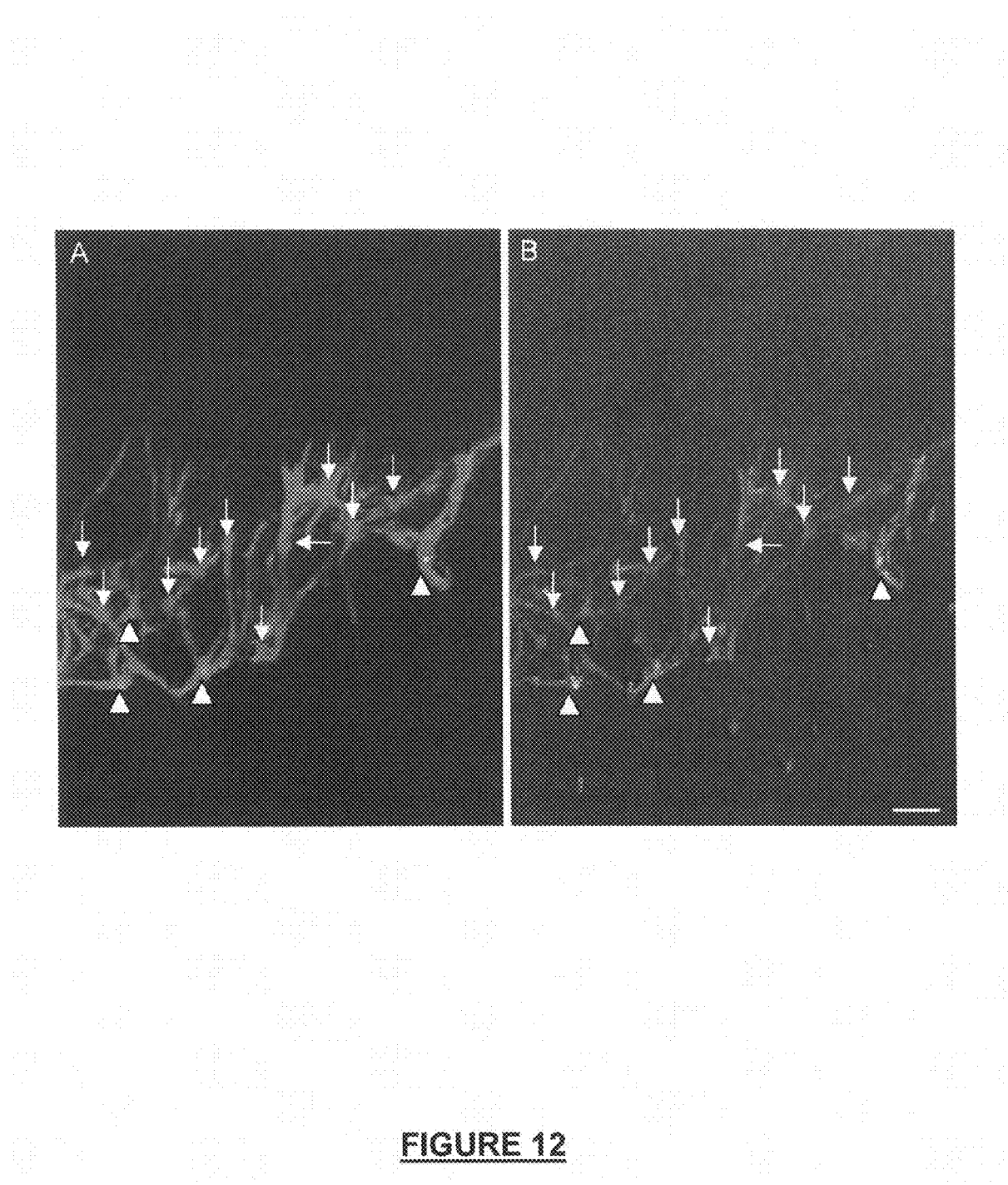
FIG. 12 depicts the specificity of the proliferation induced by NRP-1. We tested the proliferation status of astroglia by monitoring the expression patterns for GFAP and BrdU-incorporation. Thalamocortical OTCs were supplemented with 3 nM highly purified migration-inducing factor and fixed following 4 days in vitro.

We also investigated the effects of NRP-1 on the induction of proliferation within astrocytes in a qualitative way. Standard organotypic tissue cultures exhibit increased numbers of reactive astrocytes, which may appear due to the traumatic event of the tissue extraction process. Therefore we looked only at the newly formed cell bridge between the thalamic and cortical tissue 4 days after NRP administration. We found that only a small subpopulation of astrocytes that express GFAP reveal incorporation of BrdU (see FIG. 12).

Purified NRP-1 preferably induces neuronal proliferation but does not induce astroglial division. Thus, we conclude that NRPs are effective agents and can cause neurons to proliferate. The results also indicate applications for NRPs and paralogs or fragments in the treatment of neurological conditions and spinal cord injuries in which neural tissue is damaged or has degenerated, for example Huntington's disease, Parkinson's disease and paraplegia. The results further indicate that NRPs have an application in improving outcomes of neural replacement therapies, such as in transplantation.

Example 6

Effects of Synthetic NRPs on Cerebellar Microexplants

To ensure that the effects observed with purified NRPs originating from tissue cultures were due to the NRPs themselves and not due to contaminants or other materials in the materials, we carried out a series of studides using synthetic NRPs. NRPs were supplied by Auspep (Australia). They were supplied with an amidated C-terminus, and were more than 95% pure as analyzed by MALDI-MS spectrum analysis. The mouse NRP (arachne contig 191157 mouse; SEQ ID NO: 17; SEQ ID NO: 18) was 91% pure. The peptides were stored lyophilized at −80° C. under argon until usage. They were reconstituted in PBS, alternatively in 100 μg/ml human transferrin/PBS or in other embodimens in 100 μg/ml BSA/PBS and further diluted in PBS having 10 μg/ml of BSA or transferrin before further use within the different assays.

1. Cerebellar Microexplant System for Determination of Survival and Proliferation Inducing Activity of the NRPs Toxicological and drug administration experiments were designed such that 1/100 parts of toxin and neuroprotective drug were administered simultaneously to the freshly prepared cerebellar microexplants derived from P4 or P8 rats. Glutamate was prepared as a 50 mM stock solution in MilliQ water while 50 mM 3-nitropropionic acid was pH-adjusted (pH 6.8-7.2) in MilliQ water. The concentration of the oxidative stress inducing toxin, 3-nitropropionic acid (3-NP), and the excitotoxin, glutamate, in the assay were 0.5 mM each. Lyophilized peptides were reconstituted in PBS or 100 μg/ml human transferrin as a 10 μM stock solution. Subsequently, serial dilutions were made. Cerebellar microexplants were cultivated for 48-72 hours at 34° C., 5% $CO_2$ in air and 100% humidity before they were fixed by increasing amounts of paraformaldehyde (0.4%, 1.2%, 3% and 4% -each treatment 2-3min).

Using the toxins described above, cerebellar explants were exposed for 24 hours, at the beginning of culturing to dilutions of NRP and 0.1 μM BrdU. Subsequently, 80% of the medium was changed without addition of new toxins and NRP's. The cerebellar cultures were fixed as described above after 3 days in vitro. The detection of the incorporated BrdU level was performed as described previously. Under these conditions, over 99% of the cerebellar cell population were neurons. Therefore any increase in cell number after NRP administration was most likely due to neuronal cell proliferation.

Analysis: Neuronal Survival and Proliferation Assays

For statistical analysis of survival, four fields (each field having an area of 0.65 mm$^2$) of each fixed cerebellar culture with the highest cell densities were chosen, and cells displaying neurite outgrowth were counted. Statistical significance was measured by Student's t-test.

For statistical analysis of proliferation four fields (each field having an area of 0.65 mm$^2$) of each fixed cerebellar culture displaying highest density of BrdU-positive nuclei were chosen, and BrdU-positive nuclei were counted. Statistical significance was measured by Student's t-test.

2. Haptotactic Migration Assay

To test the cell adhesion and neuronal migration inducing properties of the paralog peptides simultaneously a haptotactic migration cell assay was developed (Lu et al., 2001). For this purpose Transwell® cell culture dishes (Costar) with fitting inserts consisting of 12 μm pore size were used to cultivate striatal and neocortical cells.

The inserts were coated with PDL (0.1 mg/ml in PBS—cell culture tested grade from Sigma) for 15 minutes at room temperature. The culture dishes were first coated with NRP-1 compounds. For this purpose a 19mer form (NRP-11; KDPEARRAPPGSLHPCLAAS; SEQ ID NO: 23) of the annotated human NRP encoded by a nucleotide sequence located on chromosome 13 (SEQ ID NO:4) and a 24 mer form of NRP-mfs (NRP-12; SEPEARRAPGRKGGVVCASLAADW: SEQ ID NO:24:) of the annotated mouse arachne contig__191157 gene NRP ortholog (SEQ ID NO: 16) were chosen. The lyophilised peptides were reconstituted in 100 μg/ml human transferrin or bovine serum albumin (BSA) in PBS and further NRP dilutions were made in the presence of 10 μg/ml of the respective proteins. Peptide concentrations between 0.01-1 μg/ml were used as well as blank transferrin and BSA controls. The final amount of the NRPs were between 15 and 1500 ng/110 mm$^2$. The peptide coating was carried out for 2 hrs at 37° C. After a PBS wash the culture dishes were subsequently coated with PDL (0.1 mg/ml) for 2 hrs at 37° C. followed by a PBS wash.

For seeding striatal cells, 1.5 ml of Neurobasal/B27 medium was put into the culture dishes and 0.5 ml of Neurobasal/B27 medium was put into the insert. The assay was ready for cell seeding. For the seeding of cortical cells, 50% of Neurobasal/B27 medium and 50% of astrocyte conditioned medium were added to culture dishes and inserts before the seeding of the cells.

Preparation of Striatal Tissues

For the preparation of striatal tissue from rat E18/E19 embryos, the dam was sacrificed by $CO_2$-treatment in a chamber for up to 4 minutes, and was then prepared for caesarean section. After surgery the embryos were removed from their amniotic sacs, decapitated and the heads were put on ice in DMEM/F12 medium for striatum and PBS plus 0.65% D(+)-glucose for cortex preparation. The whole brain was removed from the skull with the ventral side facing upwards in DMEM/F12 (Invitrogen) medium. The striatum was extracted under a stereoscopic microscope, by dissecting out the striatum from both hemispheres, which was then placed into the Falcon tube on ice.

The striatal dissection for both hemispheres was performed as follows; the embryonic brain was placed ventral side down, rostral end forward. Along the midline one hemisphere was gently pulled open using fine forceps. A frontal rostral cut was performed to expose the inner region (the striatum) that was located rostral-centre within the cortical cavity. The striatum was pinched out using the forceps and taking care not to avoid the underlying cortex. Tissue pieces were placed into a Falcon tube on ice. The collected striatal tissue was triturated using a P1000 pipettor in 1 ml of medium. The cells were triturate by gently pipetting the solution up and down into the pipette tip about 15 times, using shearing force on alternate outflows. The tissue pieces settled to the bottom of the Falcon tube within 30 seconds, and subsequently the supernatant was transferred to a new sterile Falcon tube on ice. The supernatant contained a suspension of dispersed, dissociated cells. The tissue pieces were exposed to a second round of trituration by adding 1 ml of ice-cold DMEM/F12 medium to the tissue pieces in the first tube and triturating as before. In so doing, we did not excessively damage cells already dissociated. The tissues pieces were allowed settle and the supernatant removed to a new sterile Falcon tube on ice. The cells were centrifuged at 250 g for 5 minutes at 4° C. The resuspended cell pellet was used for cell counting.

Preparation of Cortical Astrocyte Cultures

One cortical hemisphere was used from P1 rats and collected into 4ml of DMEM. Trituration was done with a 5 ml glass pipette and subsequently through an 18-gauge needle. Afterwards, the cells were passed through a 100 μm cell strainer and then washed in 50 ml DMEM, followed by centrifugation for 5 min at 250 g. The sediment was resuspended into 20 ml DMEM+10% fetal calf serum. 10 ml each were added into two 25 cm$^2$ flasks. They were cultivated at 37° C. and 10% $CO_2$ with a medium change twice weekly. After cells reached confluence they were washed three times with PBS and adjusted to Neurobasal/B27 and incubated for another 3 days. The supernatant was frozen at −80° C. for transient storage until use.

The cortical tissue was extracted from E18/19 rat embryos. The two cortical hemispheres were carefully removed by a spatula from the whole brain with the ventral side facing upwards into a PBS+0.65% D(+)-glucose containing petri dish. Forceps were put into the rostral part (near B. olfactorius) of the cortex for fixing the tissue and two lateral— sagittal oriented cuttings were done to remove the paraform and entorhinal cortices. The next cut involved a frontal oriented cut at the posterior end to remove the hippocampal formation. A final frontal cut was done a few millimeters away from the last cut in order to get hold of area 17/18 of the visual cortex.

The collected cortices were placed on ice in PBS+0.65% D(+)-glucose and centrifuged at 350 g for 5 min. The supernatant was removed and trypsin/EDTA (0.05%/0.53 mM) was added for 8 min at 37° C. The reaction was stopped by adding an equal amount of DMEM+10% fetal calf serum. The supernatant was removed by centrifugation followed by two subsequent washes in Neurobasal/B27 medium. Cells were triturated once with a glass Pasteur pipette in 1 ml of Neurobasal/B27 medium and subsequently twice more using a 1 ml syringe having a 22-gauge needle. The cell suspension was passed through a 100 μm cell strainer and subsequently rinsed in 1 ml of Neurobasal/B27 medium. Cells were counted and were ready for plating for the haptotactic migration assay.

Cell Culture Conditions for the Haptotactic Migration Assay 200,000 striatal or cortical cells in a volume of about 50 μl of volume were seeded into an insert and the whole assay of inserts was cultured at 37° C. in an atmosphere containing 5% $CO_2$ in air and having 100% humidity. After 24 to 48 hrs, cells were fixed as already mentioned with increasing amounts of paraformaldehyde as described above.

Statistical Analysis

All paraformaldehyde-fixed cells displaying neurite outgrowth, which had migrated at least 1 mm (located at the bottom of the culture dish), were counted 48 hrs after the start of cultivation. Student's t-test was performed to obtain significance values.

Figure 15:
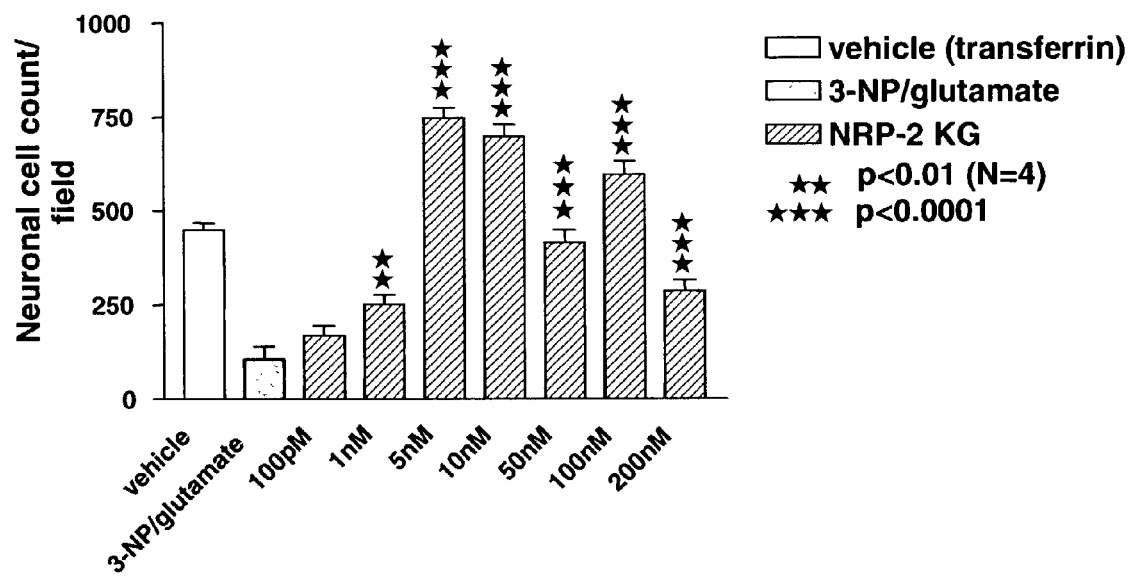
FIG. 15 depicts results of a survival assay with NRP-2 segment KG (human chromosome 13) using a pre-incubation method. Cerebellar microexplants were pre-incubated for 15 hrs with NRP-2 segment KG and subsequently injured by 3-NP/glutamate for 9 hrs. After 72 hrs neuronal survival was evaluated by counting cells displaying neurite outgrowth. Using between 5-100 nM NRP hc 13 fully reversed the effect of the injury. 5, 10 and 100 nM concentrations of NRP-2 segment KG hc 13 induced proliferation of the cultured neurons.

Results: Neuronal Cell Proliferation Inducing Activity and Neuronal Survival Activity and Neuronal Migration Inducing Activity For the testing of the biological activities of the human NRP located on chromosome 13 (amino acid sequence is shown in SEQ ID NO: 5), NRP-2 KG and NRP-2KS of the peptide were used. NRP-2KG is located between amino acids 20-43 of the annotated NRP amino acid sequence (SEQ ID NO: 5), and produces the peptide: KDPEARRAPGSLHPC-LAASCSAAG (NRP-2KG; SEQ ID NO: 18), and the 19mer form (NRP-2KS: SEQ ID NO: 25) is located between amino acid positions 20-38 in SEQ ID NO: 5. Preconditioning of cerebellar cultures with human NRP-2KG (FIG. 15) at a concentration between 5 to 100 nM for 15 hours resulted in complete neuroprotection from oxidative/excitotoxic injury. The data also showed that over a wide dose range, between 1-200 nM, NRP-2KG showed no cytotoxicity. At a concentration of 1 nM, NRP-2KG showed 42.4% recovery from 3-NP/glutamate injury, which was similar to the 46.0% recovery rate seen at 1 nM concentration in the injury, and human NRP-2KG (compare FIGS. 15 and 16). The effective dosage range of NRP-2KG was even bigger in injured cells, namely between 0.1 pM and 1 nM. In comparison, in uninjured cells the dosage range had biological effects between 5 nM and 100 nM.

Figure 19:
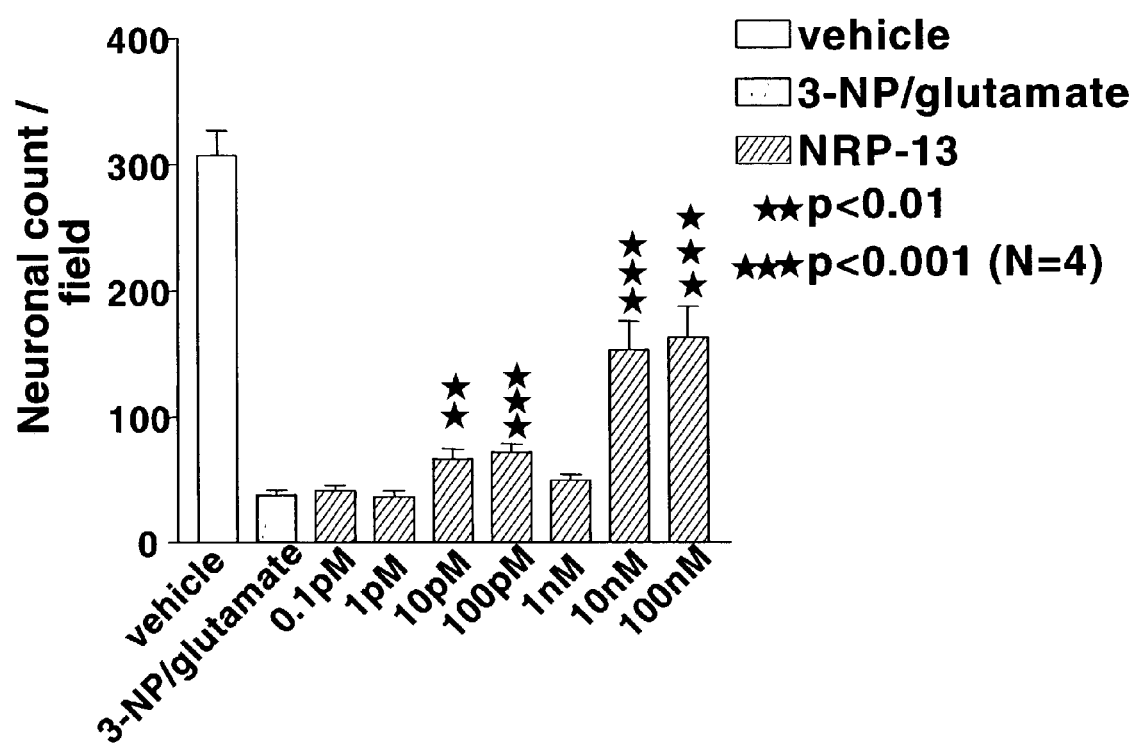
FIG. 19 depicts results of a survival study with human NRP-4 segment GQ. Cerebellar microexplants were injured by 3-NP/glutamate and simultaneously rescued by NRP-4 segment GQ (human chromosome 15). After 48 hrs neuronal survival was evaluated by counting cells displaying neurite outgrowth. The maximal biological activity of NRP-4 segment GQ for survival was between 10 nM and 100 nM.

Within the applied proliferation assay rat NRP-1 and NRP-2KS were tested for neuronal proliferation inducing activity (see FIG. 19). In order to discriminate proliferation from increased survival and cellular adhesion properties, NRP-2KS was administered 24 hrs after the start of cultivation. Rat NRP-1 has specific effects on neuronal proliferation, (see FIGS. 7, 9 and 10). Neuronal proliferation induced by NRP-2KS occurred within a range of about 0.3-30 nM using un-injured cerebellar microexplants (verified by counting cells displaying neurite outgrowth). The highest activity was observed at a concentration of 300pM, which produced increased neuronal cell proliferation, or 117.5% greater than vehicle-treated controls. Rat NRP-1 had its greatest effect at 3nM with 81.2% up regulation of neuronal cell proliferation (see FIG. 17).

For assaying chemoattractive activity of neuronal migration inducing factors a haptotactic migration assay (Lu et al., 2001) was applied. The human NRP-2KG was coated on Transwell® culture dishes in the presence of BSA or transferrin followed by PDL-coating. Seeded embryonic striatal cells migrated from the culture dish insert over a distance of 1 mm to the bottom of the culture dish. If the NRP-2KG was reconstituted in BSA, the migration inducing activity was non-significant, whereas NRP-2KG reconstituted in human transferrin and subsequent immobilization of 150 ng NRP-2KG caused 466.0% more neurons to migrate to the culture dish bottom after 2 days in vitro compared to transferrin control alone (see FIG. 18).

Figure 21:
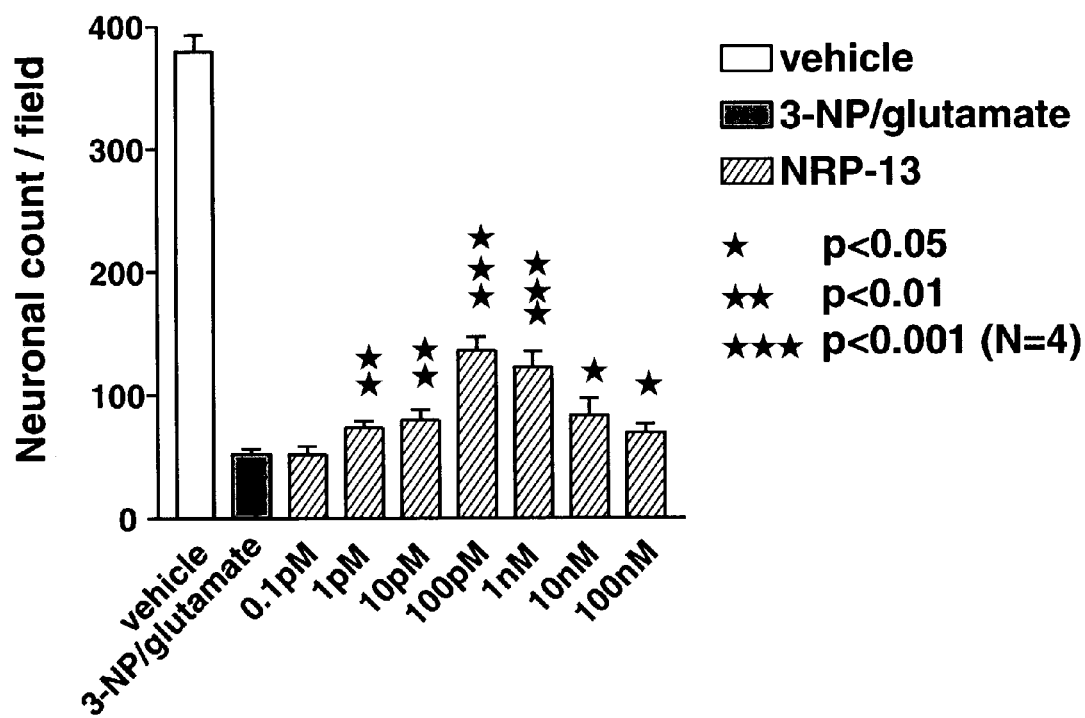
FIG. 21 depicts results of a survival assay with NRP-3 segment SQ (human chromosome 3). Cerebellar microexplants were injured by 3-NP/glutamate and simultaneously rescued by NRP-3 segment SQ. After 48 hrs neuronal survival was evaluated by counting cells displaying neurite outgrowth. Maximal biological activity of NRP-3 for survival was between 100 pM and 1 nM.

Biological activity of the human NRP located on chromosome 3 (SEQ ID NO: 6) was tested using an 11 mer peptide (NRP-13; SDSFKSQARGQ: SEQ ID NO:26) which is located between amino acids 13-23 of the annotated NRP protein encoding sequence (SEQ ID NO:6). NRP-13 elicited maximal biological activity between 100 pM and 1 nM applied within the cerebellar microexplant neurotoxicity assay (see FIG. 21). After 48 hrs, 100 pM of NRP-13 increased recovery from oxidative/excitotoxic injury by 27.7%.

Biological activities of the human NRP located on chromosome 15 (SEQ ID NO: 8) were tested using an 11 mer form of the peptide (NRP-14: GTPGRAEAGGQ: SEQ ID NO: 27), located between amino acids 22-32 of the annotated NRP protein encoding sequence. For neuronal survival, NRP-14 conferred maximal biological activity between 10-100 nM as measured in the cerebellar microexplant neurotoxicity assay. After 48 hrs, 100 nM NRP-14 produced recovery from oxidative/excitotoxic injury by an average of 46.3% (see FIG. 19).

Figure 20:
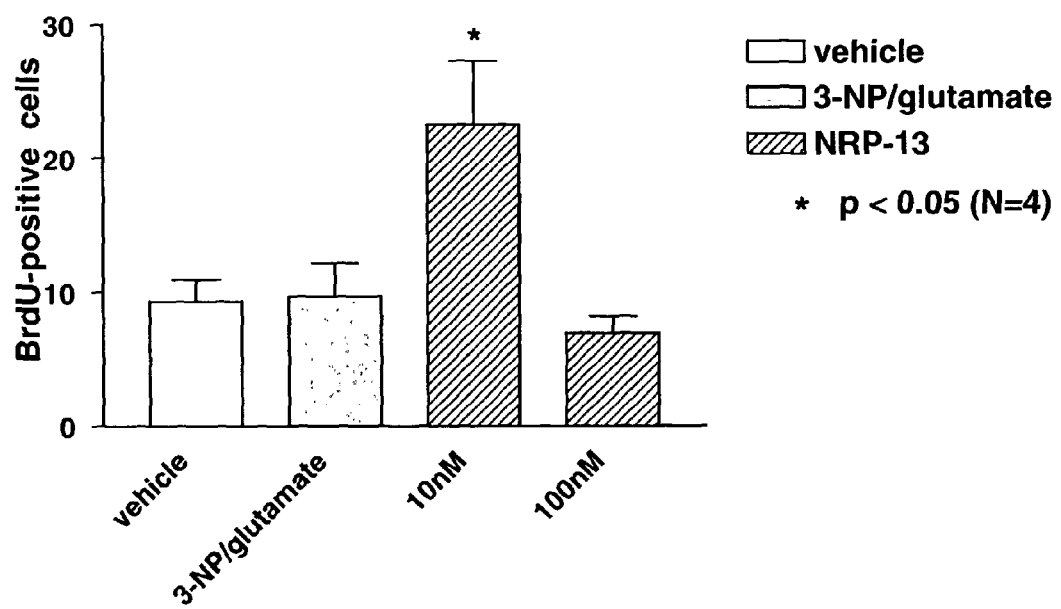
FIG. 20 depicts results of studies on proliferation induction under injury condition using NRP-4 segment GQ. Cerebellar microexplants were injured by 3-NP/glutamate. NRP-4 segment and BrdU were administered simultaneously for 24 hrs. After 72 hrs BrdU-positive nuclei were counted within four microscopic fields for each culture. Proliferation induction was observed at a 10 nM concentration of the peptide.

NRP-14 was also tested for neuronal proliferation inducing activity. Neuronal proliferation inducing activity of NRP-14 was observed at a concentration of 10 nM, and produced an up regulation of 132.2% in the proliferation rate compared to injured cerebellar microexplants (see FIG. 20). There was no difference between injured and non-injured (vehicle treatment) microexplants concerning the proliferation rate, which indicated that the 24 hr injury protocol did not produce reactive astrocytes.

Figure 22:
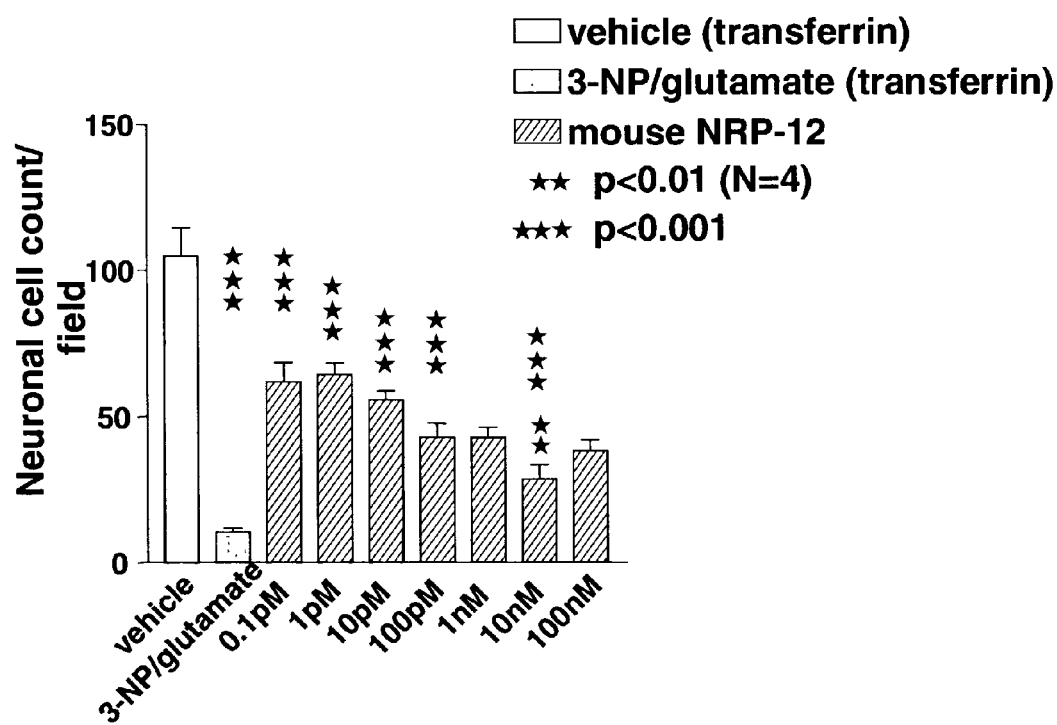
FIG. 22 depicts results of a survival assay with mouse NRP-7 segment SW. Cerebellar microexplants are injured by 3-NP/glutamate and simultaneously rescued by mouse NRP-7 in the presence of human transferrin. After 48 hrs neuronal survival is evaluated by counting cells displaying neurite outgrowth. Maximal biological activity of NRP-7 segment SW for survival was observed between 0.1 pM and 1 pM.
Figure 23:
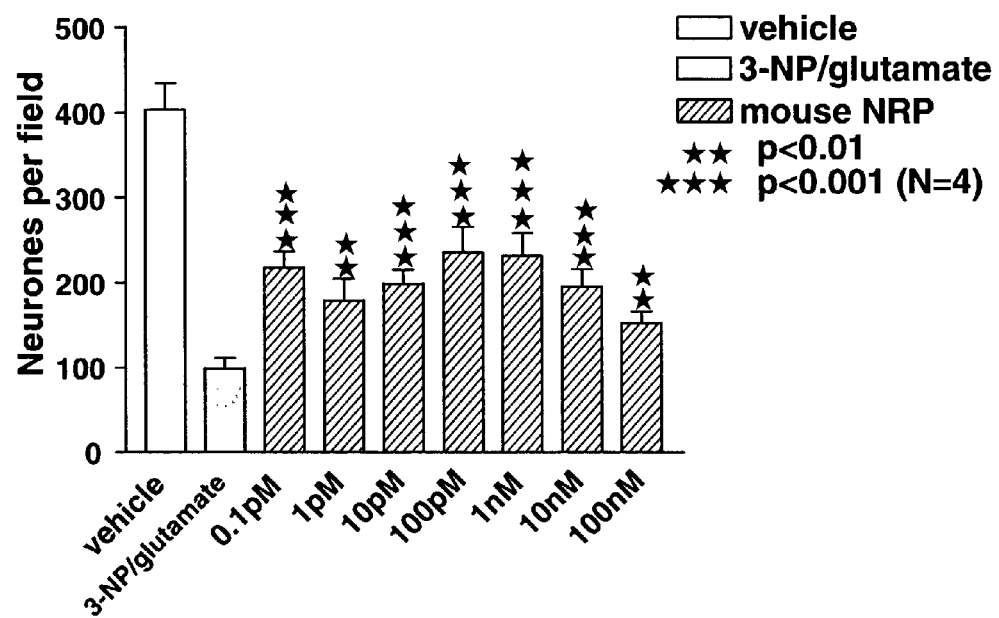
FIG. 23 depicts results of a survival assay with mouse NRP-7 segment SW. Cerebellar microexplants were injured by 3-NP/glutamate and simultaneously rescued by NRP-7 (SW) without transferrin. After 48 hrs neuronal survival was evaluated by counting cells displaying neurite outgrowth. Maximal biological activity of NRP-7 segment SW for survival was between 100 pM and 1 nM.
Figure 25:
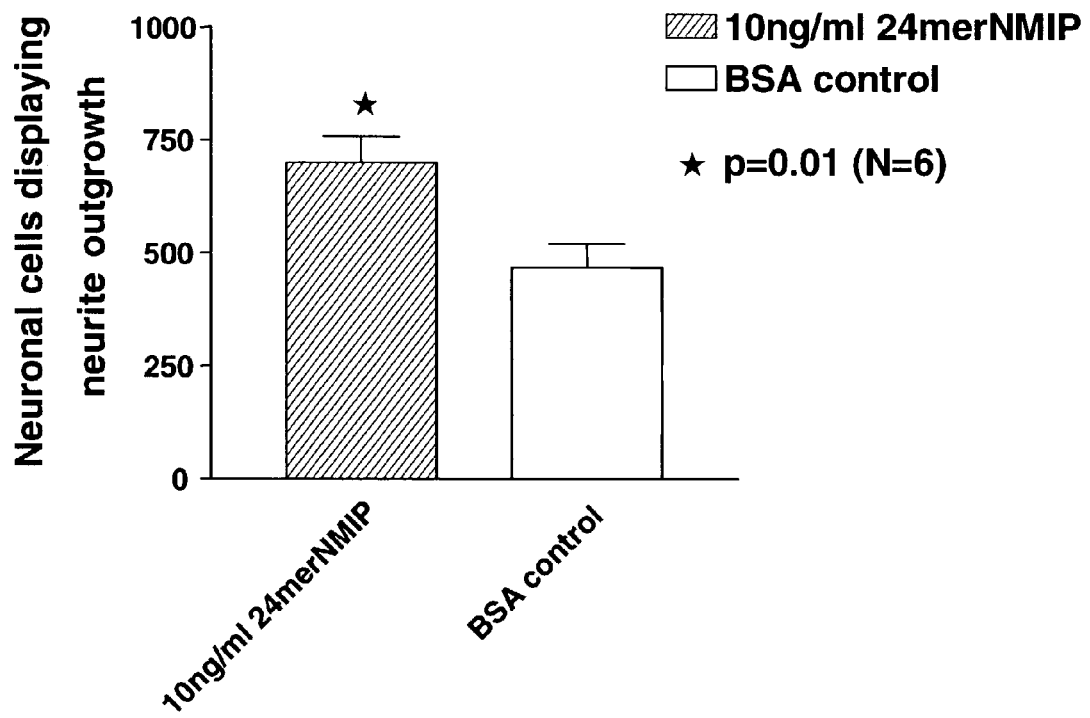
FIG. 25 depicts results of studies of the haptotactic migration assay using NRP-7 segment SW. NRP-7 (0.1 μg/ml and 1 μg/ml) was diluted in 10 μg/ml BSA and coated followed by 50 μg/ml PDL coating. Cortical cells were seeded into PDL-coated inserts and 1 pg/ml 24 mer peptide was added in solution. Cell counting was done after 1 day in vitro.

Biological activities of the arachne_contig 191157 mouse NRP (SEQ ID NO:17) were tested using a 24 mer NRP form of this peptide, which is located between amino acid residues 62-85 of the annotated NRP protein encoding sequence (from SEQ ID NO: 17). The neuronal survival activity conferred was maximal between 0.1-10 pM NRP applied within the cerebellar microexplant neurotoxicity assay (FIG. 23). After 48 hrs 1 pM of the 24 mer NRP (SEPEARRAPGRKGGV-VCASLAADW) SEQ ID NO:24 reconstituted in human transferrin revealed 57.0% recovery from oxidative/excitotoxic injury (see FIG. 22). Without reconstitution in human transferrin, the 24mer mouse NRP displayed less survival-promoting activity. The maximal activity range was then between 100 pM and 1 nM displaying 44.8% recovery from oxidative/excitotoxic injury at 100 pM mouse NRP (see FIG. 25).

Figure 24:
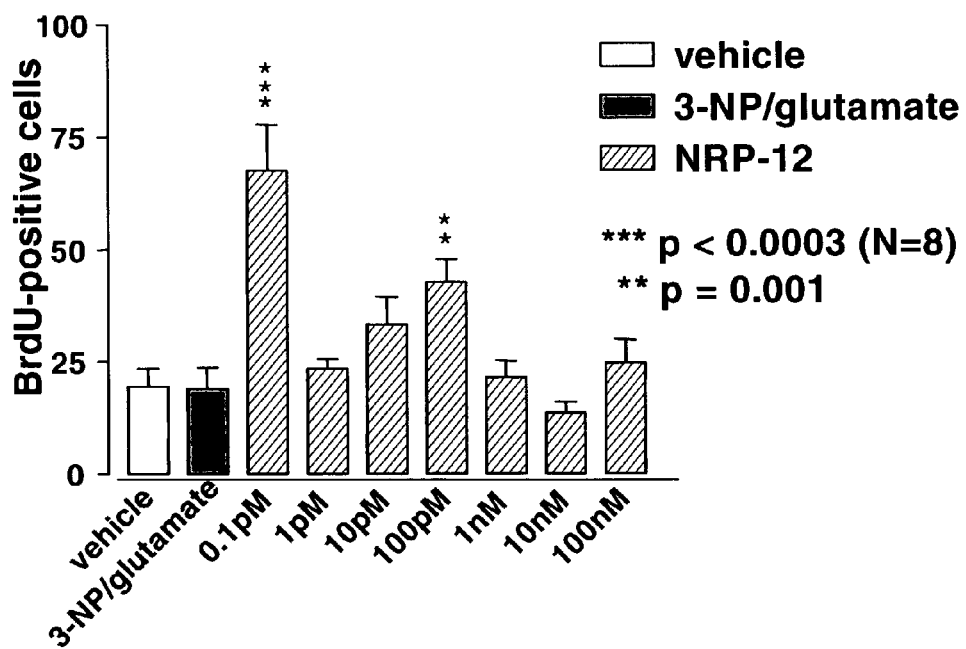
FIG. 24 depicts results of studies of proliferation induction under injury conditions using NRP-7 segment SW mouse peptide. Cerebellar microexplants were injured by 3-NP/glutamate. NRP and BrdU were administered simultaneously for 24 hrs. After 72 hrs BrdU-positive nuclei were counted within four microscopic fields for each culture. There was massive proliferation induction by 0.1 pM and 100 pM of mouse NRP-7. No proliferation differences between injured and non-injured cerebellar cells were observed. This indirectly indicates very low numbers of injury-induced proliferative astrocytes within the cerebellar microexplant system.

The 24 mer NRP was tested for neuronal proliferation inducing activity. Neuronal proliferation inducing activity for the mouse 24 mer NRP could be seen at 0.1 pM and 100 pM of mouse NRP with an up regulation of averages of 252.6% and 123.7%, respectively, of the proliferation rate observed for injured cerebellar microexplants (see FIG. 24). There was no difference between injured and non-injured (vehicle treatment) microexplants concerning the proliferation rate.

A 24 mer NRP was tested for chemoattractive activity using a haptotactic migration assay. The mouse 24 mer NRP was coated on Transwell® culture dishes in the presence of BSA followed by PDL-coating. Subsequently mouse NRP was given at 1 pg/ml directly into the medium. Seeded embryonic cortical cells migrated from the culture dish insert over a distance of 1 mm to the bottom of the culture dish. If mouse NRP was reconstituted in BSA followed by subsequent immobilization of 15 ng of the 24 mer mouse NRP, 49.8% more neurons migrated to the culture dish bottom after 1 day in vitro compared to BSA control alone (see FIG. 25).

We conclude that NRP-1 derived from hippocampal OTC supernatant with a molecular mass of 2046 induces neuronal proliferation and neuronal migration in the differentiated cultivated postnatal thalamus. Furthermore, NRP-1 induced neocortical neuronal migration by passing the barrier of the cortical basal lamina. The activity of NRP-1 is not tissue specific since cerebellar cells demonstrate strongly enhanced migratory behaviour in response to NRP-1 administration.

The results indicate an application for NRP-1 in inducing the proliferation and migration of neurons particularly in neurodegenerative diseases in which discrete areas degenerate and so a replenishment of new neurons is desired, eg. dopaminergic neuronal loss in the substantia nigra in Parkinson's disease, the cholinergic neuronal loss in the basal forebrain in Alzheimer's disease and GABAergic neuronal loss in the caudate nucleus and striatum in Huntington's disease.

The disclosed rat, human and mouse NRPs (and fragments thereof) possess similar activities. These peptides confer neuronal proliferation and migration-inducing activities as well as neurite outgrowth and neuronal survival-promoting activities to neurons.

The results further indicate that NRP compounds can be useful in situations in which neural repair is desirable. Such situations include diseases and injuries where neurons are damaged or have degenerated. Certain neurological diseases such as Alzheimer's disease, Parkinson's disease, Huntington's disease and others can be treated using the peptides of embodiments of this invention. Moreover, any type of neural damage, such as spinal cord or other central nervous system injuries can be treated using NRPs of this invention. Such injuries can be caused by trauma (blunt force or penetrating), hypoxia, such as caused by stroke, infarction, hypotension, or high altitude exposure.

The new assay systems described herein, although carried out using rat brain tissues, are an effective method for detecting and measuring activities of NRPs from any source, including human and murine sources. Because human and rodent NRPs share common peptide domains, embodiments of these assays is predictive of effects of NRPs in humans as well as other species that share at least one of characterisitc peptide domains identified herein.

Example 7

Purification of Rat NRP-1 From Hippocampal OTC Supernatant

Rat NRP-1 was purified from hippocampal OTCs. Sagittally cut slices 350 μm thick from the hippocampal formation of P0 Long Evans rats were prepared in oxygenated, protein-free minimal essential medium "MEM" followed by a 30 min recovery period at 4° C. Subsequently, the slices were put on 0.4 μm interface membranes and were cultured in protein-free MEM under an atmosphere of 1% $CO_2$ in air as an air-liquid interface culture according to methods described by Stoppini (Stoppini et al., 1991) for 7 to 14 days. Every three days, the cell culture supernatant was harvested and stored at −20° C. until usage.

Figure 26:
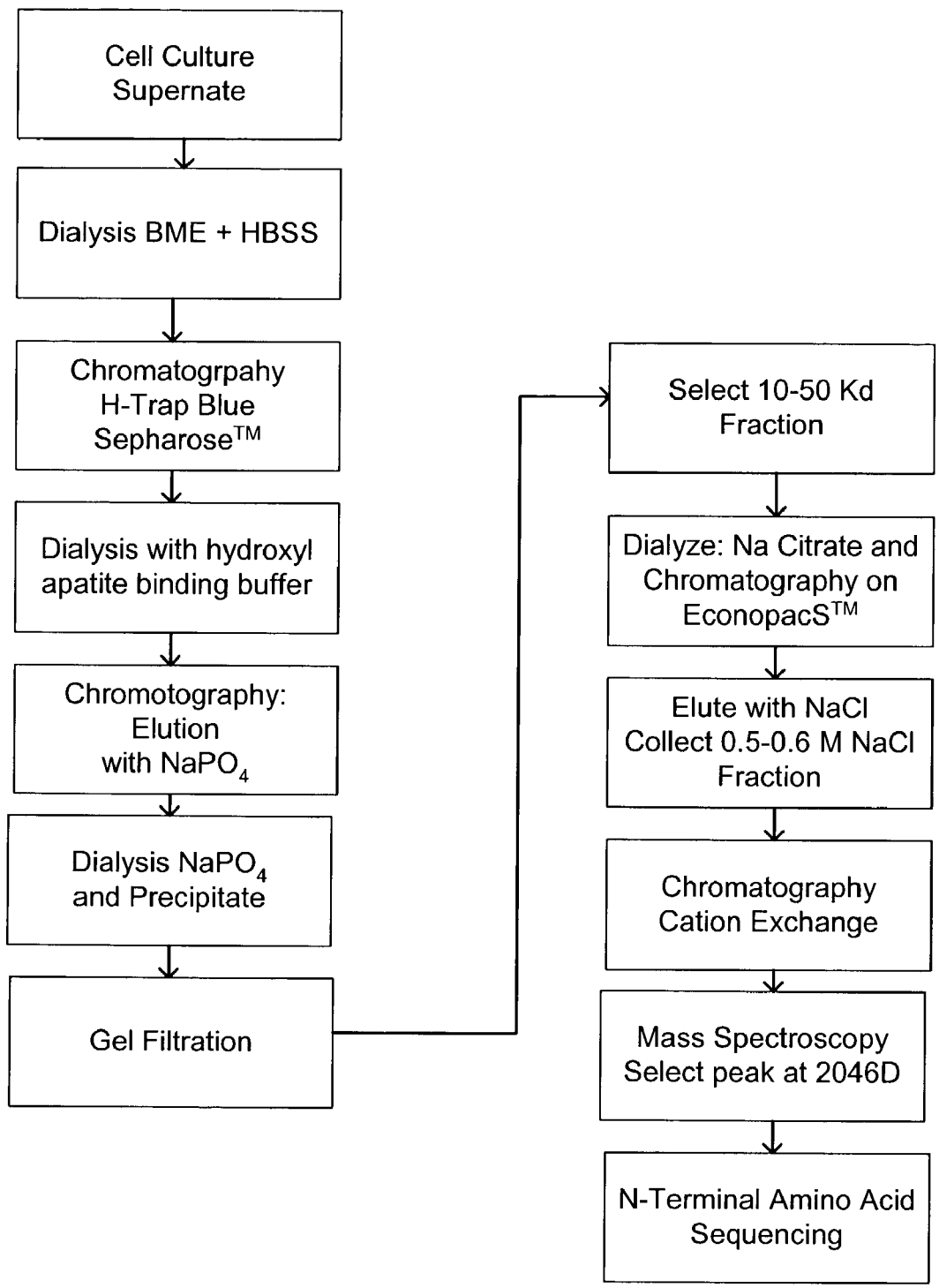
FIG. 26 depicts a flow chart of steps used to purify NRP-1.

Rat NRP-1 was purified from samples of 100 ml protein-free (BME-medium+HBSS) medium obtained after culture of cultivated hippocampal OTCs for from about 5 to 14 days (DIV). Supernatant from the samples was dialysed against 200 volumes of binding buffer (0.05 M potassium phosphate—pH 7). (See flowchart FIG. 26).

Chromatography was carried out at a flow rate of about 1 ml/min on a 5 ml column of HiTrap Blue Sepharose (Amersham/Pharmacia). Elution was done by a stepwise gradient using KCl, until a final concentration of 1.5 M KCl in binding buffer was used.

Subsequently, the eluted material from the Blue Sepharose column was subjected to dialysis against Hydroxy apatite binding buffer (0.01 M sodium phosphate—pH 7). Subsequent chromatography (1 ml/min) was on a 1 ml Hydroxy apatite column (Biorad). Elution was done by a stepwise gradient until a concentration of 0.4 M sodium phosphate (pH 6.8) was used.

The resulting eluate was dialysed against 0.01 M sodium phosphate (pH 7) and subsequently was precipitated by 80% (v/v) acetone at −20 ° C. for 3 hours. Centrifuged precipitate was reconstituted in 200 μl of 0.2 M NaCl, 0.05% (v/v) Tween 80, 0.02 M sodium phosphate (pH 7).

Gel filtration was carried out at a flow rate of 3.4 cm/h on Macroprep-40/1000 obtained from Biorad. The column dimension was 50×1.5 cm. Eluate with migration-inducing activity eluted at molecular weights of between 50,000-10,000.

Figure 27:
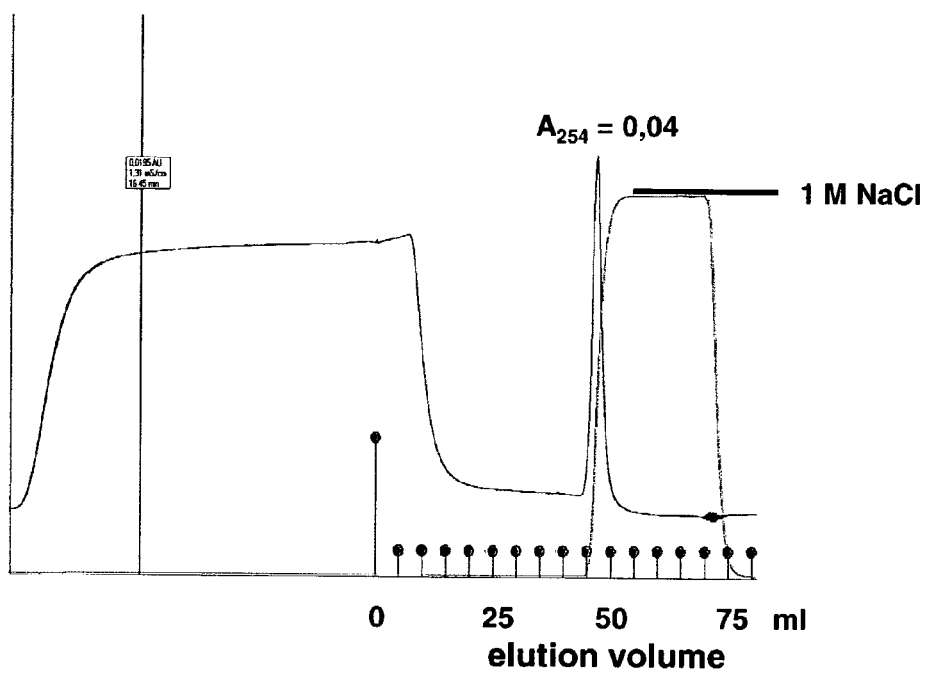
FIG. 27 depicts results of a cation exchange purification step to obtain homogenously purified NRP-1. Purification was carried out on High S (Biorad) cation exchanger using a low pressure chromatography unit from Biorad. 80% acetone-precipitated bioactive peak from gel filtration chromatography, extensively desalted against 10 mM citrate (pH 4), is chromatographed (1 ml/mm) in 0.01 M citrate (pH 4). The column was eluted using 1M NaCl in 0.01 M citrate (pH 4.5). Migration-promoting activity eluted between 43-53 ml elution volume. Absorbance was measured at 254 nm wavelength. Purity of the resulting NRP was verified by N-terminal amino acid sequencing, which produced unambiguous results.

Samples were then dialysed against 0.01 M sodium citrate (pH 4) and chromatography at a flow rate of (1 ml/min) on a 1 ml Econo-Pac S (Biorad) column was performed. Elution was done by a steep gradient of 1 M NaCl in binding buffer (pH 4.5). NRP-1 elutes between 0.5-0.6 M NaCl with an absorption maximum of 0.04 measured at 254 nm (see FIG. 27).

Figure 28:
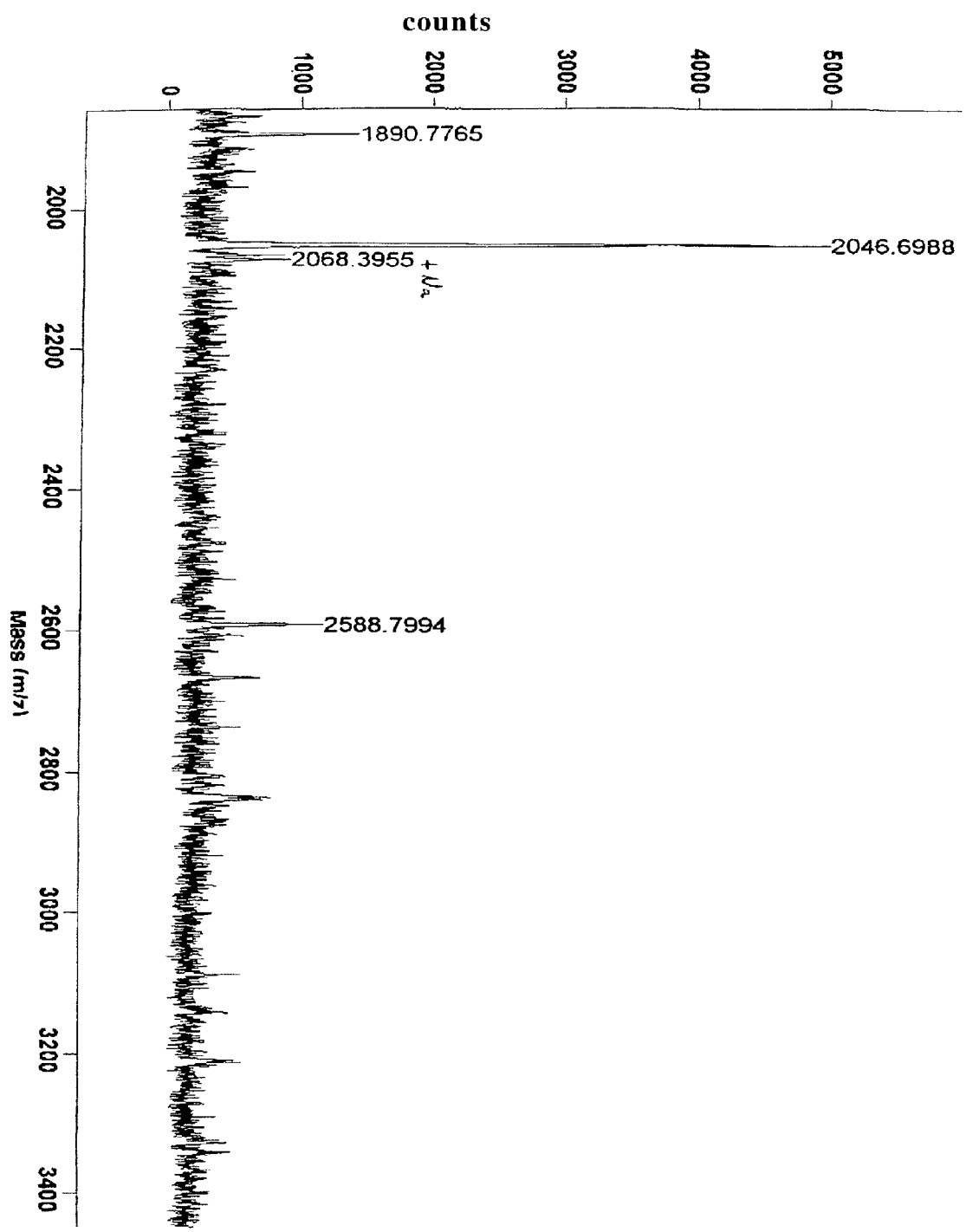
FIG. 28 depicts results of an analysis of NRP-1 by MALDI-TOF mass spectrometry. Purity and mass (M+H$^+$) of the major peptide from the cation exchange purification was confirmed by MALDI-TOF MS. The single charged peptide NRP-1 that represents the major peak has a molecular mass of 2046.

NRP-1 was homogenously purified after cation exchange chromatography (FIG. 15) as revealed by MALDI-TOF MS analysis (see FIG. 28). The mass spectrum revealed a main peak/abundance at a mass of 2046. The first 16 N-terminal amino acids have been sequenced, and resulted in unambiguous identification of those amino acids, indicating that the NRP-1 was substantially free of protein or peptide contaminants.

Purified protein was stored lyophilised at −80° C.

The obtained sequence revealed identity to a recently described survival-promoting peptide that consists of 30 amino acids (Cunningham et al., 1998) and the human cachexia protein (U.S. Pat. No. 5,834,192). Molecular mass calculation beginning from the sequenced C-terminus of the 16-residue NRP-1 compared to the ongoing sequence of the survival-promoting peptide and the human cachexia protein excluded the possibility that NRP-1 is a simple degradation product of the cachexia protein or survival-promoting peptide, respectively.

NRP-1 can be isolated and purified sufficiently to permit therapeutic use. Because NRP-1 can be purified, it can be administered to treat a neurological condition or nervous system injury in which neural repair is needed.

REFERENCES

Akerblom, I E, and Murry, L E (1996). Human cachexia associated protein. U.S. Pat. No. 5,834,192.

Anderson, C V, Wood, D M, Bigler, E D, and Blatter, D D (1996). Lesion volume, injury severity, and thalamic integrity following head injury. *J. Neurotrauma* 13: 35-40.

Anderson, W F (1992) Human gene therapy. *Science* 256: 808-813.

Bach et al., (1995) Insulin like growth factor binding proteins. *Diabetes Reviews* 3: 38-61.

Baldwin, M E, Roufail, S, Halford, M M, Alitalo, K, Stacker, S A and Achen, M G (2001). Multiple forms of mouse vascular endothelial growth factor-D are generated by RNA splicing and proteolysis. *J Biol Chem* 276: 44307-44314.

Beal, M F, Kowall, N W, Ellison, D W, Mazurek, M F, Swartz, K J, and Martin, J B (1986). Replication of the neurochemical characteristics of Huntington's disease by quinolinic acid. *Nature* 321: 168-171.

Bolz, J, Novak, N, and Staiger, V (1992). Formation of specific afferent connections on organotypic slice cultures from rat visual cortex cocultured with lateral geniculate nucleus. *J. Neurosci.* 12:3054-3070.

Brose, K, and Tessier-Lavigne, M (2000). Slit proteins: key regulators of axon guidance, axonal branching, and cell migration. *Curr. Opin. Neurobiol.* 10: 95-102. Cote, F, Do, T H, Laflamme, L, Gallo, J -M, and Gallo-Payet, N (1999). Activation of the AT2 receptor of angiotensin II induces neurite outgrowth and cell migration in microexplant cultures of the cerebellum. *J. Biol. Chem.* 274: 31686-31692.

Cunningham, T J, Hodge, L, Speicher, D, Reim, D, Tyler-Polsz, C, Levitt, P, Eagleson, K, Kennedy, S, and Wang, Y (1998). Identification of a survival promoting peptide in medium conditioned byoxidatively stressed cell lined of nervous system origin. *J. Neurosci.* 18: 7047-7060.

De Curtis, I, and Reichardt, L F (1993). Function and spatial distribution in developing chick retina of the laminin receptor α6β1 and its isoforms. *Development* 118: 377-388.

Dodd, J, Morton, S B, Karagogeos, D, Yamamoto, M, and Jessell, T M (1988). Spatial regulation of axonal glycoprotein expression on subsets of embryonic spinal neurons. *Neuron* 1: 105-116.

Dyke, M W, Bianchi-Scarra, G, and Musso, M (2001). Characterization of a triplex DNA-binding protein encoded by an alternative reading frame of loricrin. *Eur. J. Biochem* 268: 225-234.

Fallon, J, Reid, S, Kinyamu, R, Opole, I, Opole, R, Baratta, J, Korc, M, Endo, T L, Duong, A, Nguyen, G, Karkehabadhi, M, Twardzik, D, and Loughlin, S (2000). In vivo induction of massive proliferation, directed migration, and differentiation of neural cells in the adult mammalian brain. *PNAS* 97: 14686-14691.

Ferri, R T, and Levitt, P (1995). Regulation of regional differences in the differentiation of cerebral cortical neurons by EGF family-matrix interactions. *Development* 121: 1151-1160.

Fueshko, S, and Wray S (1994). LHRH cells migrate on peripherin fibers in embryonic olfactory explant cultures: an in vitro model for neurophilic neuronal migration. *Dev. Biol.* 166: 331-348.

Gähwiler, B H (1981). Organotypic monolayer cultures of nervous tissue. *J. Neurosci. Methods* 4:329-342.

Ganzler, S I, and Redies, C (1995). R-cadherin expression during nucleus formation in chicken forebrain. *J. Neurosci.* 15: 57-72.

Gomez, T M, and Spitzer, N C (1999). In vivo regulation of axon extension and pathfinding by growth-cone calcium transients. *Nature* 397: 350-355.

Gulyás, Al, Hájos, N, and Freund, T F (1996). Interneurons containing calretinin are specialized to control other neurons in the rat hippocampus. *J. Neurosci.* 16: 3397-3411.

Guth, S, Tange, T O, Kellenberger, E, Valcarcel, J (2001). Dual function for U2AF35 in AG-dependent pre-mRNA splicing. *Mol Cell Biol* 21: 7673-7681.

Hatten, M E, and Heintz, N (1999). Neurogenesis and migration—In Fundamental Neuroscience, (R: Zigmond, ed.), pp 451-479, Academic Press, San Diego.

Hermann, D M, Mies, G, Hata, R, and Hossmann, K A (2000). Microglial and astrocytic reactions prior to onset of thalamic cell death after traumatic lesion of the rat sensorimotor cortex. *Acta Neuropathol* (Berl) 99: 147-153.

Hughes, P E, Alexi, T, Williams, C E, Clark, R G, and Gluckman, P D (1999). Administration of recombinant human Activin-A has powerful neurotrophic effects on select striatal phenotypes in the quinolinic acid lesion model of Huntington's disease. *Neuroscience* 92: 197-209.

Hwang et al., (1980). Hepatic Uptake and degredation of unilamellar sphingomyelin/cholesterol liposomes: a kinetic study. *Proc. of the Natl. Acad. Of Sciences USA* 77: 4030-4034.

Ishii, N, Wadsworth, W G, Stem, B D, Culotti, J G, and Hedgecock, E M (1992). UNC-6, a laminin-related protein, guides cell and pioneer axon migrations in *C. elegans*. *Neuron* 9: 873-881.

Langer et al., (1981) Biocompatibility of polymeric delivery systems for macromolecules. *J. Biomed. Mater. Res.* 15: 27-277.

Liang, S, and Crutcher, K A (1992). Neuronal migration in vitro. *Dev. Brain Res.* 66: 127-132.

Lu, Q., Sun, E., Klein, R. S. and Flanagan I. G.(2001). Ephrin-β reverse signalling is mediated by a novel PDZ-RGS protein and selectively inhibits G-protein coupled in chemoattraction. *Cell* 105: 69-79.

Nakao, N, and Itakura, T (2000). Fetal tissue transplants in animal models of Huntington's disease: the effects on damaged neuronal circuitry and behavioural deficits. *Prog. Neurobiol.* 61: 313-338.

Obst, K, and Wahle, P (1995). Areal differences of NPY mRNA expressing neurons are established in the late postnatal rat visual cortex in vivo, but not in organotypic cultures. *Eur. J Neurosci.* 7: 2139-2158.

Pasterkamp, R J, Giger, R J, Baker, R E, Hermens, W T, and Verhaagen J (2000). Ectopic adenoviral vector-directed expression of Sema3A in organotypic spinal cord explants inhibits growth of primary sensory afferents. *Dev. Biol.* 220: 129-141.

Paxinos, G, Toerk, I, Tecott, L H, and Valentino, K L (1991). *Atlas of the Developing Brain*. Academic Press: San Diego.

Polleux, F, Morrow, T, and Ghosh, A (2000). Semaphorin3A is a chemoattractant for cortical dendrites. *Nature* 404: 567-573.

Rozas, G, Liste, I, Lopez-Martin, E, Guerra, Mj, Kokaia, M, and Labandeira-Garcia, J L (1996). Intrathalamic implants of GABA-releasing polymer matrices reduce motor impairments in rats with excitotoxically lesioned striata. *Exp. Neurol.* 142: 323-330.

Sieg, F, Obst, K, Gorba, T, Riederer, B. Pape, H -C, and Wahle, P (1998). Postnatal expression pattern of calcium-binding proteins in organotypic thalamic cultures and in the dorsal thalamus in vivo. *Dev. Brain Res.* 110: 83-95.

Stoppini, L, Buchs, P -A, and Muller, D (1991). A simple method for organotypic cultures of nervous tissue. *J. Neurosci. Methods* 37: 173-182.

Van der Flier, A, Kuikman, I, Kramer, D, Geerts, D, Kreft, M, Takafuta, T, Shapiro, S S and Sonnenberg, A (2002). Different splice variants of filamin-B affect myogenesis, subcellular distribution, and determine binding to integrin β subunits. *J. Cell Biol* 156: 361-376.

Wagener, R, Kobbe, B, Aszodi, A, Aeschlimann, D, and Paulsson M (2001). Characterization of the mouse matrilin-4 gene: A 5' antiparallel overlap with the gene encoding the transcription factor RBP-L. *Genomics* 76: 89-98.

Wagner et al., (1990) Transferrin-polycation conjugates as carriers for DNA uptake into cells. *Proc. Natl. Acad. Sci. USA.* 87: 3410-3414.

Wu et al., (1987) Receptor-mediated in vitro gene transformation by a soluble DNA carrier system. *J. Biol. Chem.* 262: 4429-4432.

Yamamoto M, Hassinger, L, and Crandall, J E (1990). Ultrastructural localization of stage-specific neurite-associated proteins in the developing rat cerebral and cerebellar cortices. *J. Neurocytol.* 19: 619-627.

Zhu, Y, Yu, T, Zhang, X -C, Nagasawa, T, Wu, J Y, Rao, Y (2002). Role of the chemokine SDF-1 as the meningeal attractant for embryonic cerebellar neurons. *Nature Neurosci.* 5: 719-720.

INDUSTRIAL APPLICABILITY

Embodiments of the genes of this invention are useful for use as compositions for therapy or for manufacture of medicaments for the treatment of neurological conditions in which increased neuron survival, neuronal migration, neural outgrowth and/or neural proliferation are desired. Such conditions include a variety of neurodegenerative diseases including Parkinson's Disease and Alzheimer's Disease.

We claim:

1. An isolated peptide consisting of the amino acid sequence selected from the group consisting of SEQ ID NO:5, SEQ ID NO:18 and SEQ ID NO: 25.

2. The isolated peptide of claim 1, where said amino acid sequence is SEQ ID NO:5.

3. The isolated peptide of claim 1, where said amino acid sequence is the sequence of SEQ ID NO:25.

4. An isolated peptide where the amino acid sequence is the sequence of SEQ ID NO:18.

* * * * *